US010844097B2

(12) United States Patent
Strugnell et al.

(10) Patent No.: US 10,844,097 B2
(45) Date of Patent: Nov. 24, 2020

(54) ENGINEERED INFLUENZA ANTIGENIC POLYPEPTIDES AND IMMUNOGENIC COMPOSITIONS THEREOF

(71) Applicant: Sanofi Pasteur Inc., Swiftwater, PA (US)

(72) Inventors: Tod Strugnell, Cambridge, MA (US); Eliud Oloo, Cambridge, MA (US)

(73) Assignee: Sanofi Pasteur Inc., Swiftwater, PA (US)

( * ) Notice: Subject to any disclaimer, the term of this patent is extended or adjusted under 35 U.S.C. 154(b) by 0 days.

(21) Appl. No.: 16/306,346

(22) PCT Filed: Jun. 2, 2017

(86) PCT No.: PCT/US2017/035747
§ 371 (c)(1),
(2) Date: Nov. 30, 2018

(87) PCT Pub. No.: WO2017/210599
PCT Pub. Date: Dec. 7, 2017

(65) Prior Publication Data
US 2019/0161519 A1    May 30, 2019

Related U.S. Application Data

(60) Provisional application No. 62/344,862, filed on Jun. 2, 2016.

(51) Int. Cl.
| | | |
|---|---|---|
| *C07K 14/11* | (2006.01) | |
| *G16B 15/20* | (2019.01) | |
| *A61K 39/145* | (2006.01) | |
| *C07K 14/005* | (2006.01) | |
| *A61P 31/16* | (2006.01) | |
| *G16B 15/30* | (2019.01) | |

(52) U.S. Cl.
CPC .............. *C07K 14/11* (2013.01); *A61P 31/16* (2018.01); *C07K 14/005* (2013.01); *G16B 15/20* (2019.02); *G16B 15/30* (2019.02); *A61K 39/145* (2013.01); *C12N 2760/16022* (2013.01); *C12N 2760/16034* (2013.01); *C12N 2760/16062* (2013.01)

(58) Field of Classification Search
None
See application file for complete search history.

(56) References Cited

U.S. PATENT DOCUMENTS

| | | | | |
|---|---|---|---|---|
| 9,234,008 B2* | 1/2016 | Ross | ................... | A61K 39/145 |
| 2014/0255438 A9* | 9/2014 | Song | ................... | C07K 14/195 |
| | | | | 424/186.1 |

| | | | |
|---|---|---|---|
| 2014/0286981 A1 | 9/2014 | Osorio | |
| 2015/0352202 A1 | 12/2015 | Osorio | |
| 2018/0298063 A1 | 10/2018 | Strugnell et al. | |

FOREIGN PATENT DOCUMENTS

| | | |
|---|---|---|
| WO | WO 2008094200 A2 | 8/2008 |
| WO | WO 2009026397 A2 | 2/2009 |
| WO | WO 2009076778 A1 | 6/2009 |
| WO | WO 2010003225 A1 | 1/2010 |
| WO | 2013044203 A2 | 3/2013 |
| WO | 2013119683 A1 | 8/2013 |
| WO | 2013148164 A1 | 10/2013 |
| WO | 2015184272 A2 | 3/2015 |
| WO | 2016100926 A1 | 6/2016 |
| WO | 2016/196846 A2 | 12/2016 |
| WO | 2016/201127 A1 | 12/2016 |

OTHER PUBLICATIONS

Kamlangdee et al. Broad Protection against Avian Influenza Virus by Using a Modified Vaccinia Ankara Virus Expressing a Mosaic Hemagglutinin Gene. Journal of Virology, 2014, 88: 13300-13309.*
Webby et al. Centralized Consensus Hemagglutinin Genes Induce Protective Immunity against H1, H3 and H5 Influenza Viruses. PLoS ONE, 2015, 10(10): e0140702.*
GenBank: AGX20074.1. hemagglutinin [Influenza B virus (B/Brisbane/163/2008)]. Dated Oct. 15, 2013.*
Koel et al. Substitutions Near the Receptor Binding Site Determine Major Antigenic Change During Influenza Virus Evolution. Science, 2013, 342: 976-979.*
Wang et al. Crystal Structure of Unliganded Influenza B Virus Hemagglutinin. J. Virol., 2008, 82: 3011-3020.*

(Continued)

*Primary Examiner* — Nianxiang Zou
(74) *Attorney, Agent, or Firm* — Proskauer Rose LLP; Fangli Chen

(57) ABSTRACT

The present invention provides, among other things, a novel and improved method for generating "mosaic" influenza antigenic polypeptides including hemagglutinin (HA) and neuraminidase (NA) polypeptides based on unique combination of epitope patterns that maximize exposure to epitopes present across multiple HA or NA sequences and therefore improved influenza strain coverage. In particular, the present invention provides engineered influenza B hemagglutinin (HA) polypeptides that are comprised of novel combinations of protective epitopes and antigenic regions from multiple influenza B viral strains. Such engineered HA polypeptides have improved properties over HA polypeptides developed through conventional approaches that rely on consensus alignments of viral sequences.

20 Claims, 23 Drawing Sheets

Specification includes a Sequence Listing.

(56) References Cited

OTHER PUBLICATIONS

GenBank: ACF54136.1. hemagglutinin [Influenza B virus (B/Taiwan/42/2007)]. Dated Jul. 21, 2008.*

Barouch et al., "Mosaic HIV-1 vaccines expand the breadth and depth of cellular immune responses in rhesus monkeys", Nature MEDI, Mar. 2010, Nature Pub. Co, 16(3): 319-323 and Supplementary figures (Feb. 21, 2010).

Fischer et al., "Polyvalent vaccines for optimal coverage of potential T-cell epitopes in global HIV-1 variants", Nature MEDI, Jan. 2007, Nature Pub. Co, 13(1): 100-106 (Dec. 24, 2006).

Kamlangdee et al., "Broad Protection against Avian Influenza Virus by Using a Modified Vaccinia Ankara Virus Expressing a Mosaic Hemagglutinin Gene", Journal of Virology., 88(22): 13300-13309 (Sep. 10, 2014).

Van Der Velden et al., "Safety and Immunogenicity of a Vero Cell Culture-Derived Whole-Virus H5NI Influenza Vaccine in Chronically III and Immunocompromised Patients", Clinical and Vaccine Immunology, 21(6): 867-876 (Apr. 16, 2014).

Carter, Donald M. et al., "Design and Characterization of a Computationally Optimized Broadly Reactive Hemagglutinin Vaccine for H1N1 Influenza Viruses", Journal of Virology (Online), American Society for Microbiology, US, 90(9): 4720-4734 (2016).

Kleanthous, Harry; Sanofi Pasteur, "Re-eingeneering HA as a strategy to develop universal influenza vaccines", (2013), URL: http://apps.who.int/vaccine_research/meetings/Harold_Kleanthous.pdf.
Koel et al., "Substitutions Near the Receptor Binding Site Determine Major Antigenic Change During Influenza Virus Evolution", Science, 342: 976-979 (2013).
Wan et al. "Molecular Basis for Broad Neuraminidase Immunity: Conserved Epitopes in Seasonal and Pandemic H1N1 as well as H5N1 Influenza Viruses", Journal of Virology, 87(16): 9290-9300 (Aug. 15, 2013).
Wang et al. "Crystal Structure of Unliganded Influenza B Virus Hemagglutinin", J. Viral., 82: 3011-3020 (2008).
Webby et al., "Centralized Consensus Hemagglutinin Genes Induce Protective Immunity against H 1, H3 and H5 Influenza Viruses", PLoS ONE, 10(10): e0140702 (2015).

* cited by examiner

Energy Scoring Function: a set of mathematical equations to compute an "energy" for a given protein conformation. The native conformation is usually the lowest energy conformation Score=$S_{LJ}$(atr+rep)+

$S_{solvation}$+$S_{hb}$(srbb+lrbb+sc)+

$S_{dunbrack}$+$S_{pair}$-$S_{ref}$+

$S_{prob1b}$+$S_{intrares}$+

$S_{gb\_elec}$+$S_{gsolt}$+$S_{h2o}$(solv+hb)+$S\_plane$+

...

```
                                    MSA                              MSA epitopes
A/Novosibirsk/151/2009    ILGNSECELLISKESWSYIVEK    A/Novosibirsk/151/2009    LISKES
A/Melbourne/1/1946        ILGNPECDSLLPASSWSYIVET    A/Melbourne/1/1946        LLPASS
A/FortWorth/1950          VLGNPECESLLSNRSWSYIAET    A/FortWorth/1950          LLSNRS
A/PuertoRico/8/1934       LLGNPECDPLLPVRSWSYIVET    A/PuertoRico/8/1934       LLPVRS
A/Melbourne/1935          LLGNPECDSLLPASSWSYIVET    A/Melbourne/1935          LLPASS
A/Novosibirsk/4/2009      ILGNPECELLVSKESWSYIVEK    A/Novosibirsk/4/2009      LVSKES
A/Denver/1957             VLGNPECESLLSNRSWSYIAET    A/Denver/1957             LLSNRS
A/Henry/1936              LLGNPECDPLLPARSWSYIVET    A/Henry/1936              LLPARS
A/UnitedKingdom/1/1933    LLGNPECDSLLPARSWSYIVET    A/UnitedKingdom/1/1933    LLPARS
A/PuertoRico/8/1934       LLGNPECDPLLPVRSWSYIVET ⇒  A/PuertoRico/8/1934       LLPVRS
A/Mongolia/153/88         LLGNPECDPLLPVRSWSYIVET    A/Mongolia/153/88         LLPVRS
A/PuertoRico/8/1934       LLGNPECDPLLPVRSWSYIVET    A/PuertoRico/8/1934       LLPVRS
A/Tokyo/3/1967            LLGNPECDSLLPARSWSYIVET    A/Tokyo/3/1967            LLPARS
A/Wilson-Smith/1933       LLGNPECDSLLPARSWSYIVET    A/Wilson-Smith/1933       LLPARS
A/NewJersey/11/1976       LLGNPECELLLTVSSWSYIVET    A/NewJersey/11/1976       LLTVSS
A/NewJersey/1976          LLGNPECELLLTVSSWSYIVET    A/NewJersey/1976          LLTVSS
A/Maryland/12/1991        LLGNPECELLFTASSWSYIVET    A/Maryland/12/1991        LFTASS
A/Ohio/3559/1988          LLGNPECELLFTASSWSYIVET    A/Ohio/3559/1988          LFTASS
A/Wisconsin/4755/1994     LLGNPECELLFTASSWSYIVET    A/Wisconsin/4755/1994     LFTASS
A/Ohio/01/2007            LLGNPECESLSTASSWSYIVET    A/Ohio/01/2007            LSTASS
A/Wisconsin/301/1976      LLGNPECELLFTVSSWSYIVET    A/Wisconsin/301/1976      LFTVSS Unique epitope sets         Epitope cassettes LISKES                LISKES    LLPVRS    LLTVSS
           LLPASS                LLPASS    LVSKES    LFTASS
           LLSNRS                LLSNRS    LLPARS    LSTASS
   ⇒       LLPVRS        ⇒       LLPVRS    LLTVSS    LFTVSS
           LVSKES                LVSKES    LFTASS    LLPVRS
           LLPARS                 ...       ...       ...
           LLTVSS
           LFTASS                  Other epitope cassettes
           LSTASS
           LFTVSS
```

>mosaic_AF4362_1 Ca12009:VNNKESSNEPG   Ca22009:SHARKSRN  138194:LLPARSWS  ...
...LLPARSWS.....................................EIFP...SWPN.ETN......SHARKS...
>mosaic_AF4362_2 Ca12009:INDKGTSREPG   Ca22009:PHAGAKRD  138194:LSTASSWS  ...
...LSTASSWS.....................................EIFP...SWPN.TVT......PHAGAK...

>mosaic_AF4362_1 Ca12009:VNNKESSNEPG   Ca22009:SHARKSRN   138194:LLPARSWS   ...
...LLPARSWSYIVETPNPENGTCYPGYFADYEELREQLSSVSSFERFEIFPKESSWPNHETNGVSASCSHARKS...
>mosaic_AF4362_2 Ca12009:INDKGTSREPG   Ca22009:PHAGAKRD   138194:LSTASSWS   ...
...LSTASSWSYIVETPNPENGTCYPGYFADYEELREQLSSVSSFERFEIFPKESSWPNHTVTGVSASCPHAGAK...

Figure 16

ENGINEERED INFLUENZA ANTIGENIC POLYPEPTIDES AND IMMUNOGENIC COMPOSITIONS THEREOF

CROSS REFERENCE TO RELATED APPLICATIONS

This application is a 35 U.S.C. § 371 National Stage Application of International Application No. PCT/US17/35747, filed Jun. 2, 2017, which claims priority to U.S. Provisional Patent Application 62/344,862 filed Jun. 2, 2016, the entirety of which is hereby incorporated by reference.

INCORPORATION-BY-REFERENCE OF SEQUENCE LISTING

The content of the text file named "SPR-010US SL.txt", which was created on Nov. 30, 2018 and is 139 KB in size, is hereby incorporated by reference in its entirety.

BACKGROUND

Influenza has a long standing history of pandemics, epidemics, resurgences and outbreaks. Vaccines have been the most effective defense against influenza. However, the effort to design and manufacture vaccines that induce strain-specific immunity year-over-year has been difficult and influenza continues to cause significant health problems across the globe. Indeed, currently marketed influenza vaccines must be updated annually based on predicted strains that will be present in human populations in the impending season.

Current influenza vaccines are based on inducing immunity to the hemagglutinin antigen present on the surface of influenza viruses. Hemagglutinin (HA) is a glycoprotein responsible for the binding of the influenza virus to cells with sialic acid-containing on surface structures on their membranes, and is highly variable across influenza virus strains. Among the current strategies for vaccination against influenza, the development of a universal vaccine holds the promise to increase the breadth of current strain-specific vaccines by focusing on relatively conserved regions of HA.

SUMMARY

The present invention provides, among other things, a novel and improved method for generating "mosaic" influenza antigenic polypeptides including hemagglutinin (HA) and neuraminidase (NA) polypeptides based on unique combination of epitope patterns that maximize exposure to epitopes present across multiple HA or NA sequences and therefore improve influenza strain coverage. In particular, the present invention provides engineered influenza B polypeptides that provide for improved protective immunity (e.g., a broad reactive immune response) to multiple influenza B virus isolates. The engineered HA polypeptides were developed by using a unique combination of epitope patterns to create "mosaic" HA polypeptides that maximize exposure to epitopes present across multiple HA sequences and therefore improved influenza strain coverage.

In one aspect, the present invention provides a method of engineering a mosaic influenza hemagglutinin (HA) polypeptide, comprising obtaining HA amino acid sequences from multiple circulating strains of a particular type and/or subtype of influenza virus; aligning the HA amino acid sequences to generate an alignment; identifying the positions of amino acids comprising known epitopes and antigenic regions; compiling the amino acid residues across the alignment at the identified positions for each epitope and antigenic region; defining a set of amino acid sequence patterns within the compiled sequences for each epitope and antigenic region, wherein each amino acid sequence pattern in the set is represented only once; selecting a sequence from the set for each epitope or antigenic region; and inserting one or more selected sequences into corresponding locations in a structural backbone of HA to generate a mosaic influenza HA polypeptide.

As used herein, "corresponding locations", in the context of an influenza HA or NA polypeptide sequence, generally refer to the locations that correspond to the location of the known epitopes and antigenic regions. Typically, "corresponding locations" on a polypeptide of interest (e.g., an HA polypeptide) are designated using a canonical numbering system based on a related reference polypeptide. Residues at "corresponding locations" of different HA or NA polypeptides need not actually be at the same locations.

In another aspect, the present invention provides a method of engineering a mosaic influenza hemagglutinin (HA) polypeptide, comprising obtaining HA amino acid sequences from multiple circulating strains of a particular type and/or subtype of influenza virus; aligning the HA amino acid sequences to generate an alignment; identifying the positions of amino acids comprising known epitopes and antigenic regions across the alignment; compiling the amino acid residues at the identified positions for each epitope and antigenic region; defining a set amino acid sequence patterns within the compiled sequences for each epitope and antigenic region, wherein each amino sequence pattern in the set is represented only once; generating a consensus sequence from each set for each epitope or antigenic region; and inserting one or more consensus sequences into corresponding locations in a structural backbone of HA to generate a mosaic influenza HA polypeptide.

In some embodiments, the methods described herein may be performed computationally. In particular embodiments, the methods may be performed using an algorithm.

In some embodiments, the locations in the structural model do not overlap.

In some embodiments, the steps of various methods according to the present invention are performed in silico by a suitably programmed computer system.

In some embodiments, a method of the present invention further comprises measuring the structural stability of the mosaic influenza HA polypeptide.

In some embodiments, measuring the stability comprises calculating the folding energy of each mosaic influenza HA polypeptide and selecting polypeptides that are likely to fold into a native-like conformation.

In some embodiments, the selecting step used in a method of the present invention further comprises ranking the selected sequences by sequence identity, geographical location and/or isolation date of the type or subtype of influenza virus. In some embodiments, the selecting step is random. In some embodiments, the sequences are selected so the mosaic influenza HA polypeptide elicits a broadly neutralizing immune response against multiple circulating influenza strains. In some embodiments, the sequences are selected according to a pre-determined algorithm.

In some embodiments, prior to the selecting step, the patterns in the set are weighted by their frequency of occurrence. In some embodiments, the selecting step comprises selecting the most frequently occurring sequence for each of the epitopes or antigenic regions. In some embodiments, the selecting step comprises selecting the second most frequently occurring sequence for each of the epitopes or antigenic regions. In some embodiments, the selecting step comprises selecting the third most frequently occurring sequence for each of the epitopes or antigenic regions.

In some embodiments, the obtaining step further comprises identifying redundant sequences by screening the HA amino acid sequences for those with 100%, or greater than 99.9%, 99% 98%, 97%, or 96% sequence identity, sequence identity, and removing all but one of the redundant sequences.

In some embodiments, the obtaining step according to a method of the present invention further comprises identifying and removing redundant sequences.

In some embodiments, the obtaining step comprises obtaining 100-5000 HA amino acid sequences from multiple circulating influenza strains.

In some embodiments, the obtaining step comprises obtaining all publicly available HA amino acid sequences.

In some embodiments, a method according to the present invention further comprises: generating a nucleic acid sequence corresponding to the mosaic influenza HA polypeptide; cloning the nucleic acid sequence into a mammalian expression vector; and transfecting a mammalian host cell with the mammalian expression vector. In some embodiments, the mammalian host cell is a Vero cell.

In some embodiments, the epitopes are neutralizing epitopes. In some embodiments, the epitopes are discontinuous epitopes. In some embodiments, the epitopes are continuous epitopes. In some embodiments, the epitopes are B cell epitopes.

In some embodiments, a method according to the present invention involves obtaining HA amino acid sequences from multiple circulating strains of a particular type and/or subtype of influenza virus which is a type A influenza virus. In some embodiments, the influenza A virus is selected from subtypes H1, H2, H3, H4, H5, H6, H7, H8, H9, H10, H11, H12, H13, H14, H15, or H16. In some embodiments, the influenza virus is elected from the group consisting of H1N1, H3N2, H5N1, and H7N9. In some embodiments, the type A virus is a seasonal strain. In particular embodiments, a method according to the present invention involves obtaining HA amino acid sequences from multiple circulating strains including/Texas/36/1991, A/Singapore/1986, A/New Caledonia/20/1999, A/Solomon Islands/03/2006, and A/Brisbane/59/2007 and A/Wisconsin/67/2005. In some embodiments, the type A virus is a pandemic strain. In some embodiments, a method according to the present invention involves obtaining HA amino acid sequences from multiple circulating strains including A/California/07/2009, A/California/04/2009, A/Belgium/145/2009, A/South Carolina/01/1918 and A/New Jersey/1976.

In some embodiments, a method according to the present invention involves obtaining HA amino acid sequences from multiple circulating strains of a particular type and/or subtype of influenza virus is a type B influenza virus. In some embodiments, the influenza B virus is a Yamagata lineage strain. In some embodiments, the influenza B virus is a Victoria lineage strain. In some embodiments, the influenza B virus strain circulated prior to the split into distinct lineages and is therefore neither a Yamagata nor Victoria lineage. In some embodiments, a method according to the present invention involves obtaining HA amino acid sequences from the influenza B virus selected from B/Hong Kong/330/2001, B/Hong Kong/05/1972, B/Lee/40, B/Massachusetts/02/2012, B/Panama/45/1990, B/Singapore/222/79, B/Victoria/02/1987, B/Yamagata/16/1988, or B/Brisbane/60/2008.

In yet another aspect, the present invention provides a method of engineering a mosaic influenza neuraminidase (NA) polypeptide, comprising: obtaining NA amino acid sequences from multiple circulating strains of a particular type and/or subtype of influenza virus; aligning the NA amino acid sequences to generate an alignment; identifying the positions of amino acids comprising known epitopes and antigenic regions; compiling the amino acid residues across the alignment at the identified positions for each epitope and antigenic region; defining a set of amino acid sequence patterns within the compiled sequences for each epitope and antigenic region, wherein each amino sequence pattern in the set is represented only once; selecting a sequence from the set for each epitope or antigenic region; and inserting selected sequences into corresponding locations in a structural backbone of NA to generate a mosaic influenza NA polypeptide.

In still another aspect, the present invention provides a method of engineering a mosaic influenza neuraminidase (NA) polypeptide, comprising: obtaining NA amino acid sequences from multiple circulating strains of a particular type and/or subtype of influenza virus; aligning the NA amino acid sequences to generate an alignment; identifying the positions of amino acids comprising known epitopes and antigenic regions across the alignment; compiling the amino acid residues at the identified positions for each epitope and antigenic region; defining a set amino acid sequence patterns within the compiled sequences for each epitope and antigenic region, wherein each amino sequence pattern in the set is represented only once; generating a consensus sequence from each set for each epitope or antigenic region; and inserting the consensus sequences into corresponding locations in a structural backbone of NA to generate a mosaic influenza NA polypeptide.

In some embodiments, the locations in the structural model do not overlap.

In some embodiments, the steps according to various methods described herein are performed in silico by a suitably programmed computer system.

In some embodiments, a method according to the present invention further comprises measuring the stability of the mosaic influenza NA polypeptide. In some embodiments, measuring the stability comprises calculating the folding energy of each mosaic influenza NA polypeptide and selecting polypeptides that are likely to fold into a native-like conformation.

In some embodiments, the selecting step further comprises ranking the selected sequences by sequence identity, geographical location and/or isolation date of the type or subtype of influenza virus. In some embodiments, the selecting step is random. In some embodiments, the sequences are selected so the mosaic influenza NA polypeptide elicits a broadly neutralizing immune response against the multiple circulating influenza strains. In some embodiments, the sequences are selected according to a pre-determined algorithm.

In some embodiments, prior to the selecting step, the patterns in the set are weighted by their frequency of occurrence. In some embodiments, the selecting step comprises selecting the most frequently occurring sequence for each of the epitopes or antigenic regions. In some embodiments, the selecting step comprises selecting the second most frequently occurring sequence for each of the epitopes or antigenic regions. In some embodiments, the selecting step comprises selecting the third most frequently occurring sequence for each of the epitopes or antigenic regions.

In some embodiments, the obtaining step according to a method of the present invention further comprises identifying redundant sequences by screening the NA amino acid sequences for those with 100%, or greater than 99.9%, 99% 98%, 97%, or 96% sequence identity, and removing all but one of the redundant sequences.

In some embodiments, the obtaining step according to a method of the present invention further comprises identifying and removing redundant sequences.

In some embodiments, the obtaining step comprises obtaining 100-5000 NA amino acid sequences from multiple circulating influenza strains.

In some embodiments, the obtaining step comprises obtaining all publicly available NA amino acid sequences.

In some embodiments, a method of the present invention further comprises generating a nucleic acid sequence corresponding to the mosaic influenza HA polypeptide; cloning the nucleic acid sequence into a mammalian expression vector; and transfecting a mammalian host cell with the mammalian expression vector. In some embodiments, the mammalian host cell is a Vero cell.

In some embodiments, the epitopes are neutralizing epitopes. In some embodiments, the epitopes are discontinuous epitopes.

Among other things, the present invention provides an engineered mosaic influenza HA or NA polypeptide according to various methods described here in, or a combination thereof.

In some embodiments, the present invention provides an engineered mosaic influenza hemagglutinin (HA) polypeptide comprising a mosaic amino acid sequence pattern defined by amino acid substitutions at residues 110, 140, 141, 143, 145, 146, 153, 154, 155, 156, 165, 174, 175, 176, 177, 179, 180, 181, 209, 210, 211, 212, 215, 216, 217, 228, 258, 259, 279 or a subset thereof, in the receptor binding site (RBS), as indexed by reference to a B/Brisbane/60/2008 amino acid sequence.

In some embodiments, the present invention provides an engineered mosaic influenza hemagglutinin (HA) polypeptide comprising a mosaic amino acid sequence pattern defined by amino acid substitutions 110F, 140I, 141D/N, 143E, 145A, 146P, 153G, 154T, 155S, 156G/R, 165S/I/N, 174A, 175V, 176P, 177K, 179D, 180N/S, 181N, 209H, 210S, 211D, 212N/D, 215Q, 216M, 217K/V, 228F, 258S, 259G, 279Q, or a subset thereof in the receptor binding site (RBS) as indexed by reference to a B/Brisbane/60/2008amino acid sequence.

In some embodiments, the subset comprises at least 20%, 30%, 40%, 50%, 60%, 70%, 75%, 80%, 85%, 90%, or 95% of the referenced residues. In some embodiments, the subset comprises at least 3, 4, 5, 6, 7, 8, 9, or 10 of the referenced residues.

In some embodiments, an engineered mosaic influenza HA polypeptide according to the present invention comprises a backbone from type B influenza virus. In some embodiments, the type B influenza virus is a Yamagata lineage strain. In some embodiments, the type B influenza virus is a Victoria lineage strain. In some embodiments, the type B influenza virus is selected from CAA25425|HA|Human|fluB|B/Singapore/222/79|Singapore|1979|, AGL06036|HA|Human|fluB|B/Massachusetts/02/2012|USA|2012/03/13|, ABL76694|HA|Human|fluB|B/Panama/45/1990|Panama|1990/03/07|, or AFH57909|HA|Human|fluB|B/Brisbane/60/2008|Australia|2008|.

In some embodiments, the present invention provides an engineered mosaic influenza hemagglutinin (HA) polypeptide comprising an amino acid sequence at least 90%, 95%, 96%, 97%, 98%, or 99% identical to SEQ ID NO: 40, wherein the amino acid sequence is not a naturally-occurring sequence. In some embodiments, the present invention provides engineered mosaic influenza HA polypeptides, wherein the amino acid sequence comprises SEQ ID NO: 40.

In one aspect, the present invention provides an engineered mosaic influenza hemagglutinin (HA) polypeptide comprising an amino acid sequence at least 90%, 95%, 96%, 97%, 98%, or 99% identical to SEQ ID NO: 41, wherein the amino acid sequence is not a naturally-occurring sequence. In some embodiments, the present invention provides engineered mosaic influenza HA polypeptides, wherein the amino acid sequence comprises SEQ ID NO: 41.

In one aspect, the present invention provides an engineered mosaic influenza hemagglutinin (HA) polypeptide comprising an amino acid sequence at least 90%, 95%, 96%, 97%, 98%, or 99% identical to SEQ ID NO: 42, wherein the amino acid sequence is not a naturally-occurring sequence. In some embodiments, the present invention provides engineered mosaic influenza HA polypeptides, wherein the amino acid sequence comprises SEQ ID NO: 42.

In one aspect, the present invention provides an engineered mosaic influenza hemagglutinin (HA) polypeptide comprising an amino acid sequence at least 90%, 95%, 96%, 97%, 98%, or 99% identical to SEQ ID NO: 43, wherein the amino acid sequence is not a naturally-occurring sequence. In some embodiments, the present invention provides engineered mosaic influenza HA polypeptides, wherein the amino acid sequence comprises SEQ ID NO: 43.

In one aspect, the present invention provides an engineered mosaic influenza hemagglutinin (HA) polypeptide comprising an amino acid sequence at least 90%, 95%, 96%, 97%, 98%, or 99% identical to SEQ ID NO: 44 wherein the amino acid sequence is not a naturally-occurring sequence. In some embodiments, the present invention provides engineered mosaic influenza HA polypeptides, wherein the amino acid sequence comprises SEQ ID NO: 44.

In one aspect, the present invention provides an engineered mosaic influenza hemagglutinin (HA) polypeptide comprising an amino acid sequence at least 90%, 95%, 96%, 97%, 98%, or 99% identical to SEQ ID NO: 45, wherein the amino acid sequence is not a naturally-occurring sequence. In some embodiments, the present invention provides engineered mosaic influenza HA polypeptides, wherein the amino acid sequence comprises SEQ ID NO: 45.

In related aspects, the present invention provides an isolated nucleic acid molecule encoding an engineered mosaic HA polypeptide according to various methods described herein. In some embodiments, the nucleic acid molecule is codon-optimized for expression in mammalian cells, microalgae, plants, yeast, fungi or bacteria. In some embodiments, the present invention provides a vector comprising the nucleic acid sequence encoding an engineered mosaic HA polypeptide described herein. In some embodiments, the present invention provides an isolated cell comprising a vector encoding an engineered mosaic HA polypeptide described herein. In some embodiments, the cell is a mammalian cell.

In other aspects, the present invention provides a fusion protein comprising an engineered mosaic HA polypeptide described herein.

In further aspect, the present invention provides a vaccine composition comprising an engineered mosaic HA polypeptide or a fusion protein thereof described herein. In some embodiments, the vaccine composition is a split inactivated virus.

In still other aspects, the present invention provides a method of immunizing a subject against influenza virus, comprising administering to the subject a vaccine composition comprising an engineered mosaic HA polypeptide or a fusion protein thereof. In some embodiments, the pharmaceutical composition further comprises an adjuvant. In some embodiments, a pharmaceutical composition, an influenza HA polypeptide, a fusion protein or an influenza VLP or split inactivated virus thereof as described herein, is administered intramuscularly, intranasally, intradermally, subcutaneously, orally, or intravenously.

It is to be understood that both the foregoing general description and the following detailed description are exemplary and explanatory only and are not restrictive of the invention, as claimed.

BRIEF DESCRIPTION OF THE DRAWING

The Drawing included herein, which is comprised of the following Figures, is for illustration purposes only not for limitation.

FIG. 1 shows a general illustration of the approach for designing engineered hemagglutinin (HA) polypeptides via structural mapping of antigenic repertoires. Mosaic antigen designs are constructed into a single HA molecule based on combinations of epitope patterns observed in HA sequences from circulating strains. Engineered HA molecules as described herein contain repertoires of neutralizing epitopes and antigenic sites or surface regions, which are computationally assembled from diverse strains. The epitopic regions are then selected which collectively elicit broadly neutralizing antibodies in a host.

FIG. 2 shows an exemplary flowchart for the design and production of engineered antigenic polypeptides.

FIG. 16 shows a detailed sequence overview of the mosaic approach.

Figure 3:
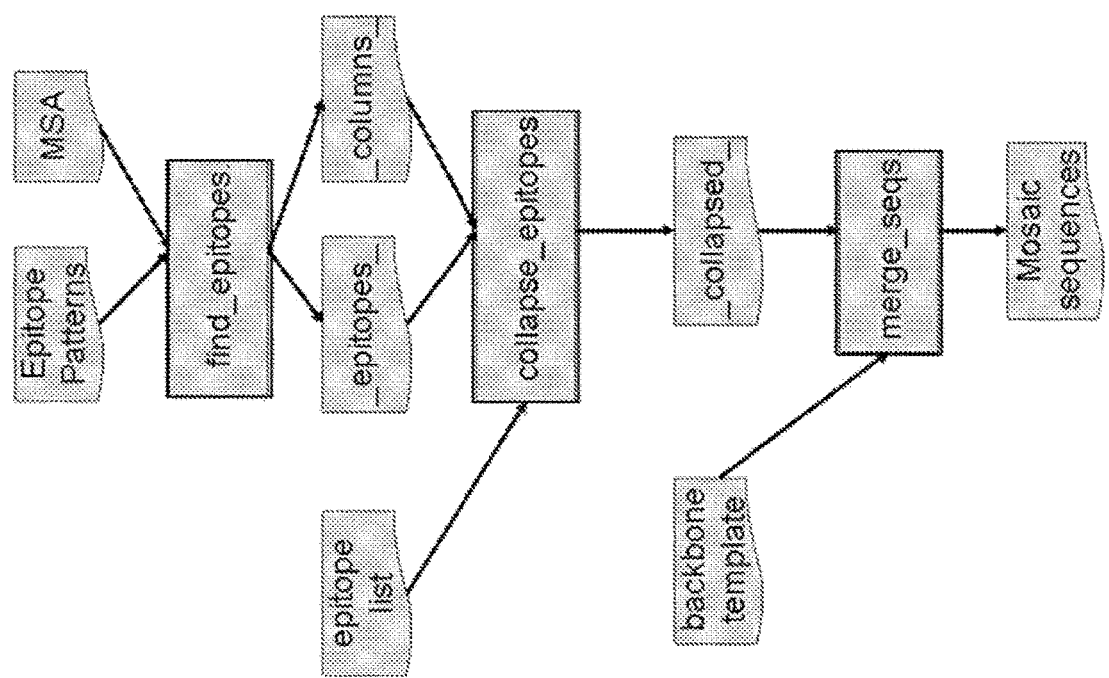
FIG. 3 shows an exemplary flowchart for the design and production of engineered antigenic polypeptides using the collapse epitopes process.

Antigen: As used herein, the term "antigen", refers to an agent that elicits an immune response; and/or (ii) an agent that is bound by a T cell receptor (e.g., when presented by an MHC molecule) or to an antibody (e.g., produced by a B cell) when exposed or administered to an organism. In some embodiments, an antigen elicits a humoral response (e.g., including production of antigen-specific antibodies) in an organism; alternatively or additionally, in some embodiments, an antigen elicits a cellular response (e.g., involving T-cells whose receptors specifically interact with the antigen) in an organism. It will be appreciated by those skilled in the art that a particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In some embodiments, an antigen reacts with the products of specific humoral or cellular immunity, including those induced by heterologous immunogens. In some embodiments of the disclosed compositions and methods, influenza HA protein is an antigen.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility of the disease, disorder, or condition (e.g., across a relevant population). In some embodiments, two or more entities are physically "associated" with one another if they interact, directly or indirectly, so that they are and remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can be assessed in any of a variety of contexts—including where interacting entities or moieties are studied in isolation or in the context of more complex systems (e.g., while covalently or otherwise associated with a carrier entity and/or in a biological system or cell).

Carrier: As used herein, the term "carrier" refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Characteristic Portion: As used herein, the term "characteristic portion" is used, in the broadest sense, to refer to a portion of a substance whose presence (or absence) correlates with presence (or absence) of a particular feature, attribute, or activity of the substance. In some embodiments, a characteristic portion of a substance is a portion that is found in the substance and in related substances that share the particular feature, attribute or activity, but not in those that do not share the particular feature, attribute or activity.

Characteristic sequence element: As used herein, the phrase "characteristic sequence element" refers to a sequence element found in a polymer (e.g., in a polypeptide or nucleic acid) that represents a characteristic portion of that polymer. In some embodiments, presence of a characteristic sequence element correlates with presence or level of a particular activity or property of the polymer. In some embodiments, presence (or absence) of a characteristic sequence element defines a particular polymer as a member (or not a member) of a particular family or group of such polymers. A characteristic sequence element typically comprises at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, 40, 45, 50, or more monomers (e.g., contiguously linked monomers). In some embodiments, a characteristic sequence element includes at least first and second stretches of continuous monomers spaced apart by one or more spacer regions whose length may or may not vary across polymers that share the sequence element.

Codon-optimized: As used herein, a "codon-optimized" nucleic acid sequence refers to a nucleic acid sequence that has been altered such that translation of the nucleic acid sequence and expression of the resulting protein is improved optimized for a particular expression system. A "codon-optimized" nucleic acid sequence encodes the same protein as a non-optimized parental sequence upon which the "codon-optimized" nucleic acid sequence is based. For example, a nucleic acid sequence may be "codon-optimized" for expression in mammalian cells (e.g., CHO cells, human cells, mouse cells etc.), bacterial cells (e.g., *E. coli*), insect cells, yeast cells or plant cells.

Comparable: The term "comparable", as used herein, refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

Corresponding to: As used herein, the term "corresponding to" is often used to designate the position/identity of an amino acid residue in a polypeptide of interest (e.g., an HA polypeptide). Those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the 190th amino acid in a particular amino acid chain but rather corresponds to the residue found at 190 in the reference polypeptide; those of ordinary skill in the art readily appreciate how to identify "corresponding" amino acids. Typically, residues in HA polypeptides are designated with reference to a canonical wild type HA, and reference in a polypeptide of interest that correspond to resides in the canonical wild type HA are described using the numbering of the residues to which they correspond.

Determine: Many methodologies described herein include a step of "determining". Those of ordinary skill in the art, reading the present specification, will appreciate that such "determining" can utilize any of a variety of techniques available to those skilled in the art, including for example specific techniques explicitly referred to herein. In some embodiments, a determination involves manipulation of a physical sample. In some embodiments, a determination involves consideration and/or manipulation of data or information, for example utilizing a computer or other processing unit adapted to perform a relevant analysis. In some embodiments, a determination involves receiving relevant information and/or materials from a source. In some embodiments, determining involves comparing one or more features of a sample or entity to a comparable reference.

Engineered: The term "engineered", as used herein, describes a polypeptide whose amino acid sequence has been designed by man and/or whose existence and production require human intervention and/or activity. For example, an engineered HA polypeptide has an amino acid sequence that is intentionally designed to elicit a particular effect and that differs from the amino acid sequences of HA polypeptides found in natural influenza isolates. In some embodiments, an engineered HA polypeptide has an amino acid sequence that differs from the amino acid sequence of HA polypeptides included in the NCBI database.

Epitope: As used herein, the term "epitope" includes any moiety that is specifically recognized by an immunoglobulin (e.g., antibody or receptor) binding component in whole or in part. In some embodiments, an epitope is comprised of a plurality of amino acid residues in an antigen. In some embodiments, the amino acid residues are surface-exposed when the antigen adopts a relevant three-dimensional conformation. In some embodiments, the amino acid residues are physically near to or continuous with each other in space when the antigen adopts such a conformation. In some embodiments, at least some of the amino acids are physically separated from one another when the antigen adopts an alternative conformation (e.g., is linearized; e.g., a non-linear epitope).

Excipient: As used herein, the term "excipient" refers to a non-therapeutic agent that may be included in a pharmaceutical composition, for example to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Expression: The term "expression" or "expressed", when used in reference to a nucleic acid herein, refers to one or more of the following events: (1) production of an RNA transcript of a DNA template (e.g., by transcription); (2) processing of an RNA transcript (e.g., by splicing, editing, 5' cap formation, and/or 3' end formation); (3) translation of an RNA into a polypeptide; and/or (4) post-translational modification of a polypeptide.

Fusion protein: As used herein, the term "fusion protein" refers to a protein encoded by a nucleic acid sequence engineered from nucleic acid sequences encoding at least a portion of two different (e.g., heterologous) proteins. As persons of skill are no doubt aware, to create a fusion protein nucleic acid sequences are joined such that the resulting reading does not contain an internal stop codon. In some embodiments, fusion proteins as described herein include an influenza HA polypeptide or fragment thereof.

Hemagglutinin (HA) polypeptide: As used herein, the term "hemagglutinin polypeptide" (or "HA polypeptide') refers to a polypeptide whose amino acid sequence includes at least one characteristic sequence of an influenza type A or B HA. A wide variety of HA sequences from influenza isolates are known in the art; indeed, the National Center for Biotechnology Information (NCBI) maintains a database (http://www.ncbi.nlm.nih.gov/genomes/FLU/) that, as of the filing of the present application includes approximately 40,000 HA sequences (for type A and B viruses). Those of ordinary skill in the art, referring to this database, can readily identify sequences that are characteristic of HA polypeptides generally, and/or of particular HA polypeptides (e.g., H1, H2, H3, H4, H5, H6, H7, H8, H9, H10, H11, H12, H13, H14, H15, or H16 polypeptides; or of HAs that mediate infection of particular hosts, e.g., human, avian, seal etc.). For example, in some embodiments, an HA polypeptide includes one or more characteristic sequence elements found between about residues 97 and about 185, about 324 and about 340, about 96 and about 100, and/or about 130 and about 230 of an HA protein found in a natural isolate of an influenza virus.

Host: The term "host" is used herein to refer to a system (e.g., a cell, organism, etc.) in which a polypeptide of interest is present. In some embodiments, a host is a system that is susceptible to infection with a particular infectious agent. In some embodiments, a host is a system that expresses a particular polypeptide of interest.

Host cell: As used herein, the phrase "host cell" refers to a cell into which exogenous DNA (recombinant or otherwise) has been introduced. For example, host cells may be used to produce the engineered influenza hemagglutinin polypeptides described herein by standard recombinant techniques. Persons of skill upon reading this disclosure will understand that such terms refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include any prokaryotic and eukaryotic cells suitable for expressing an exogenous DNA (e.g., a recombinant nucleic acid sequence). Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell).

Immune response: As used herein, the term "immune response" refers to a response of a cell of the immune system, such as a B cell, T cell, dendritic cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate and/or adaptive immune response. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

Immunogen: As used herein, the term "immunogen" refers to a compound, composition, or substance which is capable, under appropriate conditions, of stimulating an immune response, such as the production of antibodies or a T cell response in an animal, including compositions that are injected or absorbed into an animal. As used herein, an "immunogenic composition" is an administrable composition comprising an immunogen (such as an HA polypeptide). "Immunogenic compositions" include, for example, vaccines. As used herein, "immunize" means to render a subject protected from an infectious disease, such as by vaccination.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Influenza virus: As used herein, the term "influenza virus" refers to a segmented negative-strand RNA virus that belongs to the Orthomyxoviridae family. There are three types of Influenza viruses, A, B, and C. Influenza B viruses have been reported to infect humans, seals, horses and swine. Human influenza A and B viruses (A and B viruses) are equally prevalent among human beings, yet most A virus genes evolve two to three times faster than the corresponding genes in B viruses. Most influenza B viruses cause mild localized infections of the respiratory and intestinal tract in humans. Influenza B causes the same spectrum of disease as influenza A but does not cause pandemics. In 2016, the WHO GISRS laboratories reported that of more than 80,000 samples tested, 35.7% were typed as influenza A and 64.3% as influenza B. Of the characterized B viruses, 20.6% belonged to the B-Yamagata lineage and 79.4% to the B-Victoria lineage.

Influenza vaccine: As used herein, the term "influenza vaccine" refers to an immunogenic composition capable of stimulating an immune response, administered for the prevention, amelioration, or treatment of influenza virus infection. An influenza vaccine may include, for example, attenuated or killed influenza virus, virus-like particles (VLPs) and/or antigenic polypeptides (e.g., the engineered hemagglutinins described herein) or DNA derived from them, or any recombinant versions of such immunogenic materials.

Isolated: As used herein, the term "isolated" refers to a substance and/or entity that has been (1) separated from at least some of the components with which it was associated when initially produced (whether in nature and/or in an experimental setting), and/or (2) designed, produced, prepared, and/or manufactured with human intervention. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

Nucleic acid: As used herein, the phrase "nucleic acid", in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

Pandemic strain: A "pandemic" influenza strain is one that has caused or has capacity to cause pandemic infection of human populations. In some embodiments, a pandemic strain has caused pandemic infection. In some embodiments, such pandemic infection involves epidemic infection across multiple territories; in some embodiments, pandemic infection involves infection across territories that are separated from one another (e.g., by mountains, bodies of water, as part of distinct continents, etc.) such that infections ordinarily do not pass between them.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 15$^{th}$ Edition (1975), describes compositions and formulations suitable for pharmaceutical delivery of one or more therapeutic compositions, such as one or more influenza vaccines, and additional pharmaceutical agents. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Prevention: The term "prevention", as used herein, refers to prophylaxis, avoidance of disease manifestation, a delay of onset, and/or reduction in frequency and/or severity of one or more symptoms of a particular disease, disorder or condition (e.g., infection for example with influenza virus). In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition.

Receptor-Binding Site (RBS): As used herein, the term "receptor-binding site" or "RBS" comprises contiguous or non-contiguous amino acid residues of the head region of an influenza HA polypeptide, which include amino acids involved in direct binding of sialic acid on the target cell receptor proteins. Amino acid residues that make up a "receptor-binding site" or "RBS" of an influenza HA polypeptide may be described from crystal structures of HA polypeptides complexed with sialic acid analogs and identifying amino acid residues within a certain proximity to the analog or may be described in reference to an HA polypeptide sequence from a particular viral strain (e.g., B/Victoria/02/1987, B/Yamagata/16/1988). Thus, in some embodiments, the "receptor-binding site" or "RBS" of an engineered HA polypeptide as described herein may be determined using a reference HA polypeptide sequence. In some embodiments, the "receptor-binding site" or "RBS" of an engineered HA polypeptide as described herein may be determined using the crystal structures of HA polypeptide sequence. An exemplary reference crystal structure of HA polypeptide sequence includes B/Yamanashi/166/1998 influenza B pdb|4M40.

Recombinant: As used herein, the term "recombinant" is intended to refer to polypeptides (e.g., HA polypeptides as described herein) that are designed, engineered, prepared, expressed, created or isolated by recombinant means, such as polypeptides expressed using a recombinant expression vector transfected into a host cell, polypeptides isolated from a recombinant, combinatorial polypeptide library or polypeptides prepared, expressed, created or isolated by any other means that involves splicing selected sequence elements to one another. In some embodiments, one or more of such selected sequence elements is found in nature. In some embodiments, one or more of such selected sequence elements and/or combinations thereof is designed in silico. In some embodiments, one or more such selected sequence elements results from the combination of multiple (e.g., two or more) known sequence elements that are not naturally present in the same polypeptide (e.g., two epitopes from two separate HA polypeptides).

Recombinant influenza vaccine: As used herein, the term "recombinant influenza vaccine" refers to influenza-specific immunogenic composition comprising one or more of the engineered influenza hemagglutinins described herein, including, but not limited to whole influenza virus, subunit preparations thereof, virus-like particles, recombinant protein (i.e., preparations composed of recombinant HA purified to varying degree), and DNA- and viral vector-based vaccines. Recombinant influenza vaccines as described herein may optionally contain one or more adjuvants.

Reference: The term "reference" is often used herein to describe a standard or control agent, individual, population, sample, sequence or value against which an agent, individual, population, sample, sequence or value of interest is compared. In some embodiments, a reference agent, individual, population, sample, sequence or value is tested and/or determined substantially simultaneously with the testing or determination of the agent, individual, population, sample, sequence or value of interest. In some embodiments, a reference agent, individual, population, sample, sequence or value is a historical reference, optionally embodied in a tangible medium. Typically, as would be understood by those skilled in the art, a reference agent, individual, population, sample, sequence or value is determined or characterized under conditions comparable to those utilized to determine or characterize the agent, individual, population, sample, sequence or value of interest.

Specificity: As is known in the art, "specificity" is a measure of the ability of a particular ligand (e.g., an antibody, an HA polypeptide, etc.) to distinguish its binding partner (e.g., an antigen, a human HA receptor, and particularly a human upper respiratory tract HA receptor) from other potential binding partners (e.g., a seal HA receptor).

Subject: As used herein, the term "subject" means any mammal, including humans. In certain embodiments of the present invention the subject is an adult, an adolescent or an infant. In some embodiments, terms "individual" or "patient" are used and are intended to be interchangeable with "subject". Also contemplated by the present invention are the administration of the pharmaceutical compositions and/or performance of the methods of treatment in-utero.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially Similar: As used herein, the term "substantially similar" refers to a comparison between two entities. In general, entities are considered to be "substantially similar" to one another when they share sufficient structural similarity (e.g., a characteristic structural feature) that they have a comparable likelihood of sharing one or more additional attributes or features. To give but one example, a characteristic, for example, glycosylation site pattern, being either the same or similar enough between two influenza strains, that the human pandemic risk of each strain is the same.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul et al., Nucleic Acids Res. 25:3389-3402, 1997; Baxevanis et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues. In the context of an HA polypeptide, reference to "substantial identity" typically refers to a HA polypeptide (or HA epitope) having an amino acid sequence at least 90%, preferably at least 91%, at least 92%, at least 93%, at least 94%, at least 95%, at least 96%, at least 97%, at least 98%, or at least 99% identical to that of a reference HA polypeptide (or HA epitope).

Transformation: As used herein, refers to any process by which exogenous DNA is introduced into a host cell. Transformation may occur under natural or artificial conditions using various methods well known in the art. Transformation may rely on any known method for the insertion of foreign nucleic acid sequences into a prokaryotic or eukaryotic host cell. In some embodiments, a particular transformation methodology is selected based on the host cell being transformed and may include, but is not limited to, viral infection, electroporation, mating, lipofection. In some embodiments, a "transformed" cell is stably transformed in that the inserted DNA is capable of replication either as an autonomously replicating plasmid or as part of the host chromosome. In some embodiments, a transformed cell transiently expresses introduced nucleic acid for limited periods of time.

Vaccination: As used herein, the term "vaccination" refers to the administration of a composition intended to generate an immune response, for example to a disease-causing agent. Vaccination can be administered before, during, and/or after exposure to a disease-causing agent, and/or to the development of one or more symptoms, and in some embodiments, before, during, and/or shortly after exposure to the agent. In some embodiments, vaccination includes multiple administrations, appropriately spaced in time, of a vaccinating composition.

Vector: As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

Virus-like particle (VLP): As used herein, the phrase "virus-like particle" or "VLP" refers to particles that resemble a virus yet lack any viral genetic material and, therefore, are not infectious. A "virus-like particle" or "VLP" may be produced by heterologous expression in a variety of cell culture systems including mammalian cell lines, insect cell lines, yeast, and plant cells. In addition, VLPs can be purified by methods known in the art. In some embodiments, an influenza VLP as described herein comprises hemagglutinin (HA) polypeptides and neuraminidase (NA) polypeptides. In some embodiments, influenza VLPs as described herein comprise HA polypeptides, NA polypeptides and/or viral structural polypeptides (e.g., an influenza structural protein such as influenza M1). In some certain embodiments, influenza VLPs as described herein comprise HA polypeptides, NA polypeptides and/or M1 polypeptides. In some embodiments, influenza VLPs as described herein comprise HA polypeptides, NA polypeptides and/or HIVgag polypeptides. Influenza VLPs can be produced by transfection of host cells (e.g., mammalian cells) with plasmids encoding HA and NA proteins, and optionally HIVgag proteins. After incubation of the transfected cells for an appropriate time to allow for protein expression (such as for approximately 72 hours), VLPs can be isolated from cell culture supernatants. In some embodiments, influenza VLPs as described herein are produced by transient transfection in mammalian cells (e.g., human cells). In some embodiments, influenza VLPs are analyzed by the use of one or more assays. To give but a few examples, influenza VLPs may be analyzed for hemagglutinin activity, dynamic light scattering and hemmagglutinin content quantitation by protein staining. Other assays will be readily apparent to persons of skill upon reviewing the present disclosure.

Wild type: As is understood in the art, the phrase "wild type" generally refers to a normal form of a protein or nucleic acid, as is found in nature. For example, wild type HA polypeptides are found in natural isolates of influenza virus. A variety of different wild type HA sequences can be found in the NCBI influenza virus sequence database, available through the world wide web at ncbi.nlm.nih.gov/genomes/FLU/FLU.

DETAILED DESCRIPTION OF CERTAIN EMBODIMENTS

The present invention is not limited to particular methods, and experimental conditions described, as such methods and conditions may vary. It is also to be understood that the terminology used herein is for the purpose of describing particular embodiments only, and is not intended to be limiting unless indicated, since the scope of the present invention will be limited only by the appended claims.

Unless stated otherwise, all technical and scientific terms and phrases used herein have the same meaning as commonly understood by one of ordinary skill in the art. Although any methods and materials similar or equivalent to those described herein can be used in the practice or testing of the present invention, the preferred methods and materials are now described. All publications mentioned herein are incorporated herein by reference.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

Engineering Mosaic Influenza Antigens

Influenza viruses are members of the family Orthomyxoviridae and are divided into three genera, A, B, and C. Influenza A and B viruses cause respiratory infections in humans. Current vaccines are designed to induce immunity to hemagglutinin, one of two glycoproteins present on the surface of influenza viruses. Despite the availability of highly effective vaccines, influenza infection still results in up to 5,000,000 hospitalizations and 500,000 deaths annually worldwide. Currently available vaccines against influenza include up to four influenza hemagglutinin components intended to provide protection against H1N1, H3N2, and influenza B strains. Vaccine compositions are reassessed annually by the World Health Organization (WHO) to accommodate antigenic shift and drift in circulating virus strains. Such a strategy requires diligent surveillance of circulating influenza strains from year to year, and vaccine mismatches resulting from inaccurate predictions or unpredictable HA mutations arising during vaccine manufacture, which can result in increased morbidity and mortality even in vaccinated populations. Given the shortcomings of the currently available vaccines, a key goal of influenza research is to develop vaccination approaches that provide greater efficacy against mismatched strains.

Structural Mapping of Antigenic Repertoires

Figure 1:
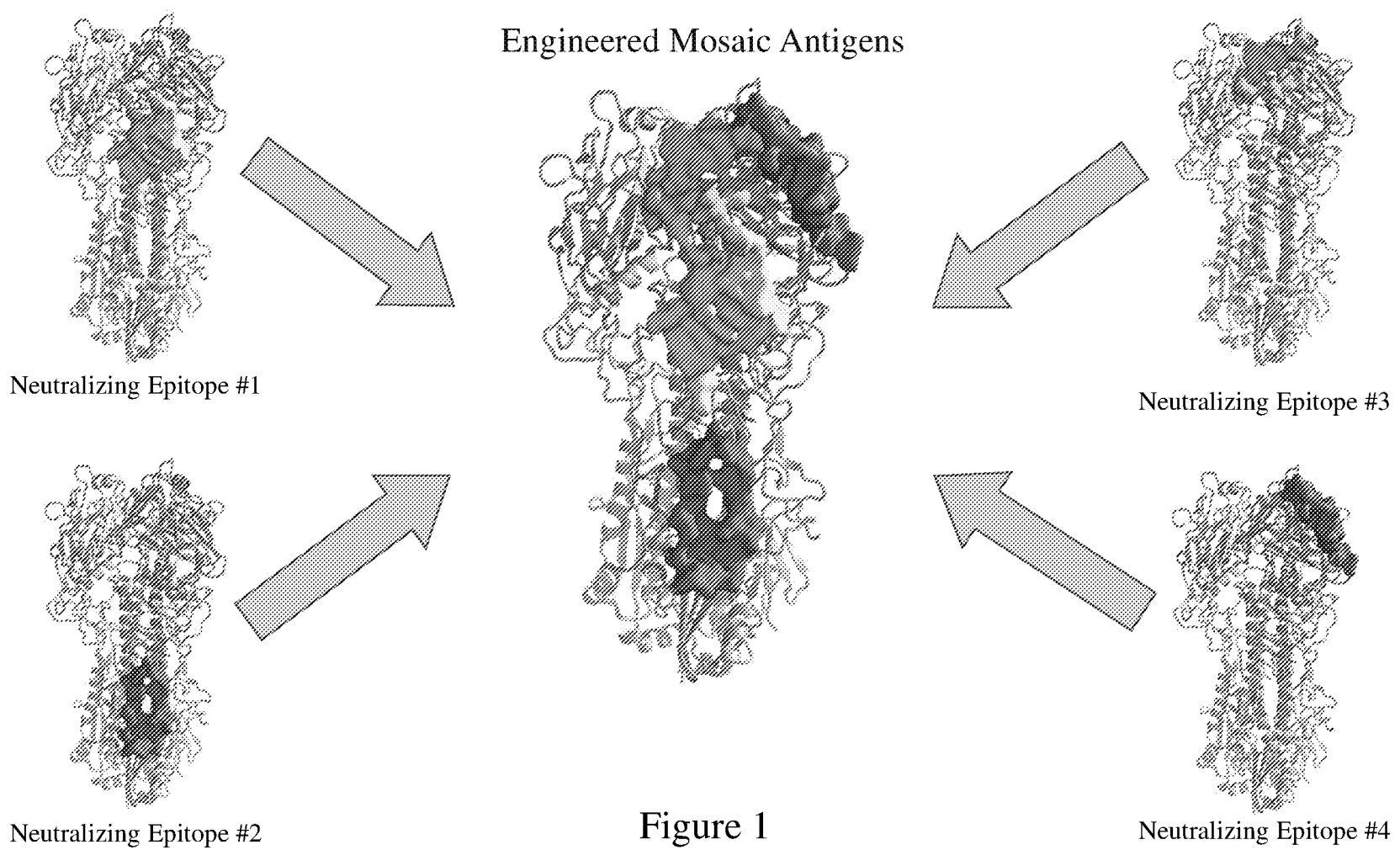

One rational design approach to creating a broadly protective influenza vaccine is to engineer antigens that include epitopes from as many viral isolates as possible. According to the present invention, generation of mosaic epitope sequences, in particular—B-cell epitope sequences—can be achieved using a methodology termed SMARt for the 'Structural Mapping of Antigenic Repertoires'. The present invention is based, in part, on the recognition that a rational design approach to creating a broadly protective influenza vaccine can be developed by providing engineered influenza antigenic polypeptides (for example, hemagglutinin, neuraminidase, M2e, etc.) that include epitopes from multiple viral isolates in a polyvalent vaccine (FIG. 1). The designs, in some embodiments, are based on combinations of multiple B cell epitopes and antigenic regions from different hemagglutinin sequences into mosaic antigens. These mosaic epitope antigens, in some embodiments, are predicted to confer cross-protection against multiple influenza B lineage strains by maximizing sequence homology for at least one neutralizing epitope.

In some embodiments, a method of engineering a mosaic influenza hemagglutinin (HA) polypeptide according to the SMARt methodology comprises the steps of: (1) obtaining HA amino acid sequences from multiple circulating strains of a particular type and/or subtype of influenza virus; (2) aligning the HA amino acid sequences to generate an alignment; identifying the positions of amino acids comprising known epitopes and antigenic regions; (3) compiling the amino acid residues across the alignment at the identified positions for each epitope and antigenic region; (3) defining a set of amino acid sequence patterns within the compiled sequences for each epitope and antigenic region, wherein each amino sequence pattern in the set is represented only once; (4) selecting a sequence from the set for each epitope or antigenic region; and (5) inserting one or more selected sequences into corresponding locations in a structural backbone of HA to generate a mosaic influenza HA polypeptide. Alternatively, instead of selecting a unique sequence at step (4), a consensus sequence is defined from each set for each epitope or antigenic region.

Hemagglutinin (HA) is responsible for the binding of influenza virus to target cells with sialic acid on their membranes. Over time, HA accumulates mutations in its sequence in a process termed 'antigenic drift', allowing the virus to evade the human immune response. Although Influenza B viruses mutate at a lower rate than Influenza A viruses, the rate of mutation is fast enough that periodic reformulation of the Influenza B component of vaccines is required. Additionally, Influenza B virus has diverged into two antigenically distinct lineages (Yamagata and Victoria).

Current vaccines are designed to protect against the predominant circulating strains of Influenza A (subtype H1N1 and H3N2) and Influenza B. Previously, the Influenza B component of influenza vaccines was specific for a single lineage; with the introduction of quadrivalent influenza vaccine (QIV), both Influenza B lineages are now represented in a single vaccine. Accumulating mutations in HA reduce the effectiveness of any existing vaccine to protect against future circulating influenza viruses. Consequently, currently marketed influenza vaccines must be reviewed annually and updated if necessary. The development of a broadly protective vaccine antigen that tolerates some amount of antigenic drift holds the promise to increase the breadth of response as compared to current vaccines, which are more strain-specific. Additionally, a broadly protective Influenza B HA should provide a cross protective immune response against both Influenza B lineages, Yamagata and Victoria.

In some embodiments, engineered HA polypeptides as described herein achieve a greater efficacy against mismatched strains and/or strains associated with an increased morbidity and/or mortality. In some embodiments, engineered HA polypeptides as described herein provide enhanced protection against influenza during mismatch years thereby reducing reliance on accurate strain predictions from year to year. In some embodiments, engineered HA polypeptides as described herein are used in vaccines and allow for less frequent immunizations by providing sufficient breadth of immunity to cover antigenic drift that generally accumulates between seasons of influenza infection.

Engineered hemagglutinin (HA) polypeptides are molecular entities that specifically elicit an immune response in a subject. Such engineered HA polypeptides find a variety of uses in the art, including prophylactic and therapeutic uses. Engineered HA polypeptides of the present invention, in some embodiments, address the lack of breadth and cross-protection observed in current influenza vaccine formulations. For example, in some embodiments, engineered HA polypeptides as described herein provide a cross protective immune response against both Influenza B lineages, Yamagata and Victoria. In some embodiments, engineered HA polypeptides as described herein may be used alone or in combination with other influenza antigens. In some embodiments, engineered HA polypeptides of the present invention may be used as a component of seasonal influenza vaccines or as part of influenza vaccination regimens intended to confer long-lasting, multi-season protection.

Various techniques may be used to obtain, align and select influenza sequences for each epitope or antigenic region. For example, Principal Components Analysis (PCA) is a common technique for working with high dimensional data and highlighting patterns in the data (i.e. it can be used to simplify large datasets and facilitate data exploration and visualization). Applied to biological sequences (proteins, genes), the technique enables comparison of thousands of sequences and the identification of groups of similar sequences based on a measure of sequence dissimilarity (Hamming distance, percent identity, percent similarity, surface accessibility, etc.). In the case of Human influenza viruses, influenza antigen protein sequences may be obtained from all publicly available amino acid sequences including, but not limited to, those available HA or NA amino acid sequences in the NCBI Influenza Virus Resource database. In some embodiments, more than 100, 500, 1000, 2000, 3000, 4000, 5000, 6000, 7000, 8000, 9000, 10,000, 12,000, 14,000, or 15,000 HA or NA amino acid sequences from multiple circulating influenza strains are obtained. In some embodiments, 100-5000, 100-6000, 100-7000, 100-8000, 100-9000, 100-10,000, 100-15,000, or 100-20,000 HA or NA amino acid sequences from multiple circulating influenza strains are obtained.

In some embodiments, HA or NA protein sequences are obtained from more than 5, 10, 15, 20, 25, 30, 35, 40, 45, 50, 60, 70, 80, 90 or 100 circulating influenza strains. In some embodiments, HA or NA amino acid sequences utilized in the present invention are obtained of a particular type and/or subtype of influenza virus. For example, HA or NA amino acid sequences may be obtained from a type A influenza virus. In some embodiments, the HA protein of an influenza A virus is selected from subtypes H1, H2, H3, H4, H5, H6, H7, H8, H9, H10, H11, H12, H13, H14, H15, or H16. In some embodiments, the influenza virus is selected from the group consisting of H1N1, H3N2, H5N1, and H7N9. In some embodiments, the type A virus is a seasonal strain, such as, /Texas/36/1991, A/Singapore/1986, A/New Caledonia/20/1999, A/Solomon Islands/03/2006, A/Brisbane/59/2007, or A/Wisconsin/67/2005. In some embodiments, the type A virus is a pandemic strain such as A/California/07/2009, A/California/04/2009, A/Belgium/145/2009, A/South Carolina/01/1918, or A/New Jersey/1976.

In some embodiments, HA or NA amino acid sequences may be obtained from a type B influenza virus. For example, the influenza B virus is a Yamagata lineage strain. In some embodiments, the influenza B virus is a Victoria lineage strain. In some embodiments, HA or NA amino acid sequences are obtained from an influenza B virus such as B/Hong Kong/330/2001, B/Hong Kong/05/1972, B/Lee/40, B/Massachusetts/02/2012, B/Panama/45/1990, B/Singapore/222/79, B/Victoria/02/1987, B/Yamagata/16/1988, or B/Brisbane/60/2008.

Typically, HA or NA amino acid sequences are trimmed to remove signal peptides, transmembrane regions and cytoplasmic tails, and the resulting ectodomain sequences are aligned. In some embodiments, redundant sequences are removed before alignment by screening the HA or NA amino acid sequences for those with 100%, or greater than 99.9%, 99% 98%, 97%, or 96% sequence identity, sequence identity, and removing all but one of the redundant sequences.

Visualization of principal components may be used to identify patterns associated with influenza B hemagglutinins including the two influenza B lineages (Yamagata vs Victoria). Additionally, sequences form distinct clusters based on similarity.

Modifications designed into the engineered HAs or NAs is deduced from an in silico analysis of sequence variation in both past and current circulating influenza strains. This analysis includes mapping antigenic and epitope patterns as well as structural modeling of the HA or NA protein. Targeted changes are subsequently introduced at corresponding amino acid residue locations and/or specific regions of the protein with known immune profiles in order to yield novel influenza B HA or NA polypeptides that would be reactive across the sequence clusters.

Each novel mosaic design is composed of multiple neutralizing HA or NA B-cell epitope patterns derived from antigenically diverse influenza B strains (including both Yamagata and Victoria lineages). The mosaic pattern of B-cell epitopes is assembled onto a backbone hemagglutinin or neuraminidase sequence. As non-limiting examples, suitable backbone hemagglutinin or neuraminidase sequences may be derived from: B/Hong Kong/330/2001, B/Hong Kong/05/1972, B/Lee/40, B/Massachusetts/02/2012, B/Panama/45/1990, B/Singapore/222/79, B/Victoria/02/1987, B/Yamagata/16/1988, B/Brisbane/60/2008. However, other backbone sequences could also be contemplated for this invention. The selected backbone provides the inter-epitope sequence of the engineered construct as well as the signal peptide and transmembrane domains required for full-length hemagglutinin molecules that are expressed and functional.

Exemplary SMARt Workflows

Figure 2:
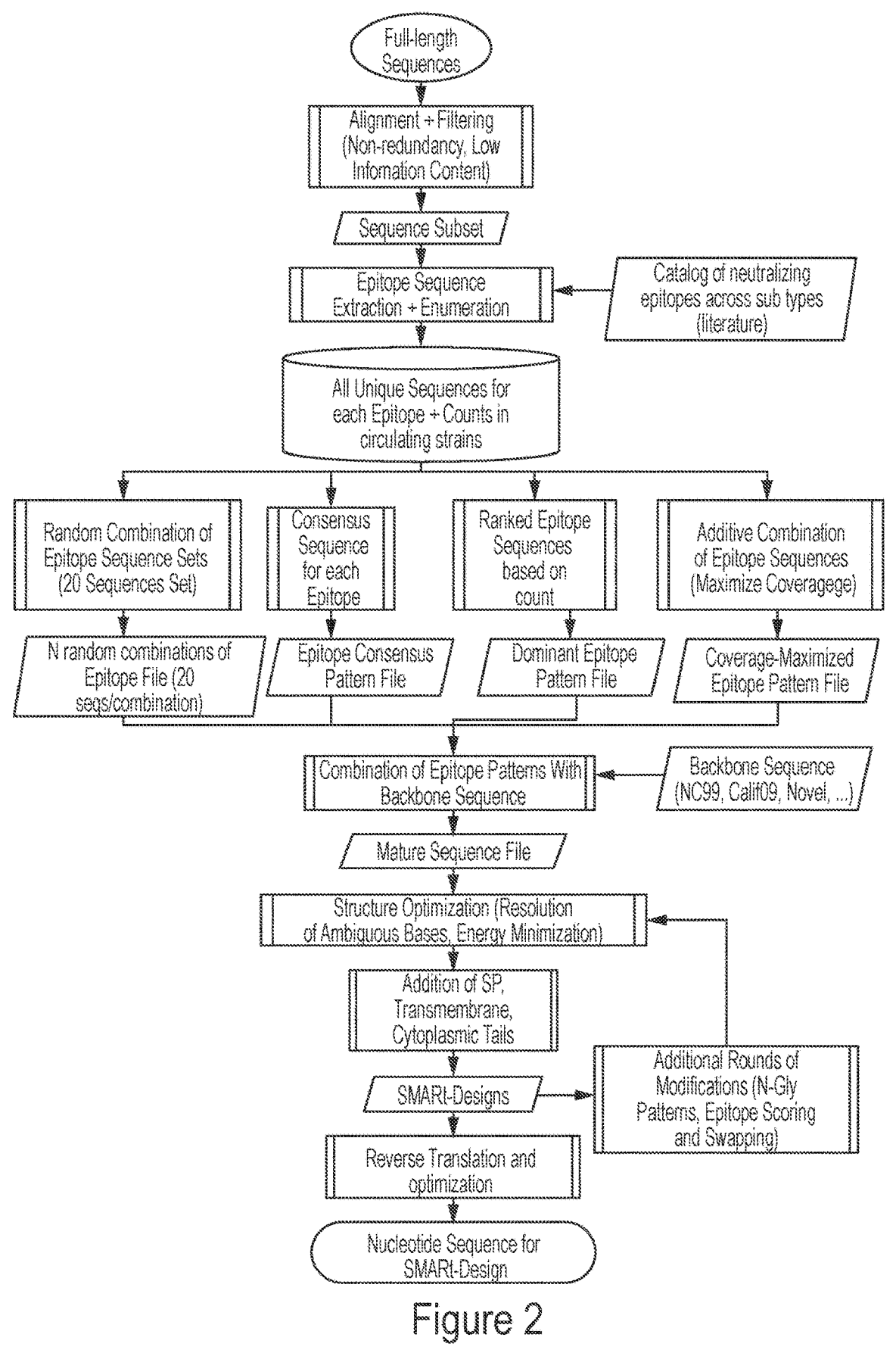

Briefly, known neutralizing and non-neutralizing hemagglutinin B-cell epitopes described for any influenza A and B virus are mapped to corresponding regions of Influenza B HA or NA. Individual sequences for each mapped B-cell epitope site are extracted and enumerated from the sequences of all available circulating Influenza B strains to generate an 'antigenic repertoire'. Individual sequences corresponding to different antigenic regions of HA or NA can be selected (or, alternatively, distilled into a consensus sequence) from the antigenic repertoire for each mapped epitope site and combined into novel mosaic pattern antigens (for example, epitope site 1 from circulating strain X, epitope site 2 from circulating strain Y, epitope site 3 from circulating strain Z, etc.) on a particular backbone strain, wherein the combination may be chosen or selected to elicit a particular immune response. Four distinct SMARt workflows are developed to combine antigenic repertoires into novel mosaic hemagglutinin molecules that are distinct from natural circulating strains. An overview of the compiled SMARt workflow is presented in FIG. 2.

Four non-limiting exemplary SMARt workflows are:

1. SMARt Random: B-cell epitope sequences for each of the mapped epitope sites are combined at random (drawn from all unique sequences for each epitope site in the antigenic repertoire). The resulting random combinations are scored for coverage of naturally occurring strains (by year, geography, and sequence coverage) and the highest scoring combinations are selected. The highest scoring selections based on breadth of coverage across naturally occurring strains by year, geography and sequence cluster are then combined with one a backbone sequence 2. SMARt Choice: Unique epitope sequences for each mapped epitope site are combined using an algorithm to maximize breadth of coverage across naturally occurring strains. An initial seed epitope is selected, and for each additional epitope added to the mosaic, a sequence is selected from the antigenic repertoire of the site that maximizes the breadth of coverage (i.e. as many naturally occurring strains as possible matched by at least one epitope). The highest scoring selections based on breadth of coverage across naturally occurring strains by year, geography and sequence cluster are then combined into one backbone sequence 3. SMARt Collapsed: A consensus sequence for each epitope is defined from the unique antigenic repertoire for that epitope site. The consensus sequences for each distinct epitope site are combined into a single mosaic pattern for the antigen and merged into a backbone sequence. This approach determines the consensus of unique epitope sequences for all epitope sites, combines the epitope consensus sequence into a mosaic pattern template, and combines the mosaic pattern template with desired backbone sequence(s).

The collapsed epitopes approach generates a single sequence for each mapped epitope site in the mosaic using a consensus approach. The unique amino acid residues comprising epitope sequences are identified from the antigenic repertoire. The most common amino acid at a given position for each mapped epitope site is used in the mosaic template pattern. The data flow and method steps are overviewed in FIG. 3. An upper case letter is used for residues that occur in 75$^+$% of the unique epitope patterns; otherwise a lower case letter is used. The "collapse_epitopes" step takes as input the epitopes and columns files. This step also integrates an ordered list of epitope names that specify the processing order for epitopes to be added to the mosaic template sequence. The program generates a FASTA formatted mosaic template sequence named "_collapsed_". The merge_seqs step replaces gap characters in the mosaic template sequence with the corresponding residue from the backbone sequence.

4. SMARt Dominant: For each epitope the unique sequences are ordered by their dominance as determined by the number of naturally occurring strains represented by that sequence. Dominant sequences for each epitope are selected and grafted onto a backbone in decreasing order of dominance (i.e. most dominant epitope patterns, then the second most dominant patterns, and so on). The SMARt Dominant approach generates polyvalent B-cell vaccine proteins using the occurrence frequency of unique epitope sequences to generate the mosaic sequences. In this approach, the unique epitope sequences for each epitope are ordered by frequency in the alignment. For M vaccine proteins, the top M unique epitope sequences for each epitope site are included in the mosaic pattern.

Figure 4:
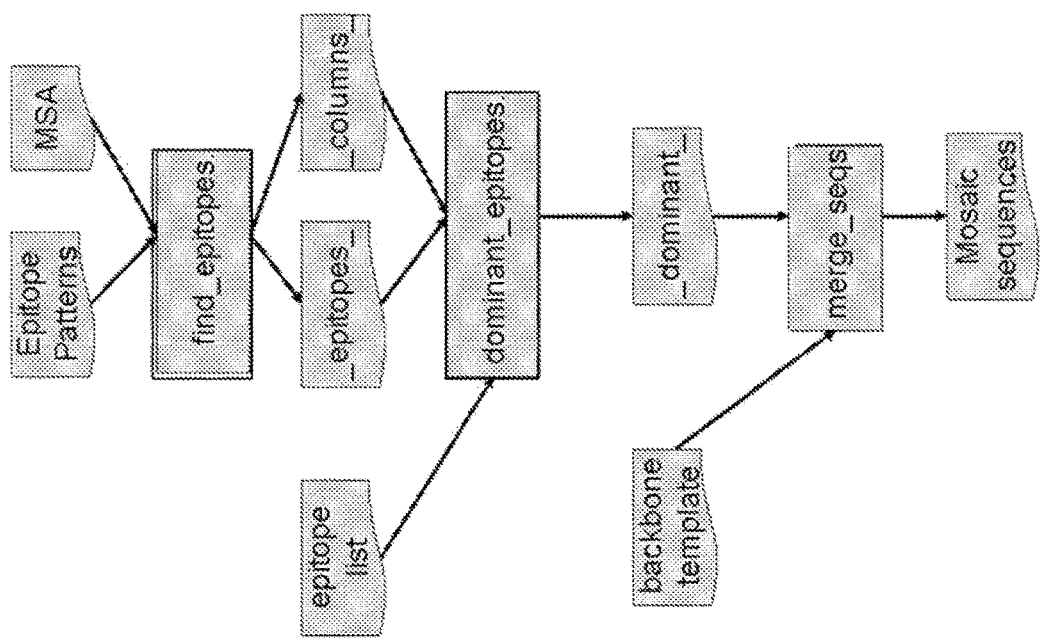
FIG. 4 shows an exemplary flowchart for the design and production of engineered antigenic polypeptides using the dominant epitopes process.

The dominant epitopes mosaic sequences approach generates a set of mosaic patterns by taking the occurrence frequency ordered epitope sequences for layering into the mosaic sequence templates. The data flow and method steps are overviewed in FIG. 4. The step "dominant_epitopesI" takes as input the epitopes and columns files generated at the "find_epitopes_msa" step. An additional input specifies the ordered list of epitope names for the processing order of epitopes to be added to the mosaic template sequences. This approach generates a FASTA formatted mosaic template file named "_dominant_".

Embodiments of the present invention are based on the application of a methodology for the generation of mosaic B cell epitope sequences through structural mapping of antigenic repertoires. Vaccines developed to target specific viral isolates may not protect against infection from different isolates of the same virus. The approach for developing broadly protective antigens of the present invention, in some embodiments, creates polyvalent mosaic sequences that include B cell epitopes from as many viral isolates as possible. The individual sequences of known neutralizing antibody epitopes and antigenic sites are recombined to generate mosaic antigens. The best mosaic sequence templates are selected by evaluating overall alignment coverage by geographic regions, viral isolate years, sequence clusters or other scoring methods. The selected set of mosaic template patterns are combined with target backbone sequences to generate a set of full-length mosaic protein antigens. In some embodiments, structure refinement of these mosaic sequences yields the final set of vaccination proteins.

In some embodiments, the present invention is based on combinations of neutralizing and non-neutralizing hemagglutinin B cell epitope sequences derived from multiple influenza B type strains to generate novel mosaic designs for influenza hemagglutinin. Each design, consisting of a mosaic pattern of B-cell epitopes, is combined with a backbone hemagglutinin sequence. For example, backbone hemagglutinin sequences derived from B/Massachusetts/02/2012, B/Panama/45/1990, B/Singapore/222/79, or B/Brisbane/60/2008 are used in some embodiments. Other hemagglutinin backbone sequences may also be employed for construction of engineered HA polypeptides according to the present invention. In some embodiments, a backbone sequence provides the inter-epitope sequence as well as the signal peptide and transmembrane domains required for full-length hemagglutinin molecules that are expressed and functional.

In general, known neutralizing and non-neutralizing hemagglutinin B-cell epitopes described for any influenza B lineage strain are mapped to corresponding regions of the HA backbone. Individual sequences (antigenic repertoires) for each B cell epitopes are extracted and enumerated from the sequences of all available circulating influenza B strains. Distinct workflows, as described above, have been developed to combine the antigenic repertoires into novel mosaic hemagglutinin molecules that are distinct from natural circulating strains.

Exemplary workflows are further described in the Examples below. Although hemagglutinin polypeptides are used as examples to illustrate methods described herein, the present invention may be used to engineer neuraminidase (NA) polypeptides and other immunogenic polypeptides or therapeutic biologics.

Exemplary Mosaic Sequence Patterns and Engineered HA Polypeptides

The approaches described herein provide mosaic sequence patterns or consensus sequences that define overlapping or non-overlapping epitopes or antigenic regions. Desired epitopes or antigenic regions may be linear or discontinuous based on 3D structures including, but not limited to, antigenic regions (e.g., BA, BB1, BB2, BC, BD, BE, etc.) and/or antibody binding sites.

In some embodiments, the epitope or antigenic region is all or part of the Receptor Binding Site (RBS). As used herein, the term "receptor-binding site" or "RBS" comprises contiguous or non-contiguous amino acid residues of the head region of an influenza HA polypeptide, which include amino acids involved in direct binding of sialic acids on the target cell receptor proteins. The region of HA responsible for receptor binding resides at the membrane-distal tip of each monomer of the HA trimer, and it has several main structural features. For example, the binding site is flanked by the "220 and 130 loops", which contain amino acids that interact with sialic acid or internal sugars of the glycan chain. The membrane-distal region of the site is formed by the 190 helix, which also includes residues with the potential to contact the receptor at either the sialic acid (residue 194) or internal glycans on the receptor (approximately residues 190 and 193). The base of the site contains several highly conserved residues that form an extensive hydrogen bond network. Amino acid residues that make up a "receptor-binding site" or "RBS" of an influenza HA polypeptide may be described from a three-dimensional crystal structures of HA polypeptides complexed with sialic acid analogs and identifying amino acid residues within a certain proximity to the analog or may be described in reference to an HA polypeptide sequence from a particular viral strain (e.g., A/New Caledonia/20/99 or A/California/07/2009). Thus, in some embodiments, the "receptor-binding site" or "RBS" of an engineered HA polypeptide as described herein may be determined using a reference HA polypeptide sequence. In some embodiments, the "receptor-binding site" or "RBS" of an engineered HA polypeptide as described herein may be determined using the crystal structures of HA polypeptide sequence in complex with human and avian receptor analogs (ex. LSTa, LSTc). An exemplary reference crystal structure of HA polypeptide sequence in complex with LSTc includes A/Puerto Rico/8/1934 (H1N1) pdb|1RVZ. In some embodiments, the RBS may be defined as the epitope bound by the broadly neutralizing monoclonal antibody CH65 (see, e.g., Whittle J R, et al. *Broadly neutralizing human antibody that recognizes the receptor-binding pocket of influenza virus hemagglutinin*. Proc Natl Acad Sci USA. 2011; 108:14216-21). Alternatively or additionally, the RBS may be defined as an area including all amino acid residues within 15 Angstroms of a universally conserved tryptophan corresponding to position 167 in (CA09 09 Numbering) (e.g. see Xu, R et al. Nat Struct Mol Biol. 2013 March; 20(3):363-70) or corresponding position on a influenza type B virus HA polypeptide. An exemplary reference crystal structure of influenza type B HA polypeptide sequence includes B/Brisbane/60/2008 pdb|4FQM. The corresponding tryptophan is residue 173 in the full-length sequence and 158 in the crystal structure 4FQM.

In various embodiments, an engineered HA polypeptide as described herein comprises an antigenic region that comprises contiguous or non-contiguous amino acid residues associated with, adjacent to, and/or encompass a receptor-binding site (RBS). In some embodiments, the non-contiguous amino acid residues can be determined using the crystal structures of HA polypeptide. An exemplary reference crystal structure of HA polypeptide sequence includes B/Yamanashi/166/1998 pdb|4M40.

In some embodiments, an RBS site comprises a mosaic sequence pattern that comprises amino acid substitutions at residues: 110, 140, 141, 143, 145, 146, 153, 154, 155, 156, 165, 174, 175, 176, 177, 179, 180, 181, 209, 210, 211, 212, 215, 216, 217, 228, 258, 259, and/or 279 or a subset thereof, (e.g., with at least 30%, 40%, 50%, 60%, 70%, 75%, 80%, 85%, 90%, or 95% of the referenced residues, or at least 3, 4, 5, 6, 7, 8, 9, or 10 referenced residues), as indexed by reference to a B/Brisbane/60/2008 amino acid sequence.

In some embodiments, an RBS site comprises a mosaic sequence pattern that comprises amino acid substitutions at residues: 110F, 140I, 141D/N, 143E, 145A, 146P, 153G, 154T, 155S, 156G/R, 165S/I/N, 174A, 175V, 176P, 177K, 179D, 180N/S, 181N, 209H, 210S, 211D, 212N/D, 215Q, 216M, 217K/V, 228F, 258S, 259G, and/or 279Q, or a subset thereof, (e.g., with at least 30%, 40%, 50%, 60%, 70%, 75%, 80%, 85%, 90%, or 95% of the referenced residues, or at least 3, 4, 5, 6, 7, 8, 9, or 10 referenced residues), as indexed by reference to a B/Brisbane/60/2008 amino acid sequence.

In some embodiments, a mosaic sequence pattern comprises amino acid substitutions at residues: 21, 22, 23, 26, 37, 38, 43, 45, 46, 47, 52, 53, 54, 55, 56, 58, 60, 62, 63, 67, 70, 73, 74, 75, 76, 77, 85, 86, 89, 90, 91, 92, 93, 94, 95, 100, 101, 102, 103, 104, 105, and/or 106, or a subset thereof (e.g., with at least 30%, 40%, 50%, 60%, 70%, 75%, 80%, 85%, 90%, or 95% of the referenced residues, or at least 3, 4, 5, 6, 7, 8, 9, or 10 referenced residues), as indexed by reference to a B/Brisbane/60/2008 HA amino acid sequence.

In some embodiments, a mosaic sequence pattern that comprises amino acid residues: 21G, 22I, 23T, 26N/K, 37G, 38E, 43G, 45I, 46P/S, 47L, 52T, 53K, 54S, 55Y/H, 56F, 58N, 60K/R, 62T, 63E/K, 67K, 70P, 73L/P, 74N, 75C, 76T, 77D, 85P, 86K/M, 89G, 90K/TN, 91I, 92P, 93S, 94A, 95R/K, 100H, 101E, 102V, 103R, 104P, 105V, and/or 106T, or a subset thereof (e.g., with at least 30%, 40%, 50%, 60%, 70%, 75%, 80%, 85%, 90%, or 95% of the referenced residues, or at least 3, 4, 5, 6, 7, 8, 9, or 10 referenced residues), as indexed by reference to a B/Brisbane/60/2008 HA amino acid sequence.

In some embodiments, a mosaic sequence pattern that comprises amino acid substitutions at residues: 128, 130, 131, 133, 136, 137, 138, 159, 160, 161, 162, 165, 173, 195, 196, 197, 198, 199, 200, 213, 214, 225, 227, 245, 248, 250, 251, 257, and/or 277 or a subset thereof (e.g., with at least 30%, 40%, 50%, 60%, 70%, 75%, 80%, 85%, 90%, or 95% of the referenced residues, or at least 3, 4, 5, 6, 7, 8, 9, or 10 referenced residues), as indexed by reference to a B/Brisbane/60/2008 HA amino acid sequence.

In some embodiments, a mosaic sequence pattern that comprises amino acid residues: 128G, 130E, 131H, 133R, 136T/N, 137Q/H/Y, 138N, 159P, 160N, 161A/V, 162T, 165K/R, 173W, 195I, 196C, 197T/A, 198E, 199G, 200E, 213K, 214T, 225P, 227K, 245G/D, 248D/N, 250T, 251E, 257Q, and/or 277V/T or a subset thereof (e.g., with at least 30%, 40%, 50%, 60%, 70%, 75%, 80%, 85%, 90%, or 95% of the referenced residues, or at least 3, 4, 5, 6, 7, 8, 9, or 10 referenced residues), as indexed by reference to a B/Brisbane/60/2008 HA amino acid sequence.

In some embodiments, a mosaic sequence pattern that comprises amino acid residues: 290, 300, 301, 302, 303, 304, 305, 306, 307, 308, 309, 314, 315, 319, 320, 321, 322, 323, 348, 354, 355, 356, 377, 378, 380, 381, 382, 383, 387, 392, 394, 395, 396, 397, 398, 400, 401, 403, 404, 405, 406, 407, 408, 410, 411, 412, 413, 414, 415, 417, 418, 419, 420, 421, 422, 470, 508, and/or 512, or a subset thereof (e.g., with at least 30%, 40%, 50%, 60%, 70%, 75%, 80%, 85%, 90%, or 95% of the referenced residues, or at least 3, 4, 5, 6, 7, 8, 9, or 10 referenced residues), as indexed by reference to a B/Brisbane/60/2008 HA amino acid sequence.

In some embodiments, a mosaic sequence pattern that comprises amino acid substitutions at residues: 290C, 300G, 301S/T, 302L, 303P, 304L, 305I, 306G, 307E, 308A, 309D, 314K, 315Y, 319N, 320K, 321S, 322K, 323P, 348N, 354P, 355P, 356A/T, 377E, 378G, 380V/I, 381A, 382G, 383W, 387T, 392H, 394V, 395A, 396V, 397A, 398A, 400L, 401K, 403T, 404Q, 405E, 406A, 407I, 408N, 410I, 411T, 412K, 413N, 414L, 415N, 417L, 418S, 419E, 420L, 421E, 422I, 470I, 508Q, and/or 512D/N, or a subset thereof, (e.g., with at least 30%, 40%, 50%, 60%, 70%, 75%, 80%, 85%, 90%, or 95% of the referenced residues, or at least 3, 4, 5, 6, 7, 8, 9, 10, 15, or 20 referenced residues), as indexed by reference to a B/Brisbane/60/2008 HA amino acid sequence.

In some embodiments, a mosaic sequence pattern or consensus sequence according to the invention comprises residues: 110F, 140I, 141N, 143E, 145A, 146P, 153G, 154T, 155S, 156G, 165S, 174A, 175V, 176P, 177K, 179D, 180N, 181N, 209H, 210S, 211D, 212N, 215Q, 216M, 217K, 228F, 258S, 259G, 279Q, 21G, 22I, 23T, 26N, 37G, 38E, 43G, 451, 46P, 47L, 52T, 53K, 54S, 55H, 56F, 58N, 60K, 62T, 63E, 67K, 70P, 73L, 74N, 75C, 76T, 77D, 85P, 86K, 89G, 90K, 91I, 92P, 93S, 94A, 95K, 100H, 101E, 102V, 103R, 104P, 105V, 106T, 128G, 130E, 131H, 133R, 136T, 137Q, 138N, 159P, 160N, 161A, 162T, 165K, 173W, 195I, 196C, 197T, 198E, 199G, 200E, 213K, 214T, 225P, 227K, 245G, 248N, 250T, 251E, 257Q, 277V, 290C, 300G, 301S, 302L, 303P, 304L, 3051, 306G, 307E, 308A, 309D, 314K, 315Y, 319N, 320K, 321S, 322K, 323P, 348N, 354P, 355P, 356A, 377E, 378G, 380I, 381A, 382G, 383W, 387T, 392H, 394V, 395A, 396V, 397A, 398A, 400L, 401K, 403T, 404Q, 405E, 406A, 407I, 408N, 410I, 411T, 412K, 413N, 414L, 415N, 417L, 418S, 419E, 420L, 421E, 422V, 470I, 508Q, and/or 512D, or a subset thereof (e.g., with at least 10%, 20%, 30%, 40%, 50%, 60%, 70%, 75%, 80%, 85%, 90%, 95%, 98% of the referenced residues, or at least 3, 4, 5, 6, 7, 8, 9, 10, 15, 20, 25, 30, 35, 40, 45, or 50 referenced residues), as indexed by reference to a B/Brisbane/60/2008 HA amino acid sequence.

In some embodiments, a mosaic sequence pattern or consensus sequence according to the invention comprises residues: 110F, 140I, 141D, 143E, 145A, 146P, 153G, 154T, 155S, 156G, 165S, 174A, 175V, 176P, 177K, 179D, 180N, 181N, 209H, 210S, 211D, 212N, 215Q, 216M, 217K, 228F, 258S, 259G, 279Q, 21G, 22I, 23T, 26N, 37G, 38E, 43G, 451, 46P, 47L, 52T, 53K, 54S, 55Y, 56F, 58N, 60K, 62T, 63E, 67K, 70P, 73L, 74N, 75C, 76T, 77D, 85P, 86K, 89G, 90K, 91I, 92P, 93S, 94A, 95K, 100H, 101E, 102V, 103R, 104P, 105V, 106T, 128G, 130E, 131H, 133R, 136T, 137Q, 138N, 159P, 160N, 161A, 162T, 165K, 173W, 195I, 196C, 197T, 198E, 199G, 200E, 213K, 214T, 225P, 227K, 245G, 248N, 250T, 251E, 257Q, 277V 290C, 300G, 301S, 302L, 303P, 304L, 3051, 306G, 307E, 308A, 309D, 314K, 315Y, 319N, 320K, 321S, 322K, 323P, 348N, 354P, 355P, 356A, 377E, 378G, 380V, 381A, 382G, 383W, 387T, 392H, 394V, 395A, 396V, 397A, 398A, 400L, 401K, 403T, 404Q, 405E, 406A, 407I, 408N, 410I, 411T, 412K, 413N, 414L, 415N, 417L, 418S, 419E, 420L, 421E, 422I, 470I, 508Q, and/or 512D, or a subset thereof or a subset thereof (e.g., with at least 10%, 20%, 30%, 40%, 50%, 60%, 70%, 75%, 80%, 85%, 90%, 95%, 98% of the referenced residues, or at least 3, 4, 5, 6, 7, 8, 9, 10, 15, 20, 25, 30, 35, 40, 45, or 50 referenced residues), as indexed by reference to a B/Brisbane/60/2008 HA amino acid sequence.

In some embodiments, a mosaic sequence pattern or consensus sequence according to the invention comprises residues: 110F, 140I, 141D, 143E, 145A, 146P, 153G, 154T, 155S, 156G, 165S, 174A, 175V, 176P, 177K, 179D, 180N, 181N, 209H, 210S, 211D, 212N, 215Q, 216M, 217K, 228F, 258S, 259G, 279Q, 21G, 22I, 23T, 26N, 37G, 38E, 43G, 451, 46P, 47L, 52T, 53K, 54S, 55Y, 56F, 58N, 60K, 62T, 63E, 67K, 70P, 73L, 74N, 75C, 76T, 77D, 85P, 86K, 89G, 90K, 91I, 92P, 93S, 94A, 95K, 100H, 101E, 102V, 103R, 104P, 105V, 106T, 128G, 130E, 131H, 133R, 136T, 137Q, 138N, 159P, 160N, 161A, 162T, 165K, 173W, 195I, 196C, 197T, 198E, 199G, 200E, 213K, 214T, 225P, 227K, 245G, 248N, 250T, 251E, 257Q, 277V 290C, 300G, 301S, 302L, 303P, 304L, 3051, 306G, 307E, 308A, 309D, 314K, 315Y, 319N, 320K, 321S, 322K, 323P, 348N, 354P, 355P, 356A, 377E, 378G, 380V, 381A, 382G, 383W, 387T, 392H, 394V, 395A, 396V, 397A, 398A, 400L, 401K, 403T, 404Q, 405E, 406A, 407I, 408N, 410I, 411T, 412K, 413N, 414L, 415N, 417L, 418S, 419E, 420L, 421E, 422I, 470I, 508Q, and/or 512D, or a subset thereof or a subset thereof (e.g., with at least 10%, 20%, 30%, 40%, 50%, 60%, 70%, 75%, 80%, 85%, 90%, 95%, 98% of the referenced residues, or at least 3, 4, 5, 6, 7, 8, 9, 10, 15, 20, 25, 30, 35, 40, 45, or 50 referenced residues), as indexed by reference to a B/Brisbane/60/2008 HA amino acid sequence.

In some embodiments, a mosaic sequence pattern or consensus sequence according to the invention comprises residues: 110F, 140I, 141D, 143E, 145A, 146P, 153G, 154T, 155S, 156R, 165S, 174A, 175V, 176P, 177K, 179D, 180S, 181N, 209H, 210S, 211D, 212N, 215Q, 216M, 217V, 228F, 258S, 259G, 279Q, 21G, 22I, 23T, 26N, 37G, 38E, 43G, 451, 46P, 47L, 52T, 53K, 54S, 55H, 56F, 58N, 60R, 62T, 63K, 67K, 70P, 73L, 74N, 75C, 76T, 77D, 85P, 86K, 89G, 90N, 91T, 92P, 93S, 94A, 95K, 100H, 101E, 102V, 103R, 104P, 105V, 106T, 128G, 130E, 131H, 133R, 136N, 137Y, 138N, 159P, 160N, 161V, 162T, 165R, 173W, 195I, 196C, 197T, 198E, 199G, 200E, 213K, 214T, 225P, 227K, 245D, 248N, 250T, 251E, 257Q, 277T, 290C, 300G, 301T, 302L, 303P, 304L, 3051, 306G, 307E, 308, 309D, 314K, 315Y, 319N, 320K, 321S, 322K, 323P, 348N, 354P, 355P, 356A, 377E, 378G, 380I, 381A, 382G, 383W, 387T, 392H, 394V, 395A, 396V, 397A, 398A, 400L, 401K, 403T, 404Q, 405E, 406A, 407I, 408N, 410I, 411T, 412K, 413N, 414L, 415N, 417L, 418S, 419E, 420L, 421E, 422V, 470I, 508Q, and/or 512D, or a subset thereof (e.g., with at least 10%, 20%, 30%, 40%, 50%, 60%, 70%, 75%, 80%, 85%, 90%, 95%, 98% of the referenced residues, or at least 3, 4, 5, 6, 7, 8, 9, 10, 15, 20, 25, 30, 35, 40, 45, or 50 referenced residues), as indexed by reference to a B/Panama/45/1990 HA amino acid sequence.

In some embodiments, an engineered HA polypeptide of the present invention comprises an antigenic region that comprises amino acid residues 110F, 140I, 141N, 143E, 145A, 146P, 153G, 154T, 155S, 156G, 165N, 174A, 175V, 176P, 177K, 179D, 180N, 181N, 209H, 210S, 211D, 212N, 215Q, 216M, 217K, 228F, 258S, 259G, 279Q, 21G, 22I, 23T, 26N, 37G, 38E, 43G, 451, 46P, 47L, 52T, 53K, 54S, 55Y, 56F, 58N, 60K, 62T, 63K, 67K, 70P, 73L, 74N, 75C, 76T, 77D, 85P, 86M, 89G, 90T, 91I, 92P, 93S, 94A, 95K, 100H, 101E, 102V, 103R, 104P, 105V, 106T, 128G, 130E, 131N, 133R, 136T, 137H, 138N, 159P, 160N, 161A, 162T, 165K, 173W, 195I, 196C, 197T, 198E, 199G, 200E, 213K, 214T, 225P, 227K, 245G, 248D, 250T, 251E, 257Q, 277T, 290C, 300G, 301S, 302L, 303P, 304L, 3051, 306G, 307E, 308A, 309D, 314K, 315Y, 319N, 320K, 321S, 322K, 323P, 348N, 354P, 355P, 356A, 377E, 378G, 380I, 381A, 382G, 383W, 387T, 392H, 394V, 395A, 396V, 397A, 398A, 400L, 401K, 403T, 404Q, 405E, 406A, 407I, 408N, 410I, 411T, 412K, 413N, 414L, 415N, 417L, 418S, 419E, 420L, 421E, 422V, 470I, 508Q, and/or 512D, or a subset thereof (e.g., with at least 10%, 20%, 30%, 40%, 50%, 60%, 70%, 75%, 80%, 85%, 90%, 95%, 98% of the referenced residues, or at least 3, 4, 5, 6, 7, 8, 9, 10, 15, 20, 25, 30, 35, 40, 45, or 50 referenced residues), as indexed by reference to a, B/Massachusetts/02/2012 amino acid sequence.

Exemplary mosaic amino acid sequence patterns based on different SMARt workflows (e.g., SMARt dominant (DO), SMARt Random (RA), SMARt Collapse (CO), or SMARt Choice (CI)) are provided in Table 1.

TABLE 1

|    | DO2 | DO3 | CO1 | RA82 | RA103 |
|----|-----|-----|-----|------|-------|
| 21 | G   | G   | G   | G    | G     |
| 22 | I   | I   | I   | I    | I     |
| 23 | T   | T   | T   | T    | T     |
| 26 | N   | N   | N   | K    | N     |

TABLE 1-continued

|  | DO2 | DO3 | CO1 | RA82 | RA103 |
|---|---|---|---|---|---|
| 37 | G | G | G | G | G |
| 38 | E | E | E | E | E |
| 43 | G | G | G | G | G |
| 45 | I | I | I | I | I |
| 46 | P | S | P | P | P |
| 47 | L | L | L | L | L |
| 52 | T | T | T | T | T |
| 53 | K | K | K | K | K |
| 54 | S | S | S | S | S |
| 55 | Y | H | H | H | Y |
| 56 | F | F | F | F | F |
| 58 | N | N | N | N | N |
| 60 | K | K | K | R | K |
| 62 | T | T | T | T | T |
| 63 | E | K | E | K | K |
| 67 | K | K | K | K | K |
| 70 | P | P | P | P | P |
| 73 | L | P | L | L | L |
| 74 | N | N | N | N | N |
| 75 | C | C | C | C | C |
| 76 | T | T | T | T | T |
| 77 | D | D | D | D | D |
| 85 | P | P | P | P | P |
| 86 | K | M | K | K | M |
| 89 | G | G | G | G | G |
| 90 | K | T | K | N | T |
| 91 | I | I | I | T | I |
| 92 | P | P | P | P | P |
| 93 | S | S | S | S | S |
| 94 | A | A | A | A | A |
| 95 | K | K | R | K | K |
| 100 | H | H | H | H | H |
| 101 | E | E | E | E | E |
| 102 | V | V | V | V | V |
| 103 | R | R | R | R | R |
| 104 | P | P | P | P | P |
| 105 | V | V | V | V | V |
| 106 | T | T | T | T | T |
| 110 | F | F | F | F | F |
| 128 | G | G | G | G | G |
| 130 | E | E | E | E | E |
| 131 | H | H | H | H | N |
| 133 | R | R | R | R | R |
| 136 | T | T | T | N | T |
| 137 | Q | H | Q | Y | H |
| 138 | N | N | N | N | N |
| 140 | I | I | I | I | I |
| 141 | D | N | N | D | N |
| 143 | E | E | E | E | E |
| 145 | A | A | A | A | A |
| 146 | P | P | P | P | P |
| 153 | G | G | G | G | G |
| 154 | T | T | T | T | T |
| 155 | S | S | S | S | S |
| 156 | G | G | G | R | G |
| 159 | P | P | P | P | P |
| 160 | N | N | N | N | N |
| 161 | A | A | A | V | A |
| 162 | T | T | T | T | T |
| 165 | S | I | S | S | N |
| 165 | K | K | K | R | K |
| 173 | W | W | W | W | W |
| 174 | A | A | A | A | A |
| 175 | V | V | V | V | V |
| 176 | P | P | P | P | P |
| 177 | K | K | K | K | K |
| 179 | D | D | D | D | D |
| 180 | N | N | N | S | N |
| 181 | N | N | N | N | N |
| 195 | I | I | I | I | I |
| 196 | C | C | C | C | C |
| 197 | T | A | T | T | T |
| 198 | E | E | E | E | E |
| 199 | G | G | G | G | G |
| 200 | E | E | E | E | E |
| 209 | H | H | H | H | H |
| 210 | S | S | S | S | S |
| 211 | D | D | D | D | D |
| 212 | N | D | N | N | N |
| 213 | K | K | K | K | K |
| 214 | T | T | T | T | T |
| 215 | Q | Q | Q | Q | Q |
| 216 | M | M | M | M | M |
| 217 | K | K | K | V | K |
| 225 | P | P | P | P | P |
| 227 | K | K | K | K | K |
| 228 | F | F | F | F | F |
| 245 | G | D | G | D | G |
| 248 | D | N | N | N | D |
| 250 | T | T | T | T | T |
| 251 | E | E | E | E | E |
| 257 | Q | Q | Q | Q | Q |
| 258 | S | S | S | S | S |
| 259 | G | G | G | G | G |
| 277 | V | T | V | T | T |
| 279 | Q | Q | Q | Q | Q |
| 290 | C | C | C | C | C |
| 300 | G | G | G | G | G |
| 301 | S | S | S | T | S |
| 302 | L | L | L | L | L |
| 303 | P | P | P | P | P |
| 304 | L | L | L | L | L |
| 305 | I | I | I | I | I |
| 306 | G | G | G | G | G |
| 307 | E | E | E | E | E |
| 308 | A | A | A | — | A |
| 309 | D | D | D | D | D |
| 314 | K | K | K | K | K |
| 315 | Y | Y | Y | Y | Y |
| 319 | N | N | N | N | N |
| 320 | K | K | K | K | K |
| 321 | S | S | S | S | S |
| 322 | K | K | K | K | K |
| 323 | P | P | P | P | P |
| 348 | N | N | N | N | N |
| 354 | P | P | P | P | P |
| 355 | P | P | P | P | P |
| 356 | A | T | A | A | A |
| 377 | E | E | E | E | E |
| 378 | G | G | G | G | G |
| 380 | V | I | I | I | I |
| 381 | A | A | A | A | A |
| 382 | G | G | G | G | G |
| 383 | W | W | W | W | W |
| 387 | T | T | T | T | T |
| 392 | H | H | H | H | H |
| 394 | V | V | V | V | V |
| 395 | A | A | A | A | A |
| 396 | V | V | V | V | V |
| 397 | A | A | A | A | A |
| 398 | A | A | A | A | A |
| 400 | L | L | L | L | L |
| 401 | K | K | K | K | K |
| 403 | T | T | T | T | T |
| 404 | Q | Q | Q | Q | Q |
| 405 | E | E | E | E | E |
| 406 | A | A | A | A | A |
| 407 | I | I | I | I | I |
| 408 | N | N | N | N | N |
| 410 | I | I | I | I | I |
| 411 | T | T | T | T | T |
| 412 | K | K | K | K | K |
| 413 | N | N | N | N | N |
| 414 | L | L | L | L | L |
| 415 | N | N | N | N | N |
| 417 | L | L | L | L | L |
| 418 | S | S | S | S | S |
| 419 | E | E | E | E | E |
| 420 | L | L | L | L | L |
| 421 | E | E | E | E | E |
| 422 | I | V | V | V | V |
| 470 | I | I | I | I | I |
| 508 | Q | Q | Q | Q | Q |
| 512 | D | N | D | D | D |

As non-limiting examples, full-length mosaic sequence patterns or consensus sequence templates are shown on Table 2. "-" shown in the templates on Table 2 stands for any amino acid or a peptide bond. The templates may be subsequently merged onto a backbone sequence to provide the missing sequence information.

TABLE 2

```
DO2_template    --------------------GIT--N----------GE----G-IPL----TKSYF-N-K-TE---
                K--P--LNCTD-------PK--GKIPSAK----HEVRPVT---F-----------------
                G-EH-R--TQN-ID-E-AP------GTSG--PNAT-KS-------WAVPK-
                DNN------------ICTEGE--------HSDNKTQMK-------P-KF-------------
                ---G--D-TE-----QSG---------KPG-----V-Q----------C---------
                GSLPLIGEAD----KY---NKSKP----------------------N-----PPA--------
                ------------EG-VAGW---T----H-VAVAA-LK-TQEAIN-ITKNLN-
                LSELEI----------------------------------------I------------------------
                -----------Q---D
                (SEQ ID NO: 1)

DO3_template    --------------------GIT--N----------GE----G-ISL----TKSHF-N-K-TK---
                K--P--PNCTD-------PM--GTIPSAK----HEVRPVT---F-----------------
                G-EH-R--THN-IN-E-AP------GTSG--PNAT-KI-------WAVPK-DNN-
                ------------ICAEGE--------HSDDKTQMK-------P-KF----------------D--
                N-TE-----QSG---------KPG-----T-Q----------C---------GSLPLIGEAD--
                --KY---NKSKP----------------------N-----PPT------------------EG-
                IAGW---T----H-VAVAA-LK-TQEAIN-ITKNLN-LSELEV------------
                ----------------------------------I-------------------------------------Q---N
                (SEQ ID NO: 2)

CO1_template    --------------------GIT--n----------GE----G-IPL----TKShF-N-K-Te---K--
                P--lNCTD-------Pk--GkiPSAr----HEVRPVT---F-----------------G-Eh-
                R--TqN-In-E-AP------GTSG--PNaT-ks-------WAVPK-DnN------------
                -ICtEGE--------HSDnktQMk-------P-KF----------------g--n-TE-----
                QSG---------KpG-----v-Q----------C---------GSLPLIGEAD----KY---
                NKSKP----------------------N-----PPA--------------------EG-IAGW---
                T----H-VAVAA-LK-TQEAIN-ITKNLN-LSELEV----------------------
                -----------------------I------------------------------Q---D
                (SEQ ID NO: 3)

RA82_template   --------------------GIT--K----------GE----G-IPL----TKSHF-N-R-TK---
                K--P--LNCTD-------PK--GNTPSAK----HEVRPVT---F-----------------
                G-EH-R--NYN-ID-E-AP------GTSR--PNVT-RS-------WAVPK-
                DSN------------ICTEGE--------HSDNKTQMV-------P-KF-------------
                --D--N-TE-----QSG---------KSG-----T-Q----------C---------
                GTLPLIGE-D----KY---NKSKP----------------------N-----PPA---------
                -----------EG-IAGW---T----H-VAVAA-LK-TQEAIN-ITKNLN-
                LSELV-----------------------------------------------I------------------------
                -------------Q---D
                (SEQ ID NO: 4)

RA103_template  --------------------GIT--N----------GE----G-IPL----TKSYF-N-K-TK---
                K--P--LNCTD-------PM--GTIPSAK----HEVRPVT---F-----------------
                G-EN-R--THN-IN-E-AP------GTSG--PNAT-KN-------WAVPK-
                DNN------------ICTEGE--------HSDNKTQMK-------P-KF-------------
                ---G--D-TE-----QSG---------KSG-----T-Q----------C---------
                GSLPLIGEAD----KY---NKSKP----------------------N-----PPA--------
                ------------EG-IAGW---T----H-VAVAA-LK-TQEAIN-ITKNLN-
                LSELV-----------------------------------------------I------------------------
                -----------Q---D
                (SEQ ID NO: 5)
```

Selected templates of mosaic sequence patterns or consensus sequences may be inserted into corresponding locations of a structural backbone of HA or NA to generate mosaic influenza HA or NA polypeptide. For example, one or more amino acid substitutions according to mosaic sequence patterns as shown in Table 1 may be inserted in various corresponding locations in a backbone sequence. In some embodiments, at least 10%, 20%, 30%, 40%, 50%, 60%, 70%, 75%, 80%, 85%, 90%, 95%, 98%, 99%, or 100% of the referenced residues as shown in Table 1 are inserted in corresponding locations in a backbone sequence. In some embodiments, at least 3, 4, 5, 6, 7, 8, 9, 10, 15, 20, 25, 30, 35, 40, 45, 50, 55, 60, 65, 70, 75, 80, 85, 90, 95, or 100 referenced residues shown in Table 1 are inserted in corresponding locations in a backbone sequence.

A suitable structural backbone may be derived from different lineages. For example, a suitable structural backbone may be derived form a Yamagata lineage or a victoria lineage. In the some embodiments, one of the following nine backbone hemagglutinin sequences may be used: B/Hong Kong/330/2001, B/Hong Kong/05/1972, B/Lee/40, B/Massachusetts/02/2012, B/Panama/45/1990, B/Singapore/222/79, B/Victoria/02/1987, B/Yamagata/16/1988, B/Brisbane/60/2008.

Exemplary backbone sequences are shown in Table 3.

TABLE 3

| | |
|---|---|
| 60780\|CAA25425\|<br>HA\|Human\|fluB\|<br>B/Singapore/222/<br>79\|Singapore\|1979\| | DRICTGITSSNSPHVVKTATQGEVNVTGVIPLTTTPTKSHFANL<br>KGTKTRGKLCPNCLNCTDLDVALGRPKCMGTIPSAKASILHEV<br>KPVTSGCFPIMHDRTKIRQLPNLLRGYENIRLSTRNVINAERAP<br>GGPYIIGTSGSCPNVTNGNGFFATMAWAVPKD-<br>NKTATNPLTVEVPYICTKGEDQITVWGFHSDTETQMVKLYGD<br>SKPQKFTSSANGVTTHYVSQIGGFPNQTEDGGLPQSGRIVVD<br>MVQKPGKTGTIVYQRGVLLPQKVWCASGRSKVIKGSLPLIGE<br>ADCLHEKYGGLNKSKPYYTGEHAKAIGNCPIWVKTPLKLANG<br>TKYRPPAKLLKERGFFGAIAGFLEGGWEGMIAGWHGYTSHGA<br>HGVAVAADLKSTQEAINKITKNLNSLSELEVKNLQRLSGAMD<br>ELHNEILELDEKVDDLRADTISSQIELAVLLSNEGIINSEDEHLL<br>ALERKLKKMLGPSAVDIGNGCFETKHKCNQTCLDRIAAGTFN<br>AGEFSLPTFDSLNITAASLNDDGLDNHTILLYYSTAASSLAVTL<br>MIAIFIVYMVSRDNVSCSICL<br>(SEQ ID NO: 6) |
| 488466015\|AGL06036\|<br>HA\|Human\|<br>fluB\|B/Massachusetts/<br>02/2012\|USA\|<br>2012/03/13\| | DRICTGITSSNSPHVVKTATQGEVNVTGVIPLTTTPTKSYFANL<br>KGTKTRGKLCPDCLNCTDLDVALGRPMCVGTTPSAKASILHE<br>VRPVTSGCFPIMHDRTKIRQLANLLRGYENIRLSTQNVIDAEKA<br>PGGPYRLGTSGSCPNATSKSGFFATMAWAVPKD-<br>NNKNATNPLTVEVPYICAEGEDQITVWGFHSDDKTQMKNLYG<br>DSNPQKFTSSANGVTTHYVSQIGGFPDQTEDGGLPQSGRIVVD<br>YMMQKPGKTGTIVYQRGVLLPQKVWCASGRSKVIKGSLPLIG<br>EADCLHEKYGGLNKSKPYYTGEHAKAIGNCPIWVKTPLKLAN<br>GTKYRPPAKLLKERGFFGAIAGFLEGGWEGMIAGWHGYTSHG<br>AHGVAVAADLKSTQEAINKITKNLNSLSELEVKNLQRLSGAM<br>DELHNEILELDEKVDDLRADTISSQIELAVLLSNEGIINSEDEHL<br>LALERKLKKMLGPSAVDIGNGCFETKHKCNQTCLDRIAAGTF<br>NAGEFSLPTFDSLNITAASLNDDGLDNHTILLYYSTAASSLAVT<br>LMLAIFIVYMVSRDNVSCSICL<br>(SEQ ID NO: 7) |
| 119515731\|ABL76694\|<br>HA\|Human\|<br>fluB\|B/Panama/45/<br>1990\|Panama\|1990/<br>03/07\| | DRICTGITSSNSPHVVKTATQGEVNVTGVIPLTTTPTKSHFANL<br>KGTKTRGKLCPNCLNCTDLDVALGRPMCVGTTPSAKASILHE<br>VRPVTSGCFPIMHDRTKIRQLPNLLRGYENIRLSTQNVINAERA<br>PGGPYRLGTSGSCPNVTSRDGFFATMAWAVPRD--<br>NKTATNPLTVEVPYICTKGEDQITVWGFHSDNKTQMKNLYGD<br>SNPQKFTSSANGVTTHYVSQIGGFPNQTEDGGLPQSGRIVVDY<br>MVQKPGKTGTIVYQRGVLLPQKVWCASGRSKVIKGSLPLIGE<br>ADCLHEKYGGLNKSKPYYTGEHAKAIGNCPIWVKTPLKLANG<br>TKYRPPAKLLKERGFFGAIAGFLEGGWEGMIAGWHGYTSHGA<br>HGVAVAADLKSTQEAINKITKNLNSLSELEVKNLQRLSGAMD<br>ELHNEILELDEKVDDLRADTISSQIELAVLLSNEGIINSEDEHLL<br>ALERKLKKMLGPSAVDIGNGCFETKHKCNQTCLDRIAAGTFN<br>AGEFSLPTFDSLNITAASLNDDGLDNHTILLYYSTAASSLAVTL<br>MIAIFIVYMVSRDNVSCSICL<br>(SEQ ID NO: 8) |
| 384038646\|AFH57909\|<br>HA\|Human\|<br>fluB\|B/Brisbane/<br>60/2008\|Australia\|<br>2008\| | DRICTGITSSNSPHVVKTATQGEVNVTGVIPLTTTPTKSHFANL<br>KGTETRGKLCPKCLNCTDLDVALGRPKCTGKIPSARVSILHEV<br>RPVTSGCFPIMHDRTKIRQLPNLLRGYEHIRLSTHNVINAENAP<br>GGPYKIGTSGSCPNITNGNGFFATMAWAVPKNDKNKTATNPL<br>TIEVPYICTEGEDQITVWGFHSDDETQMAKLYGDSKPQKFTSS<br>ANGVTTHYVSQIGGFPNQTEDGGLPQSGRIVVDYMVQKSGKT<br>GTITYQRGILLPQKVWCASGRSKVIKGSLPLIGEADCLHEKYG<br>GLNKSKPYYTGEHAKAIGNCPIWVKTPLKLANGTKYRPPAKL<br>LKERGFFGAIAGFLEGGWEGMIAGWHGYTSHGAHGVAVAAD<br>LKSTQEAINKITKNLNSLSELEVKNLQRLSGAMDELHNEILELD<br>EKVDDLRADTISSQIELAVLLSNEGIINSEDEHLLALERKLKKM<br>LGPSAVEIGNGCFETKHKCNQTCLDRIAAGTFDAGEFSLPTFDS<br>LNITAASLNDDGLDNHTILLYYSTAASSLAVTLMIAIFVVYMV<br>SRDNVSCSICL<br>(SEQ ID NO: 9) |

In various embodiments, engineered HA polypeptides as described herein comprise combinations of epitope sequences merged onto a particular viral backbone sequence. Multiple epitopes can be assembled on to any viral backbone as desired. In some embodiments, engineered HA polypeptides as described herein comprise a B/Massachusetts/02/2012, B/Panama/45/1990, B/Singapore/222/79, or B/Brisbane/60/2008 backbone sequence. Exemplary engineered mosaic HA polypeptides of the present invention are shown in Table 4.

TABLE 4

| | |
|---|---|
| br08_C01 | MKAIIVLLMVVTSNADRICTGITSSNSPHVVKTAT<br>QGEVNVTGVIPLTTTPTKSHFANLKGTETRGKLCP<br>KCLNCTDLDVALGRPKCTGKIPSARVSILHEVRPV<br>TSGCFPIMHDRTKIRQLPNLLRGYEHIRLSTQNVIN<br>AENAPGPYKIGTSGSCPNATNKSGFFATMAWAV<br>PKNDNNKTATNPLTIEVPYICTEGEDQITVWGFHS<br>DNKTQMKLYGDSKPQKFTSSANGVTTHYVSQIG<br>GFPNQTEDGGLPQSGRIVVDYMVQKPGKTGTIVY<br>QRGILLPQKVWCASGRSKVIKGSLPLIGEADCLUE<br>KYGGLNKSKPYYTGEHAKAIGNCPIWVKTPLKLA |

TABLE 4-continued br08_D02
NGTKYRPPAKLLLKERGFFGAIAGFLEGGWEGMIA
GWHGYTSHGAHGVAVAADLKSTQEAINKITKNL
NSLSELEVKNLQRLSGAMDELHNEILELDEKVDD
LRADTISSQIELAVLLSNEGIINSEDEHLLALERKL
KKMLGPSAVEIGNGCFETKHKCNQTCLDRIAAGT
FDAGEFSLPTFDSLNITAASLNDDGLDNHTILLYYS
TAASSLAVTLMIAIFVVYMVSRDNVSCSICL
(SEQ ID NO: 40)

br08_D02
MKAIIVLLMVVTSNADRICTGITSSNSPHVVKTAT
QGEVNVTGVIPLTTTPTKSYFANLKGTETRGKLCP
KCLNCTDLDVALGRPKCTGKIPSAKVSILHEVRPV
TSGCFPIMHDRTKIRQLPNLLRGYEHIRLSTQNVID
AENAPGGPYKIGTSGSCPNATNKSGFFATMAWAV
PKNDNNKTATNPLTIEVPYICTEGEDQITVWGFHS
DNKTQMKKLYGDSKPQKFTSSANGVTTHYVSQIG
GFPDQTEDGGLPQSGRIVVDYMVQKPGKTGTIVY
QRGILLPQKVWCASGRSKVIKGSLPLIGEADCLHE
KYGGLNKSKPYYTGEHAKAIGNCPIWVKTPLKLA
NGTKYRPPAKLLKERGFFGAIAGFLEGGWEGMV
AGWHGYTSHGAHGVAVAADLKSTQEAINKITKN
LNSLSELEIKNLQRLSGAMDELHNEILELDEKVDD
LRADTISSQIELAVLLSNEGIINSEDEHLLALERKL
KKMLGPSAVEIGNGCFETKHKCNQTCLDRIAAGT
FDAGEFSLPTFDSLNITAASLNDDGLDNHTILLYYS
TAASSLAVTLMIAIFVVYMVSRDNVSCSICL
(SEQ ID NO: 41)

br08_D03
MKAIIVLLMVVTSNADRICTGITSSNSPHVVKTAT
QGEVNVTGVISLTTTPTKSHFANLKGTKTRGKLCP
KCPNCTDLDVALGRPMCTGTIPSAKVSILHEVRPV
TSGCFPIMHDRTKIRQLPNLLRGYEHIRLSTHNVIN
AENAPGGPYKIGTSGSCPNATNKIGFFATMAWAV
PKNDNNKTATNPLTIEVPYICAEGEDQITVWGFHS
DDKTQMKKLYGDSKPQKFTSSANGVTTHYVSQIG
DFPNQTEDGGLPQSGRIVVDYMVQKPGKTGTITY
QRGILLPQKVWCASGRSKVIKGSLPLIGEADCLUE
KYGGLNKSKPYYTGEHAKAIGNCPIWVKTPLKLA
NGTKYRPPTKLLKERGFFGAIAGFLEGGWEGMIA
GWHGYTSHGAHGVAVAADLKSTQEAINKITKNL
NSLSELEVKNLQRLSGAMDELHNEILELDEKVDD
LRADTISSQIELAVLLSNEGIINSEDEHLLALERKL
KKMLGPSAVEIGNGCFETKHKCNQTCLNRIAAGT
FDAGEFSLPTFDSLNITAASLNDDGLDNHTILLYYS
TAASSLAVTLMIAIFVVYMVSRDNVSCSICL
(SEQ ID NO: 42)

pan90_D02
MKAIIVLLMVVTSNADRICTGITSSNSPHVVKTAT
QGEVNVTGVIPLTTTPTKSYFANLKGTETRGKLCP
NCLNCTDLDVALGRPKCVGKIPSAKASILHEVRPV
TSGCFPIMHDRTKIRQLPNLLRGYEHIRLSTQNVID
AERAPGGPYRLGTSGSCPNATSKSGFFATMAWAV
PKDDNNKTATNPLTVEVPYICTEGEDQITVWGFH
SDNKTQMKNLYGDSNPQKFTSSANGVTTHYVSQI
GGFPDQTEDGGLPQSGRIVVDYMVQKPGKTGTIV
YQRGVLLPQKVWCASGRSKVIKGSLPLIGEADCL
HEKYGGLNKSKPYYTGEHAKAIGNCPIWVKTPLK
LANGTKYRPPAKLLKERGFFGAIAGFLEGGWEGM
VAGWHGYTSHGAHGVAVAADLKSTQEAINKITK
NLNSLSELEIKNLQRLSGAMDELHNEILELDEKVD
DLRADTISSQIELAVLLSNEGIINSEDEHLLALERK
LKKMLGPSAVDIGNGCFETKHKCNQTCLDRIAAG
TFNAGEFSLPTFDSLNITAASLNDDGLDNHTILLY
YSTAASSLAVTLMIAIFIVYMVSRDNVSCSICL
(SEQ ID NO: 43)

ma12_RA82
MKAIIVLLMVVTSNADRICTGITSSKSPHVVKTAT
QGEVNVTGVIPLTTTPTKSHFANLRGTKTRGKLCP
DCLNCTDLDVALGRPKCVGNTPSAKASILHEVRP
VTSGCFPIMHDRTKIRQLANLLRGYEHIRLSNYNV
IDAEKAPGGPYRLGTSRSCPNVTSRSGFFATMAW
AVPKDDSNKNATNPLTVEVPYICTEGEDQITVWG
FHSDNKTQMVNLYGDSNPQKFTSSANGVTTHYV
SQIGDFPNQTEDGGLPQSGRIVVDYMMQKSGKTG
TITYQRGVLLPQKVWCASGRSVIKGTLPLIGEAD
CLHEKYGGLNKSKPYYTGEHAKAIGNCPIWVKTP
LKLANGTKYRPPAKLLKERGFFGAIAGFLEGGWE
GMIAGWHGYTSHGAHGVAVAADLKSTQEAINKI
TKNLNSLSELEVKNLQRLSGAMDELHNEILELDE
KVDDLRADTISSQIELAVLLSNEGIINSEDEHLLAL

TABLE 4-continued

ERKLKKMLGPSAVDIGNGCFETKHKCNQTCLDRI
AAGTFNAGEFSLPTFDSLNITAASLNDDGLDNHTI
LLYYSTAASSLAVTLMLAIFIVYMVSRDNVSCSICL
(SEQ ID NO: 44)

sing79_RA103
MKAIIVLLMVVTSNADRICTGITSSNSPHVVKTAT
QGEVNVTGVIPLTTTPTKSYFANLKGTKTRGKLCP
NCLNCTDLDVALGRPMCMGTIPSAKASILHEVRP
VTSGCFPIMHDRTKIRQLPNLLRGYENIRLSTHNVI
NAERAPGGPYIIGTSGSCPNATNKNGFFATMAWA
VPKDDNNKTATNPLTVEVPYICTEGEDQITVWGF
HSDNKTQMKKLYGDSKPQKFTSSANGVTTHYVS
QIGGFPDQTEDGGLPQSGRIVVDYMVQKSGKTGT
ITYQRGVLLPQKVWCASGRSKVIKGSLPLIGEADC
LHEKYGGLNKSKPYYTGEHAKAIGNCPIWVKTPL
KLANGTKYRPPAKLLKERGFFGAIAGFLEGGWEG
MIAGWHGYTSHGAHGVAVAADLKSTQEAINKIT
KNLNSLSELEVKNLQRLSGAMDELHNEILELDEK
VDDLRADTISSQIELAVLLSNEGIINSEDEHLLALE
RKLKKMLGPSAVDIGNGCFETKHKCNQTCLDRIA
AGTFNAGEFSLPTFDSLNITAASLNDDGLDNHTIL
LYYSTAASSLAVTLMIAIFIVYMVSRDNVSCSICL
(SEQ ID NO: 45)

In some embodiments, an engineered HA polypeptide of the present invention has a sequence at least about 95% (e.g., at least about 96%, 97%, 98% or 99%) identical to a sequence that appears in Table 4, wherein the sequence is not a naturally-occurring sequence. In some embodiments, an engineered HA polypeptide of the present invention has a sequence at least about 95% (e.g., at least about 96%, 97%, 98% or 99%) identical to a sequence that appears in Table 4, and further comprises a mosaic sequence pattern or consensus sequence template shown on Table 2.

In some embodiments, an engineered HA polypeptide of the present invention has a sequence that is substantially identical to a sequence that appears in Table 4.

In some embodiments, an engineered HA polypeptide of the present invention has a sequence that is identical to a sequence that appears in Table 4.

In some embodiments, an engineered HA polypeptide of the present invention is selected from a sequence that appears in Table 4.

In some embodiments, mosaic antigens as described herein are refined by molecular modeling to resolve structural problems and generate energy-minimized designs for engineered HA polypeptides. The total energies of the resulting designed molecules are calculated using a design algorithm. For example, the design algorithm in the Rosetta molecular modeling software version 3.1 (Simons et al., 1997, J. Mol. Biol. 268:209-225; Leaver-Fay et al., 2011, Methods Enzymol. 487:545-574) may be used. Molecules with negative total energy scores are predicted to have a good probability of folding into stable proteins while those with positive energy scores are considered less likely to fold properly. In addition to the total energy scores, per-residue energy scores for each molecule are evaluated in order to identify hot-spots (i.e., specific amino acid residues in the designed structures that had positive energy scores). Such hot spots may induce local misfolding with negative impact on epitope presentation on the surface of the molecule. The modeled structures are carefully examined visually to determine the location of the hot-spot residues relative to the surface of the molecule. In some embodiments, to further stabilize the molecular designs, high-energy residues situated outside of important epitope regions are substituted to more stable alternatives compatible with the local structural context. The resulting designs are more stable than the initial versions as determined by recalculated total energy scores.

Nucleic Acid Construction and Expression

Engineered influenza B HA or NA polypeptides as described herein may be produced from nucleic acid molecules using molecular biological methods known to the art. Nucleic acid molecules are inserted into a vector that is able to express the HA or NA polypeptides when introduced into an appropriate host cell. Appropriate host cells include, but are not limited to, bacterial, yeast, insect, and mammalian cells. Nucleic acid sequences may be codon optimized to facilitate expression in any of these host cells. Any of the methods known to one skilled in the art for the insertion of DNA fragments into a vector may be used to construct expression vectors encoding the fusion proteins of the present invention under control of transcriptional/translational control signals. These methods may include in vitro recombinant DNA and synthetic techniques and in vivo recombination (See Sambrook et al. Molecular Cloning, A Laboratory Manual, Cold Spring Harbor Laboratory; Current Protocols in Molecular Biology, Eds. Ausubel, et al., Greene Publ. Assoc., Wiley-Interscience, NY).

In some embodiments, the present invention provides nucleic acids which encode an HA or NA polypeptide or a characteristic or biologically active portion of an HA or NA polypeptide. In some embodiments, the invention provides nucleic acids which are complementary to nucleic acids which encode an HA or NA polypeptide or a characteristic or biologically active portion of an HA polypeptide.

In some embodiments, nucleic acids can be DNA or RNA, and can be single stranded or double-stranded. In some embodiments, nucleic acids in accordance with the invention may include one or more non-natural nucleotides; in some embodiments, nucleic acids in accordance with the invention include only natural nucleotides.

Expression of nucleic acid molecules in accordance with the present invention may be regulated by a second nucleic acid sequence so that the molecule is expressed in a host transformed with the recombinant DNA molecule. For example, expression of the nucleic acid molecules of the invention may be controlled by a promoter and/or enhancer element, which are known in the art.

Nucleic acid constructs of the present invention are inserted into an expression vector or viral vector by methods known to the art, and nucleic acid molecules are operatively linked to an expression control sequence.

An expression vector containing a nucleic acid molecule is transformed into a suitable host cell to allow for production of the protein encoded by the nucleic acid constructs. Exemplary host cells include prokaryotes (e.g., *E. coli*) and eukaryotes (e.g., a Vero, COS, 293 or CHO cell). Host cells transformed with an expression vector are grown under conditions permitting production of an engineered HA polypeptide the present invention followed by recovery of an engineered HA polypeptide.

Engineered HA polypeptides of the present invention may be purified by any technique known in the art. For example, not wishing to be bound by theory, engineered HA polypeptides may be recovered from cells either as soluble polypeptides or as inclusion bodies, from which they may be extracted quantitatively by 8M guanidinium hydrochloride and dialysis. In order to further purify engineered HA polypeptides of the present invention, conventional ion exchange chromatography, hydrophobic interaction chromatography, reverse phase chromatography or gel filtration may be used. Engineered HA polypeptides of the present invention may also be recovered from conditioned media following secretion from eukaryotic or prokaryotic cells.

Conformation of Engineered HA or NA Polypeptides

Engineered HA or NA polypeptides generated according to various methods described herein may be assessed for desired expression and conformation. Screening methods are known to the art and include cell-free, cell-based, and animal assays. In vitro assays can be either solid state or soluble target molecule detection may be achieved in a number of ways known to the art, including the use of a label or detectable group capable of identifying an engineered HA polypeptide which is bound to a target molecule (e.g., immunoglobulin). Detectable labels may be used in conjunction with assays using engineered HA or NA polypeptides of the present invention. For example, engineered HA or NA polypeptide as described herein may be evaluated and selected based on expression and conformational characteristics as determined by assays described in International Patent Application PCT/US2015/033205 entitled "Expression and Conformational Analysis of Engineered Influenza Hemagglutinin" filed on May 29, 2015.

Other binding assays may also be used to evaluate expression and conformation of engineered HA or NA polypeptides, including but not limited to, a Protein Expression and Purification Platform (PEPP) system, or a Biolayer Interferometry (BLI) system. In some embodiments, expression and conformation of engineered HA or NA polypeptides may be measured and ranked by quantitating the level of monoclonal antibody binding.

The present invention also provides methods for testing engineered HA or NA polypeptides in accordance with the invention in an animal host. As used herein, an "animal host" includes any animal model suitable for influenza research. For example, animal hosts suitable for the invention can be any mammalian hosts, including primates, ferrets, cats, dogs, cows, horses, rodents such as, mice, hamsters, rabbits, and rats. In some embodiments, an animal host used for the invention is a ferret. In particular, in some embodiments, an animal host is naïve to viral exposure or infection prior to administration of a binding agent in accordance with the invention (optionally in a composition in accordance with the invention). In some embodiments, the animal host is inoculated with, infected with, or otherwise exposed to virus prior to or concurrent with administration of an engineered HA or NA polypeptide in accordance with the invention. An animal host used in the practice of the present invention can be inoculated with, infected with, or otherwise exposed to virus by any method known in the art. In some embodiments, an animal host may be inoculated with, infected with, or exposed to virus intranasally.

Naïve and/or inoculated animals may be used for any of a variety of studies. For example, such animal models may be used for hemagglutinin inhibition assays, microneutralization assays, challenge assays and virus transmission studies, as in known in the art. It is contemplated that the use of ferrets in virus transmission studies may serve as a reliable predictor for virus transmission in humans. For example, air transmission of viral influenza from inoculated animals (e.g., ferrets) to naïve animals is known in the art (Tumpey et al., 2007, Science 315; 655-59; incorporated herein by reference). Virus transmission studies may be used to test engineered HA polypeptides in accordance with the invention. For example, engineered HA polypeptides in accordance with the invention may be administered to a suitable animal host in order to determine the efficacy of said engineered HA polypeptide in eliciting a broad immune response in the animal host. Using information gathered from studies in an animal host, one may predict the efficacy of an engineered HA polypeptide to elicit broadly protective in a human host.

Pharmaceutical Compositions

In some embodiments, the present invention provides for pharmaceutical compositions including an engineered HA or NA polypeptide as described herein and/or related entities. For example, in some embodiments, engineered HA or NA polypeptides, nucleic acids encoding such polypeptides, characteristic or biologically active fragments of such polypeptides or nucleic acids, antibodies that bind to and/or compete with such polypeptides or fragments, small molecules that interact with or compete with such polypeptides or with glycans that bind to them, etc. are included in pharmaceutical compositions in accordance with the invention.

Such pharmaceutical compositions are typically formulated as immunogenic or vaccine compositions. In some embodiments, the immunogenic compositions are pharmaceutical compositions comprising one or more of the following: (1) inactivated virus, (2) live attenuated influenza virus, for example, replication-defective virus, (3) virus-like particles (VLPs), (4) engineered HA or NA polypeptide, (5) nucleic acid encoding an engineered HA or NA polypeptide or characteristic or biologically active portion thereof, (6) DNA vector that encodes an engineered HA polypeptide in accordance with the invention or characteristic or biologically active portion thereof, and/or (7) expression system, for example, cells expressing one or more influenza proteins to be used as antigens.

In some embodiments, the present invention provides methods of preventing or treating influenza infections by administration of such pharmaceutical compositions in accordance with the invention. In some embodiments, pharmaceutical compositions in accordance with the invention are administered to a subject suffering from or susceptible to an influenza infection. In some embodiments, a subject is an animal, including but not limited to birds (e.g., chickens, ducks, turkeys, etc.), dogs, horses and pigs. In some embodiments, a subject is considered to be suffering from an influenza infection in the subject is displaying one or more symptoms commonly associated with influenza infection. In some embodiments, the subject is known or believed to have been exposed to the influenza virus. In some embodiments, a subject is considered to be susceptible to an influenza infection if the subject is known or believed to have been exposed to the influenza virus. In some embodiments, a subject is known or believed to have been exposed to the influenza virus if the subject has been in contact with other individuals known or suspected to have been infected with the influenza virus and/or if the subject is or has been present in a location in which influenza infection is known or thought to be prevalent.

In some embodiments, subjects suffering from or susceptible to influenza infection are tested for antibodies to engineered HA or NA polypeptides in accordance with the invention prior to, during, or after administration of pharmaceutical compositions in accordance with the invention. In some embodiments, subjects having such antibodies are not administered pharmaceutical compositions comprising engineered HA or NA polypeptides in accordance with the invention. In some embodiments, an appropriate dose of pharmaceutical composition and/or engineered HA or NA polypeptide is selected based on detection (or lack thereof) of such antibodies.

In some embodiments, selection of a particular subject for treatment, particular engineered HA or NA polypeptide or composition for administration, and/or particular dose or regimen for administration, is memorialized, for example in a written, printed, or electronic storage form.

Compositions comprising an engineered HA or NA polypeptide as described may be administered prior to or after development of one or more symptoms of influenza infection. In some embodiments, a vaccine comprising an engineered HA or NA polypeptide as described herein may be administered prior to or after development of one or more symptoms of influenza infection.

In some embodiments, the present invention provides for treatment of influenza infections by administration of engineered HA or NA polypeptides described herein. In some embodiments, treatment of influenza infections according to the present invention is accomplished by administration of an influenza VLP comprising an engineered HA or NA polypeptide as described herein. In some embodiments, treatment of influenza infections according to the present invention is accomplished by administration of a vaccine. To date, although significant accomplishments have been made in the development of influenza vaccines, there is room for further improvement. The present invention provides vaccines comprising engineered HA polypeptides in accordance with the invention, and particularly comprising engineered HA polypeptides that elicit broadly protective immune responses to multiple neutralizing antigenic determinants (e.g., epitope) of the engineered HA polypeptides.

In some embodiments, the present invention provides for immunogenic compositions (e.g., vaccines) and the administration of these immunogenic compositions to a human subject. In particular embodiments, a human subject is 6 months of age or older, is 6 months through 35 months of age, is 36 months through 8 years of age, or 9 years of age or older.

Thus, in some embodiments, the present invention provides inactivated flu vaccines. In some embodiments, inactivated flu vaccines comprise one of three types of antigen preparation: inactivated whole virus, sub-virions where purified virus particles are disrupted with detergents or other reagents to solubilize the lipid envelope ("split" vaccine) or purified HA polypeptide ("subunit" vaccine). In some embodiments, virus can be inactivated by treatment with formaldehyde, beta-propiolactone, ether, ether with detergent (such as TWEEN-80®), cetyl trimethyl ammonium bromide (CTAB) and Triton N101, sodium deoxycholate and tri(n-butyl) phosphate. Inactivation can occur after or prior to clarification of allantoic fluid (from virus produced in eggs); the virions are isolated and purified by centrifugation (Nicholson et al., eds., 1998, Textbook of Influenza, Blackwell Science, Malden, Mass.; incorporated herein by reference). To assess the potency of the vaccine, the single radial immunodiffusion (SRID) test can be used (Schild et al., 1975, Bull. World Health Organ., 52:43-50 & 223-31; Mostow et al., 1975, J. Clin. Microbiol., 2:531; both of which are incorporated herein by reference).

In some embodiments, engineered HA polypeptides of the present invention are used as a component of seasonal influenza vaccines or as part of an influenza vaccination regimen intended to confer long-lasting (multi-season) protection. The nucleic acid sequences encoding the engineered influenza HA polypeptides obtained by the methods described herein can be combined with one or more donor viruses and used in a reverse genetics system to produce an infectious reassortant influenza virus. Reverse genetics systems can be used produce infectious, reassortant viruses, or attenuated viruses from their cDNAs. The reverse genetics methods are well-known by the one skilled in the art and include, but are not limited to, the methods using the plasmids described in Neuman et al, 1999, Proc Natl Acad Sci USA, 96(16):9345-9350; Neumann et al, 2005, Proc Natl Acad Sci USA, 102(46):16825-16829; Zhang et al, 2009, J Virol, 83(18):9296-9303; Massin et al, 2005, J Virol, 79(21):1381 1-13816; Murakami et al, 2008, 82(3):1605-1609; and/or the cells described in Neuman et al, 1999, Proc Natl Acad Sci USA, 96(16):9345-9350; Neumann et al, 2005, Proc Natl Acad Sci USA, 102(46): 16825-16829; Zhang et al, 2009, J Virol, 83(18):9296-9303; Massin et al, 2005, J Virol, 79(21):1381 1-13816; Murakami et al, 2008, 82(3):1605-1609; Koudstaal et al, 2009, Vaccine, 27(19): 2588-2593; Schickli et al, 2001, Philos Trans R Soc Lond Biol Sci, 356(1416):1965-1973; Nicolson et al, 2005, Vaccine, 23(22):2943-2952; Legastelois et al, 2007, Influenza Other Respi Viruses, 1 (3):95-104; Whiteley et al, 2007, Influenza Other Respi Viruses, 1 (4): 157-166.

In certain embodiments, the reverse genetics method may be:

(i) the 16 plasmid method, such as the method described by Neuman et al, 1999, Proc Natl Acad Sci USA, 96(16): 9345-9350, and in US 2009/0246830 or US 2011/0143424 (each of which is hereby incorporated by reference in its entirety), in which the influenza virus is produced by transfecting cells, using a polyamine derivative (Trans IT-LT1), with 8 plasmids each containing a cDNA complementary to one influenza vRNA under the control of an RNA polymerase I promoter and an RNA polymerase I terminator, and 8 plasmids each containing a cDNA complementary to one of the PA, PB1, PB2, NP, HA, NA, M and NS mRNAs under the control of RNA polymerase II promoter. In particular, the cells are human kidney embryonic adherent cells (293T cell line);

(ii) the 12 plasmid method, such as the method described by Fodor et al, 1999, J Virol, 73(1 1):9679-9682, and in US 2004/0142003, US 2012/0058538 (each of which is hereby incorporated by reference in its entirety) in which the influenza virus is produced by transfecting a first cell type with 8 plasmids each containing a cDNA complementary to one influenza vRNA under the control of an RNA polymerase I promoter and an RNA polymerase I terminator (hepatitis delta ribozyme), and 4 plasmids each containing a cDNA complementary to one of the NP, PA, PB1 and PB2 mRNAs under the control of RNA polymerase II promoter, and by further amplifying the virus on a second cell type. In particular, said first cell type is Vero cells and said second cell type is MDBK;

(iii) the 13 plasmid method, such as the method described by De Wit et al, 2007, Journal of General Virology, 88:1281-1287 (which is hereby incorporated by reference in its entirety) in which the influenza virus is produced by transfecting cells with 8 plasmids each containing a cDNA complementary to one influenza vRNA under the control of an T7 RNA polymerase promoter and an T7 RNA polymerase terminator, 4 plasmids each containing a cDNA complementary to one of the NP, PA, PB1 and PB2 mRNAs under the control of RNA polymerase II, and one plasmid containing the cDNA complementary to the mRNA encoding the T7 RNA polymerase and a nuclear localization signal under the control of RNA polymerase II. In particular, the transfected cells are Vero, 293T, or QT6 (fibrosarcoma cell line from Japanese quail) cells.

(iv) the 8 plasmid method, such as the method described by Hoffmann et al, 2000, PNAS, 97(1 1):6108-61 13 and in WO 01/83794 (each of which is hereby incorporated by reference in its entirety) in which each plasmid is capable of expressing both mRNA and vRNA(s). Thus each plasmid contains cDNA complementary to one influenza vRNA and two transcription cassettes instead of one as in the preceding case. The cDNA complementary of each of the eight influenza virus vRNAs is inserted between the polymerase I terminator and the polymerase I promoter. This polymerase I transcription unit is flanked by the polymerase II promoter and a polyadenylation signal. The first transcription cassette allows the transcription of cDNA in the form of a vRNA. The second transcription cassette allows the transcription of cDNA in the form of mRNA which is then translated into viral protein(s) using the cellular machinery. With the aid of this double cassette system for transcription, also called Pol 1-Pol II system, the cDNA of the same plasmid is transcribed both in the form of vRNA and in the form of mRNA. This manifests itself at the level of the transfected cell by the expression of a vRNA and of one or more viral proteins. In particular, a co-culture of adherent MDCK cells and of 293T cells and, as transfection agent, a polyamine derivative (Trans IT-LT1) are used.

(v) the 3 plasmid method, such as the method described by Neumann et al, 2005, PNAS, 102(46): 16825-16829 (which is hereby incorporated by reference in its entirety), in which the influenza virus is produced by transfecting cells with one plasmid containing the 8 cDNAs complementary to PB2, PB1, PA, HA, NP, NA, M and NS vRNAs each under the control of an RNA polymerase I promoter and a polymerase I terminator and 2 plasmids, the first one containing the 3 cDNA complementary to one of the PB2, PB1 and PA mRNAs and the second one containing the cDNA complementary to the NP mRNA, under the control of a RNA polymerase II promoter. In particular, the transfected cells are 293T or Vero.

(vi) the 1 plasmid method, such as the method described by Zhang et al, J. Virol., 83(18): 9296-9303 (which is hereby incorporated by reference in its entirety), in which the influenza virus is produced by transfecting cells with one plasmid containing the 8 cDNAs complementary to PB2, PB1, PA, HA, NP, NA, M and NS vRNA under the control of murine polymerase I terminator and a chicken RNA polymerase I promoter and with a polymerase II promoter and a polyadenylation signal between PB2, PB1, PA and NP cDNAs. In particular, the transfected cells are CEF cells.

(vii) the method described in WO 2005/062820 (which is hereby incorporated by reference in its entirety) using two different cellular systems: in a first step, cells are transfected with 8 bidirectional plasmids with the PolI-PolII system (Pol/Poll) and then in a second step, the transfected cells are cultured with cells from another cell line that is very permissive for the influenza virus in order to amplify the production of the influenza virus. In particular, said transfected cells in the first step are Vero cells, and said other cell line in the second step are CEK or CEF cell lines which are lines derived from chicken embryo cells.

In some embodiments, prior to being used in the reverse genetics methods described above, nucleic acid sequences encoding the engineered influenza HA polypeptides may be further optimized according to the method described in U.S. provisional application 62/172,949, incorporated by reference herein.

In some embodiments, influenza virus for use in vaccines is grown in eggs, for example, in embryonated hen eggs, in which case the harvested material is allantoic fluid. Alternatively or additionally, influenza virus or engineered hemagglutinin polypeptides may be produced from any method using tissue culture to grow the virus. Suitable cell substrates for growing the virus or otherwise recombinantly producing the engineered hemagglutinin polypeptides include, for example, dog kidney cells such as MDCK or cells from a clone of MDCK, MDCK-like cells, monkey kidney cells such as AGMK cells including Vero cells, cultured epithelial cells as continuous cell lines, 293T cells, BK-21 cells, CV-1 cells, or any other mammalian cell type suitable for the production of influenza virus (including upper airway epithelial cells) for vaccine purposes, readily available from commercial sources (e.g., ATCC, Rockville, Md.). Suitable cell substrates also include human cells such as MRC-5 cells. Suitable cell substrates are not limited to cell lines; for example primary cells such as chicken embryo fibroblasts are also included.

Engineered hemagglutinin polypeptides may also be expressed/produced in diverse eukaryotic-based expression systems, including microalgae (e.g. Schizochytrium sp.; see, e.g., Bayne, A-C.V. et al., PLOS ONE, 8(4):e61790, April 2013), plant-based systems (e.g., tobacco plants; see, e.g., Jul-Larsen, A., et al., Hum Vaccin Immunother., 8(5):653-61, 2012), yeast (see, e.g., Athmaram, T. N. et al., Virol J., 8:524, 2011), and fungi (see, e.g., Allgaier, S. et al., Biologicals, 37:128-32, 2009). Bacterial based expression systems are also encompassed by the present invention (see, e.g., Davis, A. R. et al., Gene, 21:273-284, 1983).

In some embodiments, vaccines in accordance with the invention further comprise one or more adjuvants. For example, aluminum salts (Baylor et al., 2002, Vaccine, 20:S18; incorporated herein by reference) and monophosphoryl lipid A (MPL; Ribi et al., 1986, Immunology and Immunopharmacology of Bacterial Endotoxins, Plenum Publ. Corp., NY, p. 407; incorporated herein by reference) can be used as adjuvants in human vaccines. Alternatively or additionally, new compounds are currently being tested as adjuvants in human vaccines, such as AS03, MF59, and saponins such as QS21.

Additionally, some adjuvants are known in the art to enhance the immunogenicity of influenza vaccines, such as poly[di(carboxylatophenoxy)phosphazene] (PCCP; Payne et al., 1998, Vaccine, 16:92; incorporated herein by reference), interferon-γ (Cao et al., 1992, Vaccine, 10:238; incorporated herein by reference), block copolymer P1205 (CRL1005; Katz et al., 2000, Vaccine, 18:2177; incorporated herein by reference), interleukin-2 (IL-2; Mbwuike et al., 1990, Vaccine, 8:347; incorporated herein by reference), and polymethyl methacrylate (PMMA; Kreuter et al., 1981, J. Pharm. Sci., 70:367; incorporated herein by reference).

In addition to immunogenic compositions (e.g., vaccines comprising one or more of the engineered influenza hemagglutinin polypeptides described herein), the present invention provides other therapeutic compositions useful in the treatment of viral infections. Therapeutic compositions include, for example, influenza VLPs, fusions proteins, and an engineered HA polypeptide itself as described herein.

In some embodiments, any of the immunogenic compositions (e.g., vaccines) described herein offer broad cross-protection against different varieties of influenza viruses. For example, in some embodiments, immunogenic compositions described herein offer cross-protection against pinnipeds and/or human-adapted influenza B viruses. In some embodiments, any of the immunogenic compositions described herein offer cross-protection against one or more influenza B lineage strains. In some embodiments, the immunogenic compositions described herein provide cross-protection against multiple strains of influenza B lineages (see, e.g., FIG. 3).

Pharmaceutical compositions of the present invention can be administered by a variety of routes, including oral, intravenous, intramuscular, intra-arterial, subcutaneous, intraventricular, transdermal, interdermal, rectal, intravaginal, intraperitoneal, topical (as by powders, ointments, creams, or drops), mucosal, nasal, buccal, enteral, sublingual; by intratracheal instillation, bronchial instillation, and/or inhalation; and/or as an oral spray, nasal spray, and/or aerosol. In general the most appropriate route of administration will depend upon a variety of factors including the nature of the agent (e.g., its stability in the environment of the gastrointestinal tract), the condition of the patient (e.g., whether the patient is able to tolerate oral administration), etc.

In some embodiments parenteral administration, such as subcutaneous, intravenous or intramuscular administration, is achieved by injection. In some embodiments, injectables are prepared in conventional forms, either as liquid solutions or suspensions, solid forms suitable for solution or suspension in liquid prior to injection, or as emulsions. In some embodiments, injection solutions and suspensions are prepared from sterile powders, granules, and.

General considerations in the formulation and manufacture of pharmaceutical agents may be found, for example, in *Remington's Pharmaceutical Sciences*, $19^{th}$ ed., Mack Publishing Co., Easton, Pa., 1995; incorporated herein by reference.

Pharmaceutical compositions in accordance with the invention may be administered in any dose appropriate to achieve a desired outcome. In some embodiments, the desired outcome is induction of a lasting adaptive immune response against multiple influenza strains. In some embodiments, the desired outcome is reduction in intensity, severity, and/or frequency, and/or delay of onset of one or more symptoms of influenza infection.

In some embodiments, pharmaceutical compositions in accordance with the invention are administered in single or multiple doses. In some embodiments, pharmaceutical compositions in accordance with the invention are administered in multiple doses administered on different days (e.g., prime-boost vaccination strategies). In some embodiments, pharmaceutical compositions in accordance with the invention are administered according to a continuous dosing regimen, such that the subject does not undergo periods of less than therapeutic dosing interposed between periods of therapeutic dosing. In some embodiments, pharmaceutical compositions in accordance with the invention are administered according to an intermittent dosing regimen, such that the subject undergoes at least one period of less than therapeutic dosing interposed between two periods of therapeutic dosing.

In some embodiments, a dose administered to a subject should be sufficient to induce a beneficial therapeutic response in a subject over time, or to inhibit or prevent influenza B virus infection. In some embodiments, the dose comprises 15 μg of one of the engineered influenza B HA polypeptides described herein. In some embodiments, the dose comprises 7.5 μg of one of the engineered influenza B HA polypeptides described herein. In some embodiments, the dose comprises 3.0 μg of one of the engineered influenza B HA polypeptides described herein. The dose required may vary from subject to subject depending on the species, age, weight and general condition of the subject, the severity of the infection being treated, the particular composition being used and its mode of administration.

The present invention will be more fully understood by reference to the following Examples. All literature citations are incorporated by reference.

EXAMPLES

These Examples are set forth to aid in the understanding of the invention but are not intended to, and should not be construed to limit its scope in any way. The Examples do not include detailed descriptions of conventional methods that would be well known to those of ordinary skill in the art (molecular cloning techniques, etc.). Unless indicated otherwise, parts are parts by weight, molecular weight is average molecular weight, temperature is indicated in Celsius, and pressure is at or near atmospheric.

Example 1. Design and Methodology for Construction of Hemagglutinin (HA) Polypeptides The present Example describes the design and production of engineered HA polypeptides that elicit broad neutralizing immune responses. The engineered HA polypeptides combine multiple B-cell epitopes from different hemagglutinin sequences to create mosaic antigens. The present Example specifically illustrates construction of engineered HA polypeptides that combine HA sequences from influenza B lineages and strains. These mosaic antigens are predicted to confer cross-protection against multiple strains by maximizing sequence homology for at least one neutralizing epitope. Further, these mosaic antigens can be used alone or in combination with other influenza antigens, as a component of seasonal influenza vaccines, or as part of a vaccination regimen intended to confer long-lasting, multi-season protection against influenza infection.

Additional Examples presented herein demonstrate the successful immune response elicited by these engineered HA polypeptides, as assayed by HA inhibition using sera from immunized animals. These Examples demonstrate the potential of the presently described methodology for the design and production of engineered HA polypeptides and provide the next-generation of broadly cross-reactive and neutralizing influenza vaccines.

Figure 6:
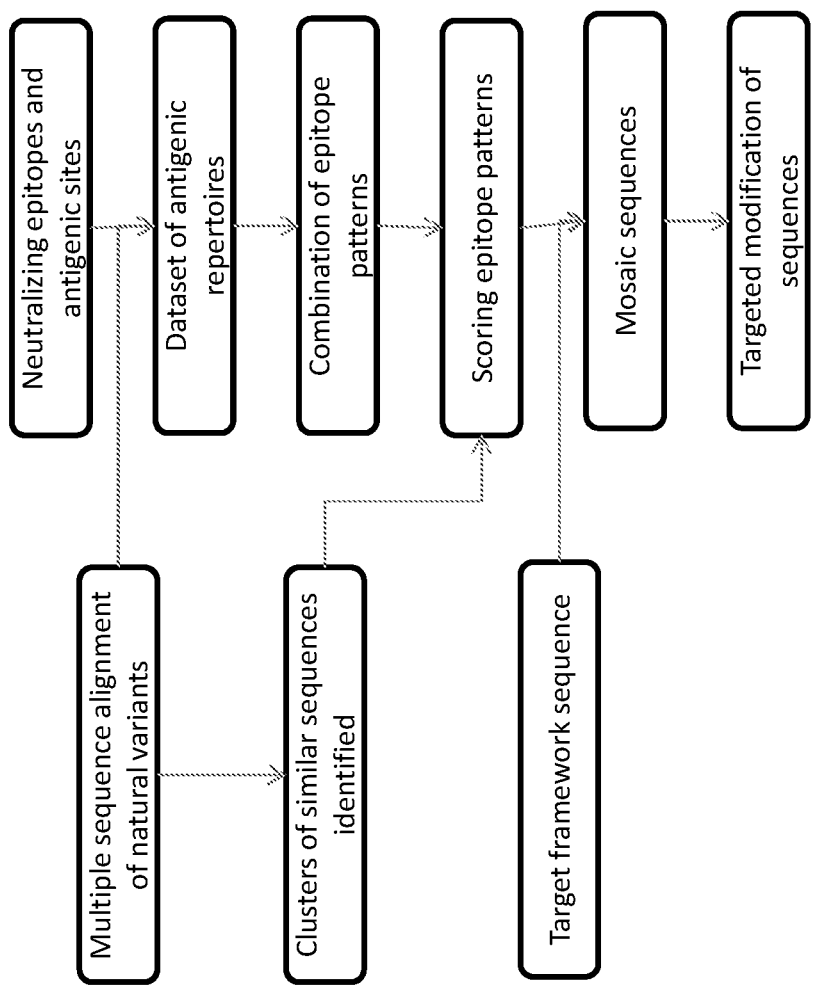
FIG. 6 shows an exemplary flowchart for the design and production of engineered HA polypeptides using structural mapping of antigenic repertoires. Antigenic repertoires of multiple epitopes were identified and organized into alignment coverage optimized repertoire subsets. Mosaic sequences were generated through combination of different epitopes. Mosaic combinations of epitopes were evaluated for alignment coverage based on geographic regions, viral isolate years, viral sub-family clusters or other measures to identify high scoring designs. Generated mosaic sequences were optimized by structural refinement and could be further refined through targeted sequence modifications.

FIG. 6 sets forth an exemplary flowchart of the methodology for the design and production of engineered HA polypeptides as described herein.

Principal Component Analysis to Assess Cross Reactivity of Influenza B HAs

Principal Components Analysis (PCA) is a common technique for working with high dimensional data and highlighting patterns in the data (i.e. it can be used to simplify large datasets and facilitate data exploration and visualization). Applied to biological sequences (proteins, genes), the technique enables comparison of thousands of sequences and the identification of groups of similar sequences based on a measure of sequence dissimilarity (Hamming distance, percent identity, percent similarity, surface accessibility, etc.). In the case of Human influenza B viruses, hemagglutinin (HA) protein sequences were obtained from the NCBI Influenza Virus Resource database, trimmed to remove signal peptides, transmembrane regions and cytoplasmic tails and the resulting ectodomain sequences were aligned. The pair-wise dissimilarity matrix was calculated from the multiple sequence alignment based on the Hamming distance between pairs of sequences with no prior assumptions regarding function or structure of the sequences. Principal Components Analysis (PCA) was applied to the dissimilarity matrix for the purpose of dimension reduction and to facilitate visualization of the relative distances between HA proteins. The first 2-3 principal components were retained for visualizing protein relationships in sequence space and represent a reasonable approximation of the general structure of the phylogenetic tree. Calculations were performed using custom scripts written in python and R.

Visualization of the first 2 principal components identifies clear patterns associated with influenza B hemagglutinins including the two influenza B lineages (Yamagata vs Victoria). Additionally, sequences form distinct clusters based on similarity. Reference and vaccine strains are highlighted in FIG. 5 as are engineered SMARt HA sequences (grey diamonds) which show little overlap with the clusters consisting of circulating strain HA sequences.

Figure 5:
FIG. 5 shows a plot of the first two principal components from a principal component analysis of the pairwise sequence identity matrix enabling the identification of clear patterns associated with influenza B hemagglutinins including the two influenza B lineages (Yamagata vs Victoria). Additionally, sequences form distinct clusters based on similarity. Reference and vaccine strains are highlighted as circles and arrows respectively, in FIG. 5 as are engineered SMARt HA sequences (grey diamonds) which show little overlap with the clusters consisting of circulating strain HA sequences.

A broadly protective antigen should be cross-reactive across multiple clusters within and between lineages (FIG. 5). Modifications designed into the engineered HAs were deduced from an in silico analysis of sequence variation in both past and current circulating influenza strains. This analysis included mapping antigenic and epitope patterns as well as structural modeling of the HA protein. Targeted changes were subsequently introduced at precise amino acid residue locations and/or specific regions of the protein with known immune profiles in order to yield novel influenza B HA polypeptides that would be reactive across the sequence clusters illustrated in FIG. 5.

Each novel mosaic design was composed of multiple neutralizing hemagglutinin B-cell epitope patterns derived from antigenically diverse influenza B strains (including both Yamagata and Victoria lineages). The mosaic pattern of B-cell epitopes were assembled onto a backbone hemagglutinin sequence. One of the following nine backbone hemagglutinin sequences was used: B/Hong Kong/330/2001, B/Hong Kong/05/1972, B/Lee/40, B/Massachusetts/02/2012, B/Panama/45/1990, B/Singapore/222/79, B/Victoria/02/1987, B/Yamagata/16/1988, B/Brisbane/60/2008. The selected backbone provides the inter-epitope sequence of the engineered construct as well as the signal peptide and transmembrane domains required for full-length hemagglutinin molecules that are expressed and functional.

Structural Mapping of Antigenic Repertoires

Figure 7:
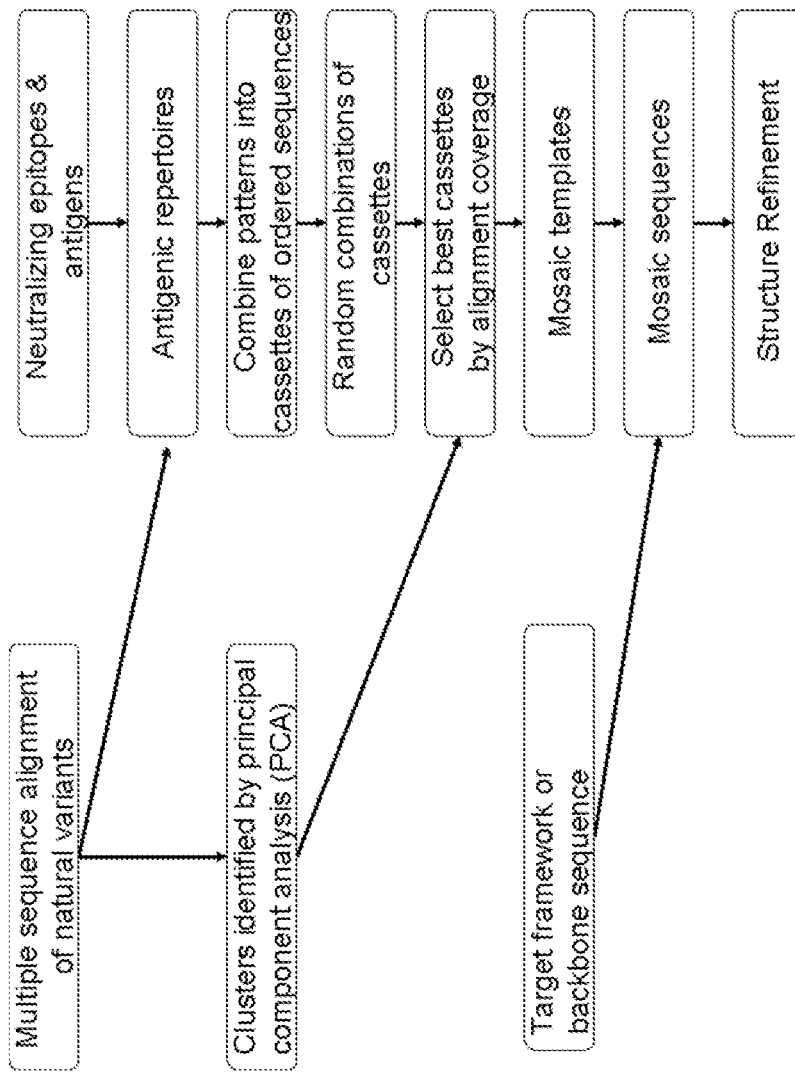
FIG. 7 shows an exemplary flowchart for the design and production of engineered mosaic antigenic polypeptides.
Figure 8:
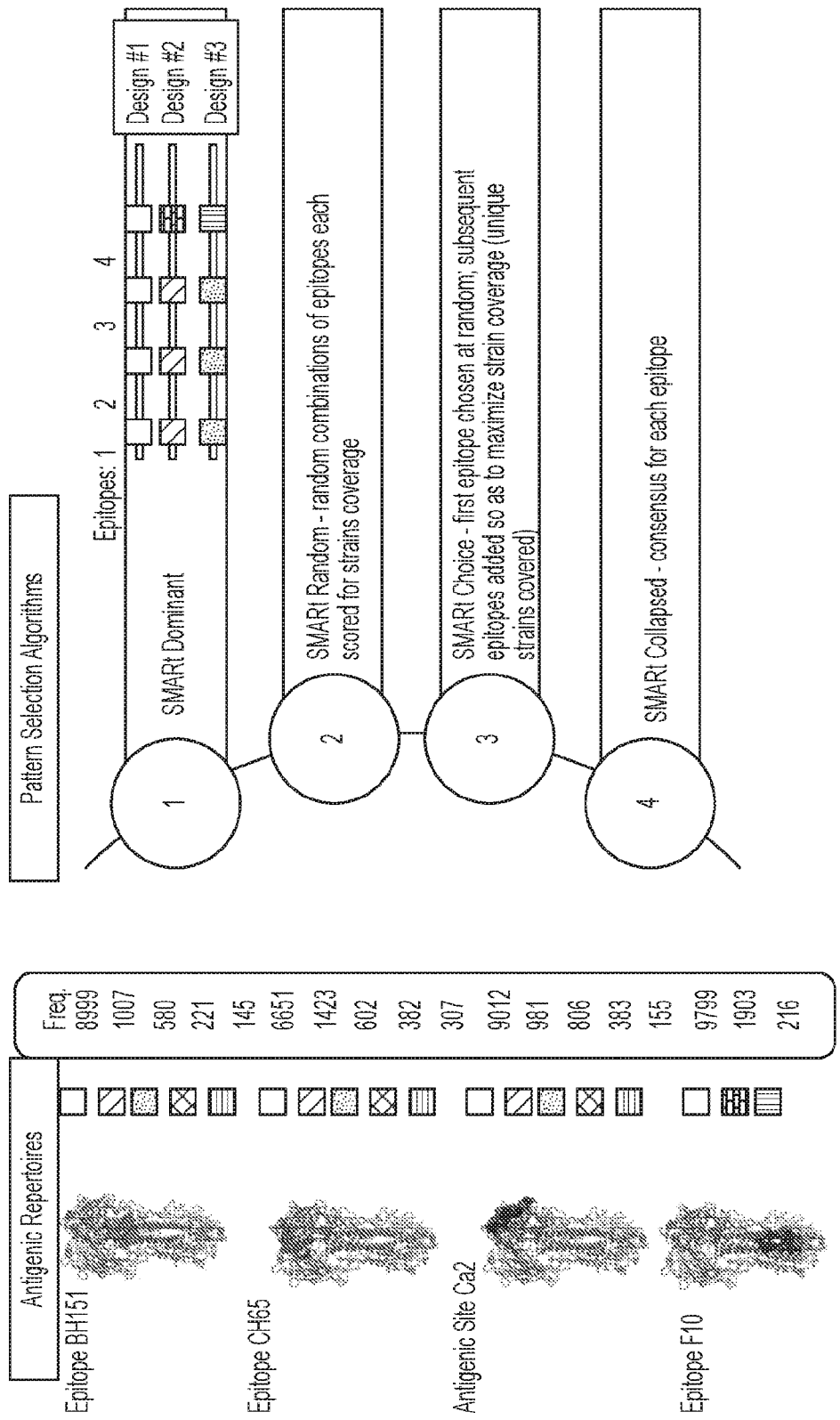
FIG. 8 shows an exemplary overview of the four distinct SMARt pattern selection processes.

The approach used here to construct mosaic hemagglutinin sequences is termed 'SMARt' for Structural Mapping of Antigenic Repertoires (an overview of the process is presented in FIGS. 7 and 8). Briefly, known neutralizing and non-neutralizing hemagglutinin B-cell epitopes described for any B virus were mapped to corresponding regions of Influenza B HA. Individual sequences for each B-cell epitope were extracted and enumerated from the sequences of all available circulating Influenza B strains to generate an 'antigenic repertoire'. Four distinct SMARt workflows were developed to combine antigenic repertoires into novel mosaic hemagglutinin molecules that are distinct from natural circulating strains. An overview of the compiled SMARt workflow is presented in FIG. 8.

Figure 9:
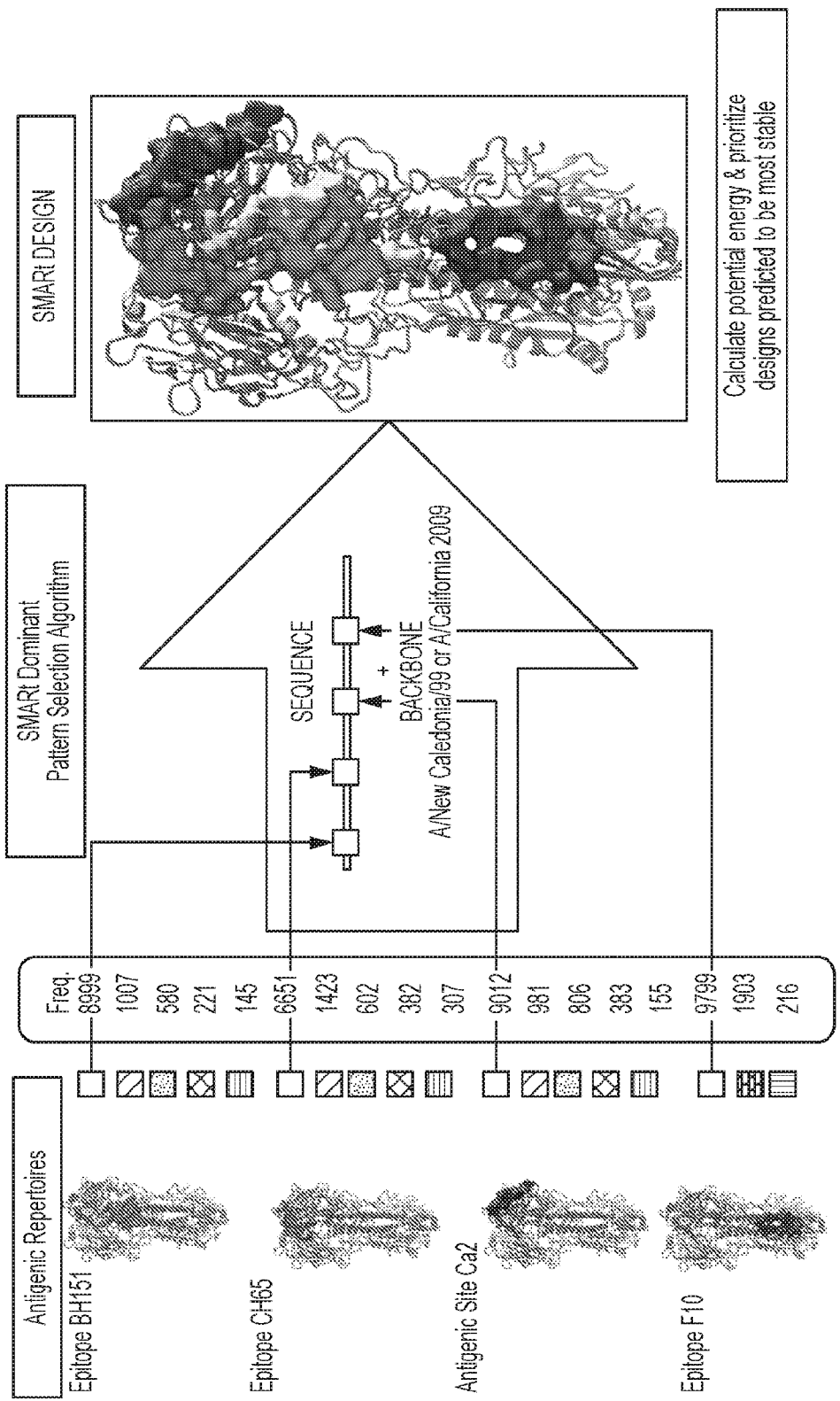
FIG. 9 shows an exemplary workflow of the SMARt Dominant workflow to design engineered mosaic antigenic polypeptides.

FIG. 9 provides a demonstration of the complete process to generate a SMARt Dominant HA design. Table 5 provides epitope sequence patterns represented in FIG. 9.

TABLE 5

| Epitope Sequence Patterns | Counts |
| --- | --- |
| GKAPLKPESLTSDGDPVH | 8890 |
| GKAPLNPELLKNEGNPMD | 1007 |
| GKAPLNPELLTNEGNPMD | 680 |
| GKAPLKPETLTSDGDPVH | 221 |
| GKAPLNPELLTNEGNPNG | 145 |
| YDNKGVTAKWVKKGNSHSTSADQSLQIDOE | 6061 |
| YDNKGVTAKWVKKGNSHSTTADQSLQIDOE | 1423 |

TABLE 5-continued

| Epitope Sequence Patterns | Counts |
|---|---|
| YTT-GVSASWTGKNGLHPNIGDRALHKDQE | 802 |
| YDNKGVTAKWVKKGNSHSTSADQSLQIEQE | 382 |
| YTT-GVSASWTGKNGLKPNIGDKALKKDQE | 307 |
| SHNGESRD | 9012 |
| SHNGKSRD | 981 |
| PHAGAKRE | 808 |
| PHAGAKRG | 383 |
| PHAGAKRG | 166 |
| VHHSLVDGWLTQAIOITKVNVIT | 9789 |
| YHHSLVDGWQTQAINITKVNVIT | 1893 |
| YHHSLIDGWQTQAINITKVNVIT | 216 |

Structural Modeling and Selection of Designs

Figure 10:
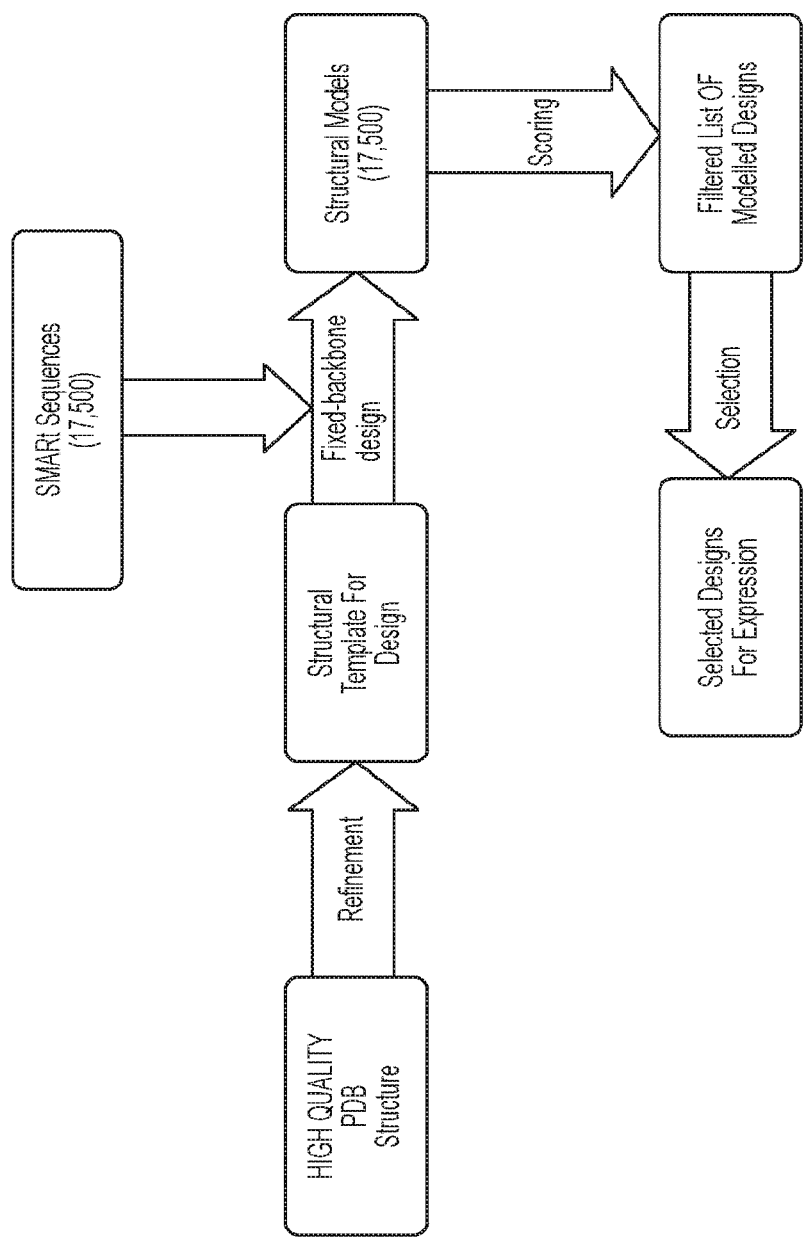
FIG. 10 demonstrates an exemplary workflow to input SMARt design sequences into a fixed backbone model and subsequently score and select the engineered antigenic polypeptides.

One aspect of the SMARt workflow for the design of mosaic antigens is structure-based molecular modeling to identify designs with conformational stability, which are then selected for experimental validation. A summary of the modeling and selection process is provided in FIG. 10. Three-dimensional coordinates of a high-quality structure of influenza B hemagglutinin (HA) were used as the template for modeling the structural backbones into which epitope repertoires were inserted (PDB ID: 4M40).

Figure 11:
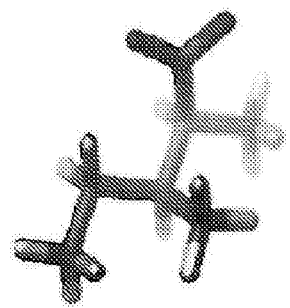
FIG. 11 demonstrates the Rosetta energy function used to score and/or select engineered mosaic antigenic polypeptides. The native conformation is usually the lowest energy conformation.
Figure 12:
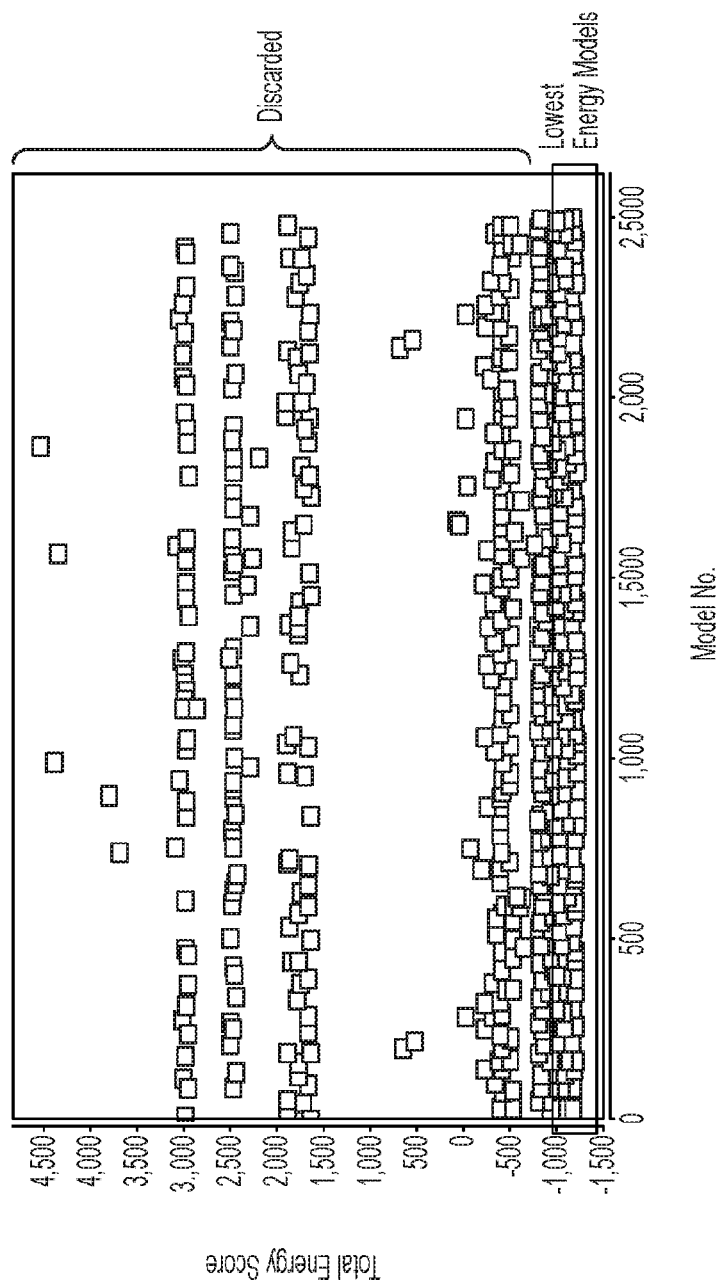
FIG. 12 shows an exemplary scatter plot of total energy score vs model number. The lowest energy models are selected for further screening, analysis, and development.

The insertion of epitopes into the 3D structure of the backbone molecule was performed using the design protocol of the Rosetta molecular modeling software version 3.1 (Simons et al. J. Mol. Biol. 1997 268:209-225; Leaver-Fay et al. Methods Enzymol. 2011 487:545-574). Following epitope insertion, the total energies of the resulting designed molecules were calculated using the Rosetta energy function shown in FIG. 11. Molecules with negative total energy scores were predicted to have a good probability of folding into stable proteins while those with positive energy scores were considered less likely to fold properly. FIG. 12 shows a scatter plot of energy score vs the model number of computationally predicted SMARt structural models. For clarity, only the top scoring 2,500 out of a total of 17,500 modeled structures are displayed on the plot.

Of the 17,500 structural models generated, one hundred lowest energy models were shortlisted for experimental testing. Fifty of the short-listed candidates were prioritized for experimental validation to assess stable soluble expression, proper folding and immunogenicity (Table 6). Thus, the approaches described above yielded novel hemagglutinin molecules for the Influenza B lineage strains that do not match naturally occurring strains. These novel sequences are designed to provide broader coverage to naturally occurring strains than existing vaccine strains (including being cross-protective across the two antigenically distinct lineages). The resulting vaccine candidates can be further modified by targeted engineering of the sequence (including engineering glycosylation patterns, modifying stability or modifying specific epitopes).

TABLE 6

| B/Bris/60/08 | B/Mass/02/12 | B/HK/330/01 | B/Sing/222/79 | B/Yam/16/88 |
|---|---|---|---|---|
| br08_CH | ma12_CH | hk01_RA83 | sing79_CO1 | yam88_DO1 |
| br08_CO1 | ma12_CO1 | B/Pan/45/90 | sing79_DO1 | yam88_RA25 |
| br08_DO1 | ma12_DO2 | pan90_DO2 | sing79_RA101 | yam88_RA39 |
| br08_DO2 | ma12_DO3 | pan90_ | sing79_RA103 | yam88_RA68 |
| br08_DO3 | ma12_RA102 | RA101 | sing79_RA26 | yam88_RA86 |
| br08_RA45 | ma12_RA26 | pan90_RA17 | sing79_RA34 | B/Vic/87 |
| br08_RA51 | ma12_RA33 | pan90_RA20 | sing79_RA41 | vic87_DO2 |
| br08_RA65 | ma12_RA40 | pan90_RA3 | sing79_RA57 | |
| br08_RA8 | ma12_RA46 | pan90_RA35 | sing79_RA68 | |
| B/HK/05/72 | ma12_RA65 | pan90_RA82 | sing79_RA74 | |
| hk72_CH | ma12_RA67 | pan90_RA83 | sing79_RA75 | |
| hk72_DO3 | ma12_RA81 | | sing79_RA76 | |
| | ma12_RA82 | | sing79_RA80 | |
| | ma12_RA97 | | | |

SMARt Design Guided Engineered Soluble Recombinant HA (rHA)

Figures 13, 14:
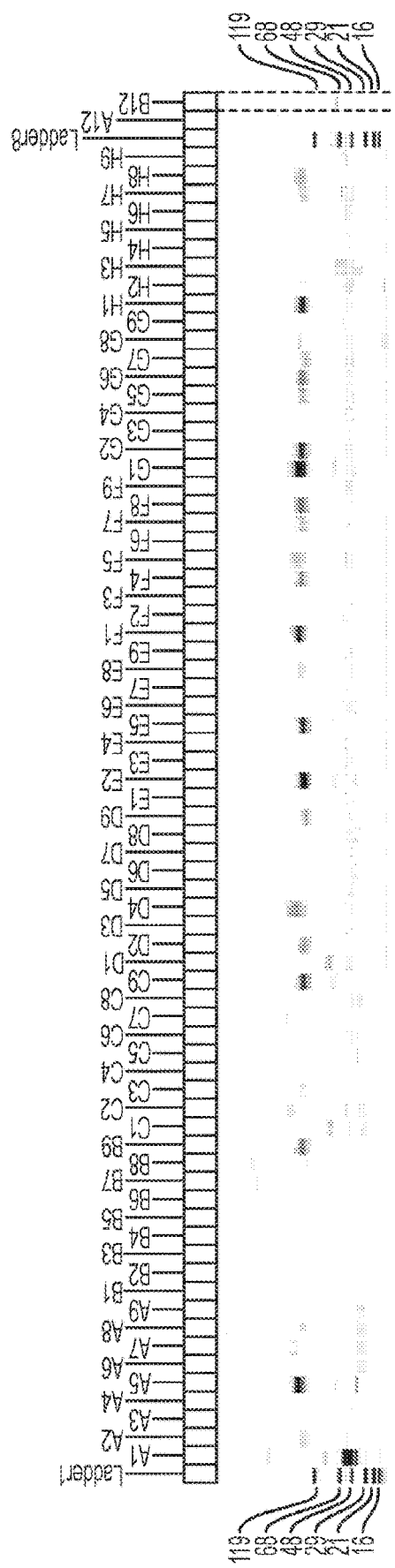
FIG. 13 shows a schematic of the re-engineered transmembrane and cytoplasmic domains which have been replaced to facilitate soluble expression in a mammalian host compatible with a Protein Expression and Purification Platform (PEPP) system.
FIG. 14 shows the expression of re-engineered influenza B HA designs. Approximately half of the recombinant HAs tested were expressed above threshold in a range from 41-320 µg/ml.

Fifty soluble versions of the Influenza B SMARt HA proteins were synthesized, expressed and purified from HEK293 cells using the protein expression and purification platform (PEPP). SMARt HA designs were engineered as full-length trimeric HA proteins. Designs were modified for expression of soluble recombinant protein by replacement of the transmembrane region and cytoplasmic domain with thrombin cleavage site, foldon trimerization domain and his-tag. (FIG. 13). Approximately 50% of the novel designs were purified as soluble versions (FIG. 14).

In Vitro Recognition of PEPP Influenza B rHAs

Figure 15:
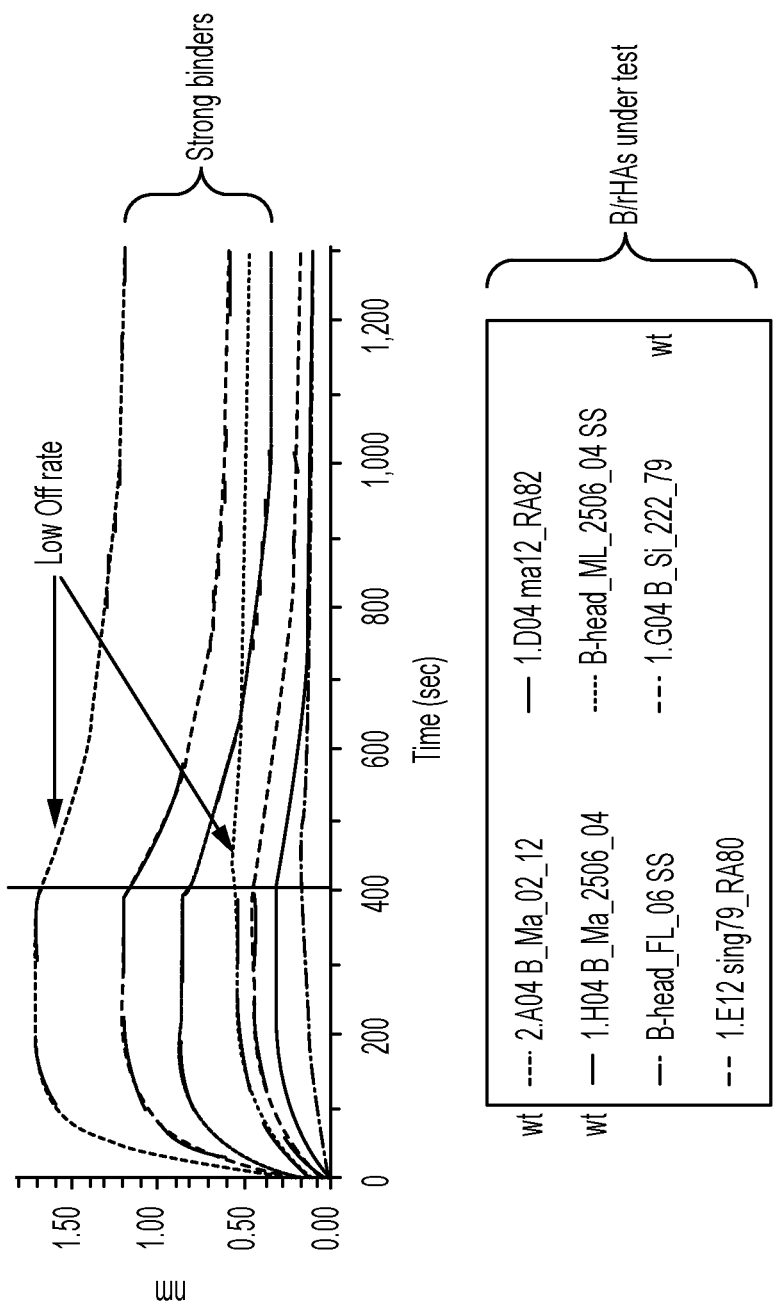
FIG. 15 shows verification of representative influenza B rHAs recognition by an anti-influenza B HA monoclonal antibody. Verification of binding to conformational epitopes was performed using Bio-Layer Interferometry (BLI) using a ForteBio Octet instrument. A low off-rate indicated by the shape of the curve suggests stronger binding of the rHA to the monoclonal antibody as opposed to a quick fall off which would indicate weaker binding.

Purified, soluble Influenza B SMARt HAs were evaluated for their ability to bind Influenza B-specific monoclonal antibodies. Using the ForteBio Octet system, verification of binding to conformational epitopes is performed at a single concentration. Several of these engineered mosaic antigens are able to bind Influenza B specific monoclonal antibodies indicating that the molecules are well-folded (and likely functional). A representative data set demonstrating positive binding of wild type and engineered rHAs to an influenza B monoclonal antibody is shown in FIG. 15.

Example 2. Structural Mapping of Antigenic Repertoires (SMARt) Workflow

One rational design approach to creating a broadly protective HA-based vaccine is to include epitopes from as many viral isolates as possible in a polyvalent vaccine. The methodology behind the generation of mosaic B-cell epitope sequences is termed SMARt for the 'Structural Mapping of Antigenic Repertoires'. The first stage of SMARt relies on the identification and classification of known B-cell epitopes for the influenza A hemagglutinin molecule. The epitopes and antigenic sites for Influenza A hemagglutinin were subdivided into three classes (tiers): 1) epitopes supported by 3D-structural mapping of the contact sites from neutralizing antibodies; 2) neutralizing epitopes not supported by 3D mapping of contact sites; and 3) classical antigenic regions that lack precise mapping of epitope residues. A polyvalent vaccine with M proteins supports the inclusion of M epitope sequence patterns for each epitope site. Each epitope site with N unique epitope sequences has multiple possible combinations of subsets of M unique epitope sequence patterns:

$$C_M^N = \frac{N!}{M!(N-M)!}$$

This was reduced to M subsets, or cassettes, per epitope site by creating a cassette for each unique epitope sequence pattern and optimizing the selected epitope sequence patterns to optimize alignment coverage. There were M possible cassettes for R epitopes sites, creating $R^M$ possible combinations. Mosaic sequence templates were generated for large numbers of random combinations of cassettes to sample a subset of the $R^M$ possible combinations. The alignment coverage for nine geographic regions, viral isolate years, and sub-family clusters was evaluated for each mosaic sequence template. The set of mosaic sequence templates were then combined with target backbone sequence(s) and subjected to structural refinement to generate candidate mosaic polyvalent sequences for vaccine development.

A low fidelity polymerase enables viruses to evolve over multiple generations to evade immunological memory of hosts. This creates a diverse population of related viruses. Vaccines developed to target specific viral isolates may not protect against infection from different isolates of the same virus. The SMARt approach for developing broadly protective antigens creates polyvalent mosaic sequences that include B-cell epitopes from as many viral isolates as possible. Starting with known neutralizing antibody epitopes and antigenic sites, SMARt identifies corresponding antigenic repertoires ($A_{1-N}$, $B_{1-N}$, $C_{1-N}$, ...) from an alignment of N sequences and generates combinations ($A_{23}$, $B_{12}$, $C_{55}$, ... ; $A_{15}$, $B_{38}$, $C_{27}$, ...) from the repertoires to create sets of M mosaic sequences. To optimize the epitope sequence patterns selected, an ordered subset of M epitope sequence patterns were generated for each unique epitope sequence pattern with order optimized for alignment coverage. For each unique epitope sequence pattern, additional epitope sequence patterns ($E_k$, $E_m$, ...) from the same epitope site were selected to maximize the alignment coverage using a scoring matrix (e.g., blosum80.mat). Ordered epitope sequence patterns cassettes from different epitope sites were randomly combined to create large numbers of mosaic template sequences (e.g., for classical antigenic sites, Ca, Cb, Sa, and Sb [Igarashi, et al., 2009]: $Ca1_i$, $Ca2_j$, $Cb_k$, $Sa_l$, $Sb_m$, ... represents the selected cassettes for one mosaic template set of sequences).

To avoid over-representation biases in the available sequences, principal component analysis (PCA) was used to define virus sub-family clusters. The best mosaic sequence templates were selected by evaluating overall alignment coverage by geographic regions, viral isolate years, and PCA clusters. The selected set of mosaic template sequences were combined with target backbone sequences to generate the set of full-length mosaic protein sequences. Structure refinement of these mosaic sequences yields the final set of vaccination proteins. An overview of the mosaic approach is shown in FIG. 16.

Create Multiple Sequence Alignment

All available full-length hemagglutinin protein sequences were downloaded from the NCBI's Influenza Virus Resource (http://www.ncbi.nlm.nih.gov/genomes/FLU/FLU.html) (Bao et al., 2008). Full-length sequences were sub-divided for host and virus sub-type. For the construction of mosaic antigens a host range restriction to human was applied to each dataset. In the case of the human H1N1 viral sub-type sequences, x number of sequences were available as of Apr. 13 2011. Redundant sequences were removed using CDHIT (Fu et al., 2012, CD-HIT: accelerated for clustering the next-generation sequence data, Bioinformatics, 28 (23):3150-3152; Weizhong and Dodzik, 2006, Cd-hit: a fast program for clustering and comparing large sets of protein or nucleotide sequences, Bioinformatics, 22(13): 1658-1659; Weizhong et al., 2002, Tolerating some redundancy significantly speeds up clustering of large protein databases, Bioinformatics, 18(1):77-82; Weizhong et al., 2001, Clustering of highly homologous sequences to reduce the size of large protein databases, Bioinformatics, 17(3): 282-283) and sequences containing ambiguous residues (X, J, B, Z) were excluded to yield a final, non-redundant set of 2043 H1N1 hemagglutinin sequences. The non-redundant sequences were initially aligned MAFFT (e.g., see Katoh and Standley, 2013, Mol. Biol. Evol. 30(4):772-780, or Kotoh et al., 2002, Nucleic Acids Res. 30:3059-3066) and then manually reviewed and edited as required. The manually edited multiple sequence alignment was used for the identification of sequence clusters and for the construction of mosaic sequences.

Identify Epitopes for Target Protein of Interest

Target human B-cell antibody epitopes were identified from crystal structures of hemagglutinin with neutralizing antibodies (Table 2), the Immune Epitope Database (IEDB; Yang, et al., 2009), and antigenic sites from literature (Igarashi et al., 2010). Linear and discontinuous epitopes were organized into a text file format based on the IEDB epitope export Excel file format. Identified epitopes were classified on the basis of supporting publications and structural models into one of three tiers. Tier 1 consists of neutralizing epitopes for which 3D structural models of antigen-antibody contact sites were available. Tier 2 of epitopes includes neutralizing epitopes not supported by 3D structural models. And, tier 3 includes the classical antigenic regions which lack precise characterization of epitope regions.

Figures 17A, 17B:
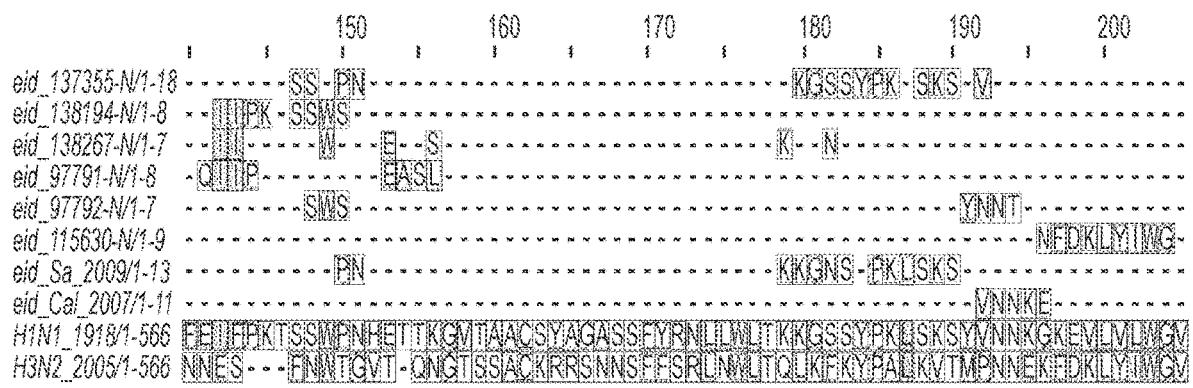
FIG. 17A shows an exemplary comparison of overlapping H1N1 HA epitopes.
FIG. 17B shows an exemplary alignment of overlapping H1N1 HA epitopes.

Antigenic regions can have overlapping epitopes (FIGS. 17A and 17B). Epitope sites for 97823, 97824, and 99799 (IEDB numbering) were nearly identical. The residue positions for 97823 were a subset of the positions for 97824. Epitope 97844 has $N_{35}$, $L_{36}$, and $D_{46}$ not covered by 99799 and 9799 has $V_{364}$ not covered by 97824. For overlapping epitope, the order in which the epitopes were layered into the mosaic templates is important. The residues in the mosaic sequences were determined by the order that the epitopes were added to the templates. For two or more overlapping epitopes, residue positions defined by previously added epitopes mask a subset of the positions for the subsequently added overlapping epitopes. One alternative is to allow the ordered layering of overlapping epitope sequence patterns that were derived from different source viral isolates resulting in mosaic sequences with hybrid epitopes not reflected in the viral isolates in the alignment. Alternatively, overlapping epitopes can be combined and selected consistently from the same viral isolates. For example, adding V364 from 99799 with 97824 generates a combined antigenic site for 97823, 97824, and 99799 (FIG. 17A). Similarly, epitopes 137355, 138194, 138269, and 97791 can be combined into one or two combined sites (FIG. 17B). This second approach was used to resolve overlapping epitopes.

Antigenic Repertoires Identification

Figure 18:
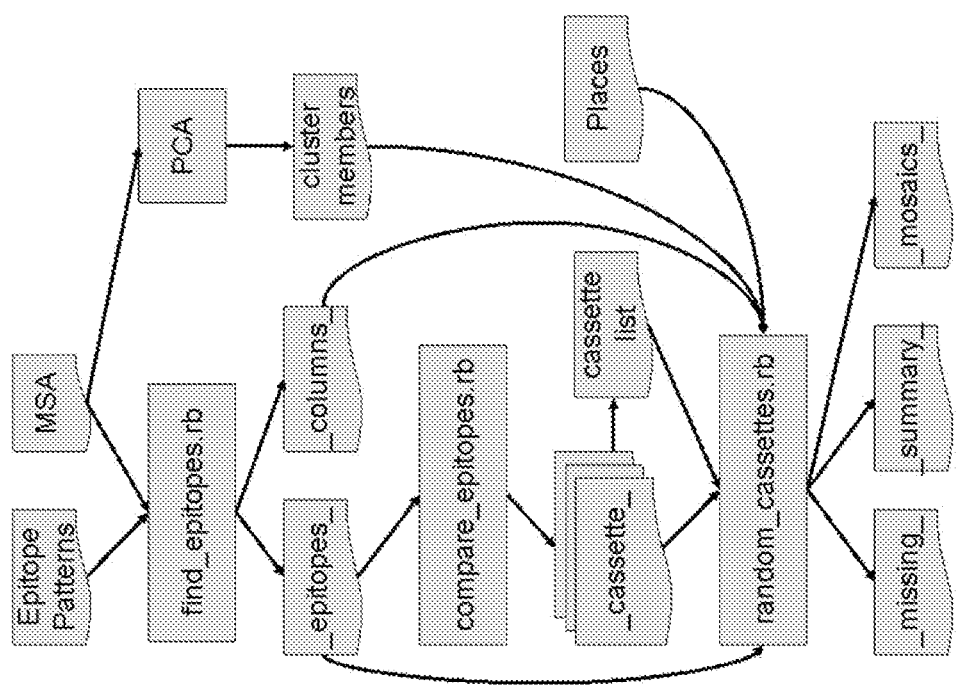
FIG. 18 shows an exemplary flowchart for the design and production of engineered mosaic antigenic polypeptides using the random epitopes process.

To identify corresponding sequence patterns in an epitope across multiple strains, a multiple sequence alignment was searched with linear and discontinuous epitopes. When an epitope or antigen site could be identified within the alignment, the corresponding alignment positions were used for all sequences in the alignment to identify all epitope sequence patterns. For linear epitope peptides with no perfect matches in the alignment, limited sequence mismatches (formula: maximum number of mismatches allowed was (linear site length—5)/2) were permitted. The set of unique epitope sequence patterns was identified for each epitope site. An exemplary flow chart of mosaic sequence generation is shown in FIG. 18.

Cassette Subsets of Unique Epitope Sequence Patterns

SMARt supports the development of polyvalent vaccines with varying numbers of mosaic constructs. A total of M unique epitope sequence patterns for each epitope site can be included in a polyvalent vaccine of M mosaic proteins. A cassette for each unique epitope pattern can be generated (for example, computationally generated) by adding additional epitope sequence patterns in an alignment coverage optimization order. A cassette was created for each unique epitope sequence with that sequence being the first in the cassette. Additional sequence patterns from the same site were added to each cassette by selecting the next sequence pattern with maximum alignment coverage determined with a scoring matrix (e.g., blosum80). Up to 20 unique sequence patterns were added to each cassette.

Create Mosaic Templates from Cassettes

Sets of mosaic template sequences were generated by randomly combining cassettes (e.g., $Ca1_i$, $Ca2_j$, $Cb_k$, $Sa_l$, $Sb_m$, ...). The $i^{th}$ epitope sequence pattern in each cassette was layered onto the $i^{th}$ mosaic template in each set.

Evaluate Alignment Coverage of Mosaic Epitope Templates

Figure 19:
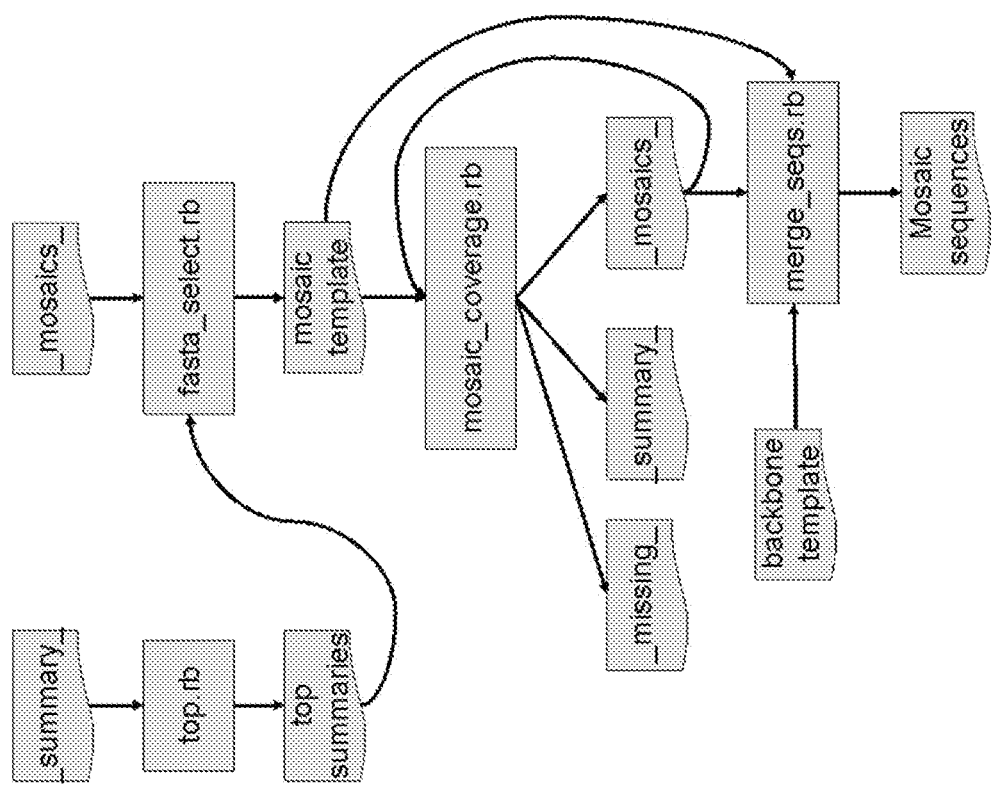
FIG. 19 shows an exemplary flowchart for the design and production of engineered mosaic antigenic polypeptides using the mosaic coverage process.

To avoid potential biases, inherent in the sequence datasets, alignment coverage for viral isolation years, viral geographic regions (Table 6), and sub-family clusters were all evaluated. Multiple sequence alignment coverage by each set of mosaic template sequences was characterized by exact matches of epitope sequence patterns within the alignment. To optimize the selection of the best combinations of epitope cassettes, only the first five mosaic template sequences were used in the evaluation of alignment coverage. Also, only the first five tier 1 epitopes were evaluated in the calculation of alignment coverage to keep the coverage calculations below 100% for the mosaic templates. The best mosaic templates were evaluated by selecting the highest coverage mosaics from the coverage summary. The best set of mosaic templates were extracted from the very large file of mosaic template sequences. An exemplary flowchart of the process overview is shown in FIG. 19.

TABLE 6

| Geographic Region | Number of Isolates |
| --- | --- |
| Africa | 27 |
| Asia | 136 |
| China | 103 |
| Europe | 186 |
| Japan | 72 |
| Middle East | 36 |
| North America | 184 |
| Oceania | 42 |
| South America | 58 |

Epitope Sequence Pattern Swapping Optimization

To further optimize the best mosaic template sequences set, the epitope sequence patterns within the mosaic templates can be modified and the mosaic templates regenerated. For the epitope sequence patterns in the first of the mosaic sequence templates, nine alternative sequence patterns were substituted for each of the five scored epitopes to evaluate possible alignment coverage improvements.

Combine Mosaic Epitope Template with Target Backbone Templates

The mosaic epitope sequence templates can be combined with desired viral protein backbone sequence(s).

Structure Refinement

The mosaic sequences were checked for structural consistency using structural bioinformatics tools. High-resolution three-dimensional structures of HA molecules were used as the template for generating the structural backbones into which epitope repertoires were inserted. The insertion of epitopes into the 3D structure of the backbone molecule was performed using the design protocol of the Rosetta molecular modeling software version 3.1 (Simons et al. J. Mol. Biol. 1997 268:209-225; Leaver-Fay et al. Methods Enzymol. 2011 487:545-574). Following epitope insertion, the total energies of the resulting designed molecules were calculated. Molecules with negative total energy scores were predicted to have a good probability of folding into stable proteins while those with positive energy scores were considered less likely to fold properly and were therefore discarded. Sequences of the one hundred lowest energy models were shortlisted for experimental testing.

Results

Figure 20:
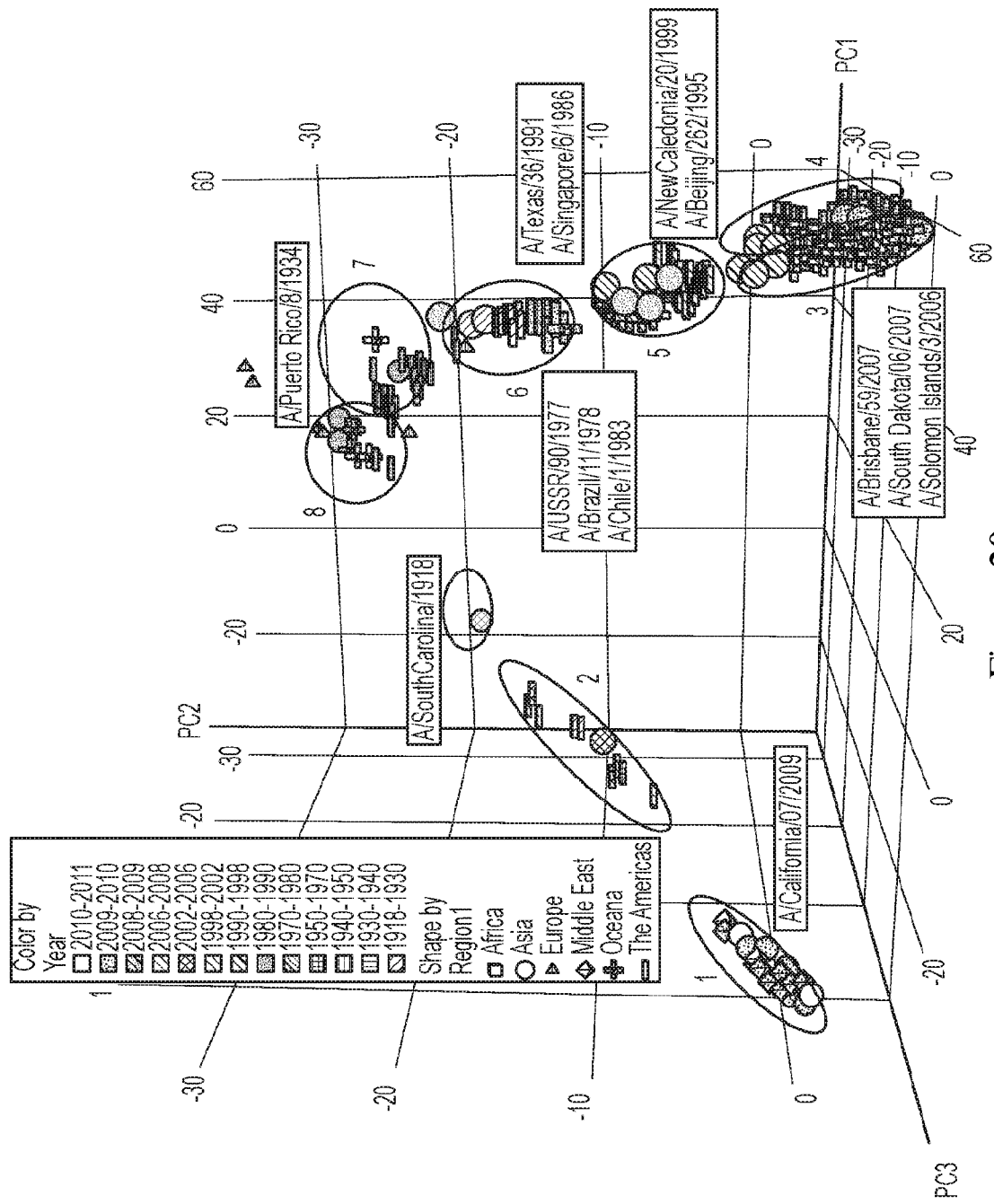
FIG. 20 shows an exemplary principal component analysis plot used to identify H1N1 HA clusters.

Principal component analysis (PCA) was used to separate the H1N1 hemagglutinin sequences into eight unevenly distributed sub-family clusters (FIG. 20). Clusters 1, 3, and 4 were well represented and clusters 2, 7, and 8 were sparsely represented (Table 8).

Evaluating all possible combinations of unique epitope sequence patterns for multiple epitope sites is an N-P complete complexity computational problem. Sampling random combinations of cassettes enables the evaluation of a subset of all possible combinations. Millions of random combinations were generated and the combinations with the highest coverage of the alignment were examined. Top combinations identified are illustrated in Table 8.

TABLE 8

| Mosaic | Regions | Years | Clusters | Cluster 2 | Cluster 7 | Cluster 8 |
| --- | --- | --- | --- | --- | --- | --- |
| HC578810 | 98% | 90% | 93% | 10/13 (77%) | 20/24 (84%) | 15/18 (84%) |
| HB949180 | 98% | 89% | 92% | 8/13 (61%) | 20/24 (84%) | 16/18 (89%) |
| ID316526 | 98% | 89% | 92% | 8/13 (61%) | 20/24 (84%) | 16/18 (89%) |
| JE56022 | 98% | 89% | 92% | 8/13 (61%) | 20/24 (84%) | 16/18 (89%) |

Conclusions

The SMARt approach enables the sampling of the known antigenic repertoires in mosaic sequences with promising potential for generating broadly protective vaccines.

Example 3. In Vivo Efficacy of Engineered Mosaic Influenza A HA and NA Polypeptides This Example illustrates that engineered HA polypeptide made in accordance with the previous examples elicited immune responses in the form of broad antibody responses against several influenza strains.

Preparation of Virus-Like Particles (VLPs) Containing Engineered Mosaic Hemagglutinins (HAs)

Influenza VLPs were prepared by three-plasmid transient transfection of HEK293T cells in serum-free Freestyle293 medium. Plasmids encoding engineered mosaic Influenza HA polypeptide sequence as well as those for NA, and HIVgag were mixed at 1:1:1 ratio and used to transiently transfect the HEK293T cells. Culture supernatant was harvested 120 hours post-transfection and VLPs in the supernatant were pelleted by ultracentrifugation over a 20% sucrose cushion and resuspended in PBS.

Immunization of Mice with VLPs Expressing Engineered Mosaic HAs

To assess immunogenicity of engineered mosaic HA designs, groups of 6-8 week old female BALB/c mice were immunized with 5 μg of influenza VLPs or vehicle alone (PBS). All immunizations were formulated as emulsions with an oil-in-water adjuvant, and were delivered subcutaneously in a total volume of 100 μl. Each group received an identical booster dose 21 days after the initial immunization. Pre-immune and post-immune serum was collected from each animal on days 0 and 35, respectively. Serum pools used for analysis were prepared by mixing equal volumes of serum from each animal within a group.

Hemagglutination Inhibition (HAI) Assay

Figure 21:
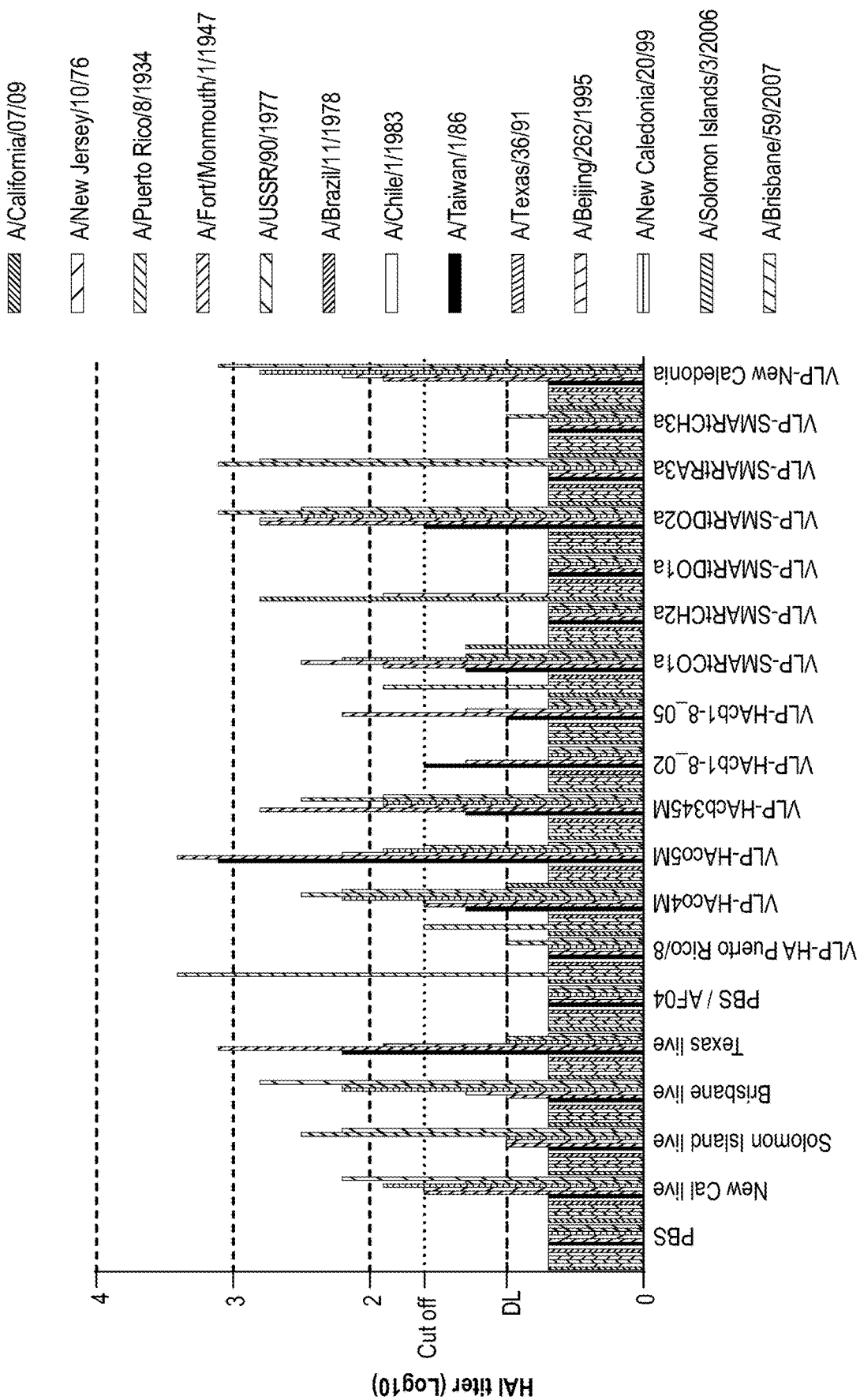
FIG. 21 shows representative serum titer induced against H1N1 influenza strains as measured in a hemagglutination inhibition (HAI) assay for selected engineered VLPs. Animals were immunized as described in Example 3 and serum collected on day 35 (14 days after boosting dose) was analyzed for its ability to inhibit hemagglutination mediated by various H1N1 influenza strains. Titer is defined as the maximum serum dilution resulting in complete inhibition of hemagglutination in 50% of the wells assayed. Each bar represents the virus-specific serum HAI titer induced by selected influenza VLPs or vehicle. The dotted line (DL) on the graph represents a 1:40 HAI titer, which is known as the minimum HAI titer required for protection against a given influenza strain.

Replicate serial dilutions of pooled serum from each group were mixed with 4 hemagglutination units of the indicated virus and incubated at room temperature for 30 minutes in a round bottom plate. Each serum/virus mixture was then mixed with an equal volume of 0.5% turkey erythrocytes in saline. The plates were scored when control wells lacking serum demonstrated complete hemagglutination (~30 min). The HAI titer was defined as the maximum serum dilution resulting in complete inhibition of hemagglutination in 50% of the wells tested. FIG. 21 sets forth representative serum HAI titer induced against H1N1 influenza strains for engineered mosaic VLPs.

Microneutralization (MN) Assay

Figure 22:
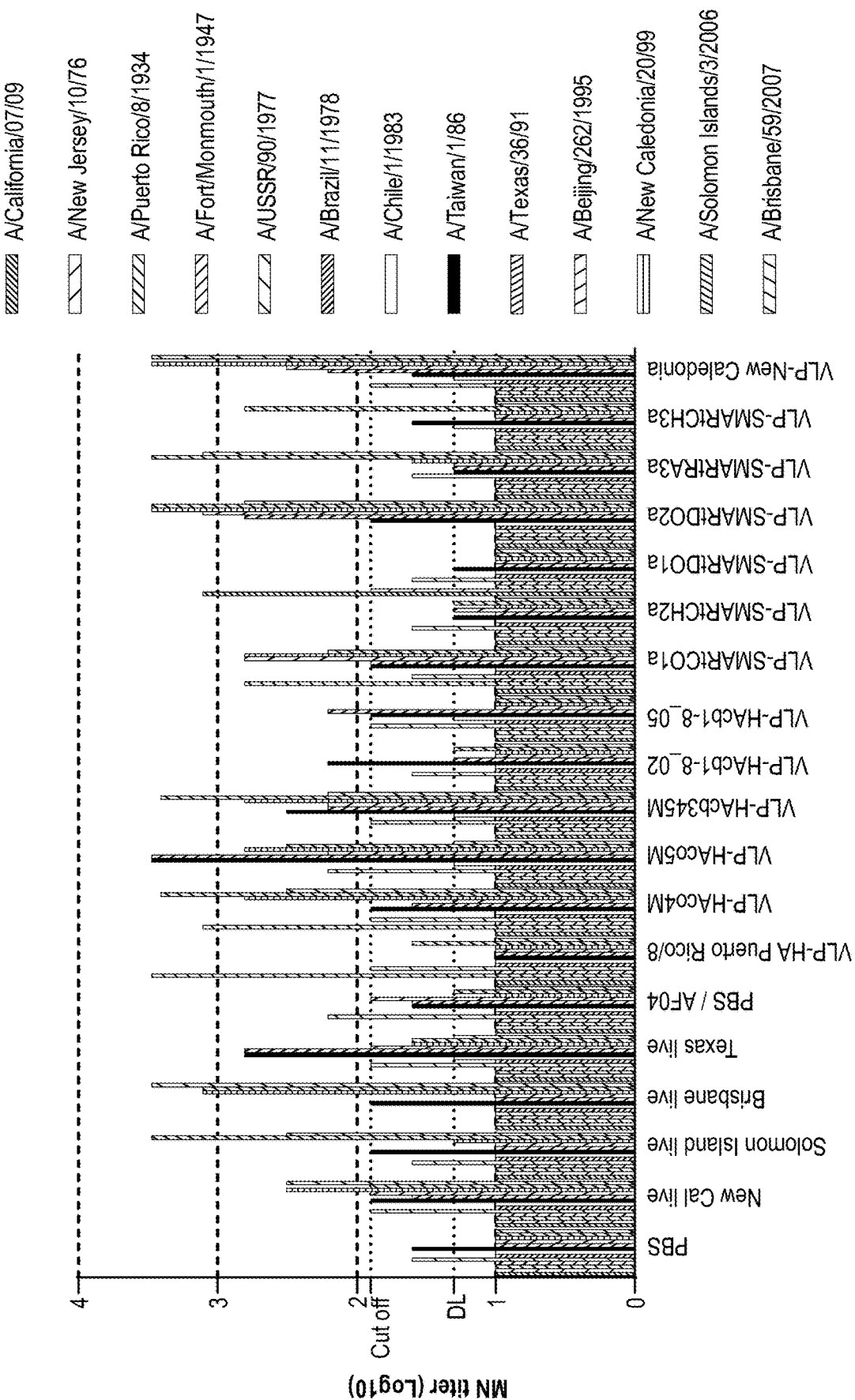
FIG. 22 shows representative serum titer induced against H1N1 influenza strains as measured in a microneutralization (MN) assay for selected engineered VLPs. Animals were immunized as described in Example 3 and serum collected on day 35 (14 days after the boosting dose) was analyzed for its ability to block infection with various H1N1 influenza strains. The MN titer is defined as the maximum serum dilution resulting in complete inh chain is comprised of two domains—an amino-terminal variable ($V_L$) domain, followed by a carboxy-terminal constant ($C_L$) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the $C_H2$ domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. Amino acid sequence comparisons among antibody polypeptide chains have defined two light chain ($\kappa$ and $\lambda$) classes, several heavy chain (e.g., $\mu, \gamma, \alpha, \epsilon, \delta$) classes, and certain heavy chain subclasses ($\alpha1, \alpha2, \gamma1, \gamma2, \gamma3,$ and $\gamma4$). Antibody classes (IgA [including IgA1, IgA2], IgD, IgE, IgG [including IgG1, IgG2, IgG3, IgG4], IgM) are defined based on the class of the utilized heavy chain sequences. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is monoclonal; in some embodiments, an antibody is polyclonal. In some embodiments, an antibody has constant region sequences that are characteristic of mouse, rabbit, primate, or human antibodies. In some embodiments, an antibody sequence elements are humanized, primatized, chimeric, etc., as is known in the art. Moreover, the term "antibody" as used herein, will be understood to encompass (unless otherwise stated or clear from context) can refer in appropriate embodiments to any of the art-known or developed constructs or formats for capturing antibody structural and functional features in alternative presentation. For example, in some embodiments, the term can refer to bi- or other multi-specific (e.g., zybodies, etc.) antibodies, Small Modular ImmunoPharmaceuticals ("SMIPs™"), single chain antibodies, camelid antibodies, and/or antibody fragments. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc.], or other pendant group [e.g., poly-ethylene glycol, etc.]).

Replicate serial dilutions of pooled serum from each group were mixed with 100 50% tissue culture infectious doses (TCID50) of the indicated virus and incubated at 37° C. for one hour. Each serum/virus mixture was then added to confluent monolayers of madin darby canine kidney (MDCK) cells and incubated at 37° C. for 24 hrs. The monolayers were then fixed and infected wells were identified based on ELISA detection of influenza nucleoprotein. The MN titer was defined as the highest dilution of serum resulting in complete neutralization of virus infection in 50% of the wells tested. FIG. 22 sets forth representative serum MN titer induced against H1N1 influenza strains for engineered mosaic VLPs.

Results

Taken together, these data demonstrate that engineered HA polypeptides as described herein promote broad immunity against H1N1 influenza strains. These exemplary HA polypeptides were developed using a novel computational strategy to create mosaic HA antigens based on conserved repertoires, referred to as SMARt. Exemplary HA polypeptides SP8 and SP9 (Table 9) were presented in the context of an HIVgag VLP to perform immunogenicity studies in murine animals. Exemplary engineered mosaic HA polypeptides induced antibody responses predicted to provide protection against both A/California/07/2009 (the currently circulating H1N1 strain) as well as a historical swine flu strain, A/New Jersey/10/1976. More importantly, SP9 induced a broad antibody response, with significant titers induced against vaccine strains dating back to 1986. These data suggest that a vaccine utilizing the engineered mosaic design (e.g., SP9) may have been sufficient for protection from H1N1 strains circulating between the years of 1986 and 2007. Further, a combined immunization incorporating both SP8 and SP9 HA designs would potentially be effective against all H1N1 viruses that have been in circulation since 1986. Thus, the engineered mosaic HA designs as described herein provide candidate HA polypeptides for use in a universal H1N1 vaccine that can be used alone or in combination to induce immunity against a broad array of H1N1 viruses.

TABLE 9

| Engineered HA | Antigenic Region Sequence |
|---|---|
| SP1 | GVTASSWLTHHPSNGDQQTLKDQEGR (SEQ ID NO: 11) |
| SP2 | GVSASSWLTHHPSTADQQTLKDQEGR (SEQ ID NO: 12) |
| SP3 | GVTASKWLVHHPSTADQQSLKDQEGR (SEQ ID NO: 13) |
| SP4 | GVSASSWLTHHPPNGDQRALKDQEGR (SEQ ID NO: 14) |
| SP5 | GVSASSWLTHHPPNGDQKTLKDQEGR (SEQ ID NO: 15) |
| SP7 | GVSAASWLTHHPSTADQQTLKDQEGR (SEQ ID NO: 16) |
| SP8 | GVTAAKWLVHHPSTADQQSLKDQEGR (SEQ ID NO: 17) |
| SP9 | GVSAASWLTHHPPNGDQRALKDQEGR (SEQ ID NO: 18) |
| SP10 | GVSAASWLTHHPPNGDQKTLKDQEGR (SEQ ID NO: 19) |
| SP1 | CYPTVTGVTASCSKSSFLWLTGVHHPSNIGDQQTLYQEIAKRPKVRDQEGRMNI (SEQ ID NO: 20) |
| SP2 | CYPDVTGVSASCSASSFLWLTKVHHPSTIADQQTLYHEIAIRPKVRDQEGRINI (SEQ ID NO: 21) |

TABLE 9-continued

| Engineered HA Antigenic Region Sequence | |
|---|---|
| SP3 | CYPDSNGVTASCPAKSFLWLVKVHHPSTSADQQSLYQEIAIRPKVR DQEGRMNI (SEQ ID NO: 22) |
| SP4 | CYPTVTGVSASCSKSSFLWLTGVHHPPNIGDQRALYHEIAKRPKVR DQEGRINI (SEQ ID NO: 23) |
| SP5 | CYPTVTGVSASCPESSFLWLTGVHHPPNIGDQKTLYHEIAKRPKVRD QEGRINI (SEQ ID NO: 24) |
| SP6 | CYPTVTKGVTAACSKSSFIWLTGIHEIPSNIGDQQTLYQEIAKRPKVR DQEGRMNV (SEQ ID NO: 25) |
| SP7 | CYPDVTKGVSAACSASSFIWLTKIHEIPSTIADQQTLYHEIAIRPKVRD QEGRINV (SEQ ID NO: 26) |
| SP8 | CYPDSNKGVTAACPAKSFIWLVKIHHPSTSADQQSLYQEIAIRPKVR DQEGRMNV (SEQ ID NO: 27) |
| SP9 | CYPTVTKGVSAACSKSSFIWLTGIHHPPNIGDQRALYHEIAKRPKVR DQEGRINV (SEQ ID NO: 28) |
| SP10 | CYPTVTKGVSAACPESSFIWLTGIHHPPNIGDQKTLYHEIAKRPKVR DQEGRINV (SEQ ID NO: 29) |
| SP1 | LGNPGTCYPGYKWNHTVTGVTASCSHAGKSSFYRNLLWLTGKNGS YPWGVHHPSNIGDQQTLYQTENAFTPEIAKRPKVRDQEGRMNYAN GNLIAPW (SEQ ID NO: 30) |
| SP2 | LGNPGTCYPGYKWNHDVTGVSASCSHNGASSFYRNLLWLTKKNNL YPWGVHHPSTIADQQTLYHTENAFTPEIAIRPKVRDQEGRINYANGN LIAPW (SEQ ID NO: 31) |
| SP3 | LGNPGTCYPGYKWNHDSNGVTASCPHAGAKSFYRNLLWLVKKGN SYPWGVHHPSTSADQQSLYQNANAFTPEIAIRPKVRDQEGRMNYAT GNLIAPW (SEQ ID NO: 32) |
| SP4 | LGNPGTCYPGYKWNHTVTGVSASCSHNGKSSFYRNLLWLTGKNGL YPWGVHHPPNIGDQRALYHTENAFTPEIAKRPKVRDQEGRINYANG NLIAPW (SEQ ID NO: 33) |
| SP5 | LGNPGTCYPGYKWNHTVTGVSASCPHNGESSFYRNLLWLTGKNGL YPWGVHHPPNIGDQKTLYHTENAFTPEIAKRPKVRDQEGRINYANG NLIAPW (SEQ ID NO: 34) |
| SP6 | LGNPGTCYPGDKWNHTVTKGVTAACSHAGKSSFYKNLIWLTGKNG SYPWGIHHPSNIGDQQTLYQTEDTFKPEIAKRPKVRDQEGRMNYAN GNLVVPR (SEQ ID NO: 35) |
| SP7 | LGNPGTCYPGDKWNHDVTKGVSAACSHNGASSFYKNLIWLTKKN NLYPWGIHHPSTIADQQTLYHTEDTFKPEIAIRPKVRDQEGRINYAN GNLVVPR (SEQ ID NO: 36) |
| SP8 | LGNPGTCYPGDKWNHDSNKGVTAACPHAGAKSFYKNLIWLVKKG NSYPWGIHHPSTSADQQSLYQNADTFKPEIAIRPKVRDQEGRMNYA TGNLVVPR (SEQ ID NO: 37) |
| SP9 | LGNPGTCYPGDKWNHTVTKGVSAACSHNGKSSFYKNLIWLTGKNG LYPWGIHHPPNIGDQRALYHTEDTFKPEIAKRPKVRDQEGRINYAN GNLVVPR (SEQ ID NO: 38) |

TABLE 9-continued

Engineered HA Antigenic Region Sequence

SP10        LGNPGTCYPGDKWNHTVTKGVSAACPHNGESSFYKNLIWLTGKNG
            LYPWGIHHPPNIGDQKTLYHTEDTFKPEIAKRPKVRDQEGRINYANG
            NLVVPR
            (SEQ ID NO: 39)

Example 4. In Vivo Efficacy of Engineered Mosaic Influenza B HA Polypeptides

This Example illustrates that engineered HA polypeptides made in accordance with the previous examples elicited immune responses in the form of broad antibody responses against several influenza B strains.

Immunization of Mice with rHAs

Soluble influenza B SMARt HAs have been used to immunize mice. Mice were immunized three times (Day 0, Day 21, Day 42) with soluble rHA mixed 1:1 with AF03 (adjuvant) [the soluble proteins were used at the concentration and purity of the material produced on the PEPP system; no additional purification or concentration steps were performed]. 27 groups containing 3 mice each were tested as shown in Table 10.

TABLE 10

| Group | n[1] | Immunization (Day 0, 21, 42) | Rationale |
|---|---|---|---|
| 1 | 3 | PBS | Negative Control |
| 2 | 3 | HA[br08_CH] | |
| 3 | 3 | HA[br08_CO1] | |
| 4 | 3 | HA[br08_DO1] | |
| 5 | 3 | HA[br08_DO2] | |
| 6 | 3 | HA[br08_DO3] | |
| 7 | 3 | HA[br08_RA65] | |
| 8 | 3 | HA[br08_RA8] | |
| 9 | 3 | HA[hk72_CH] | |
| 10 | 3 | B/MASS/12 IIV | Positive Control |
| 11 | 3 | HA[ma12_RA82] | |
| 12 | 3 | HA[pan90_DO2] | |
| 13 | 3 | HA[pan90_RA20] | |
| 14 | 3 | HA[sing79_DO1] | |
| 15 | 3 | HA[sing79_RA103] | |
| 17 | 3 | HA[sing79_RA80] | |
| 18 | 3 | HA[yam88_DO1] | |
| 19 | 3 | HA[B_Lee_40] | Wild-type |
| 20 | 3 | HA[B_HK_05_72] | Wild-type |
| 21 | 3 | HA[B_Si_222_79] | Wild-type |
| 22 | 3 | HA[B_Ya_16_88] | Wild-type |
| 23 | 3 | HA[B_Pa_45_90] | Wild-type |
| 24 | 3 | HA[B_Ma_2506_04] | Wild-type |
| 25 | 3 | HA[B_Br_60_08] | Wild-type |
| 26 | 3 | HA[B_Wi_01_10] | Wild-type |
| 27 | 3 | HA[B_Ma_02_12] | Wild-type |
| 28 | 3 | rHA[CA09] | CA/09 HA-Negative Control for HAI against B |

Hemagglutination Inhibition (HAI) Assay

Figure 23:
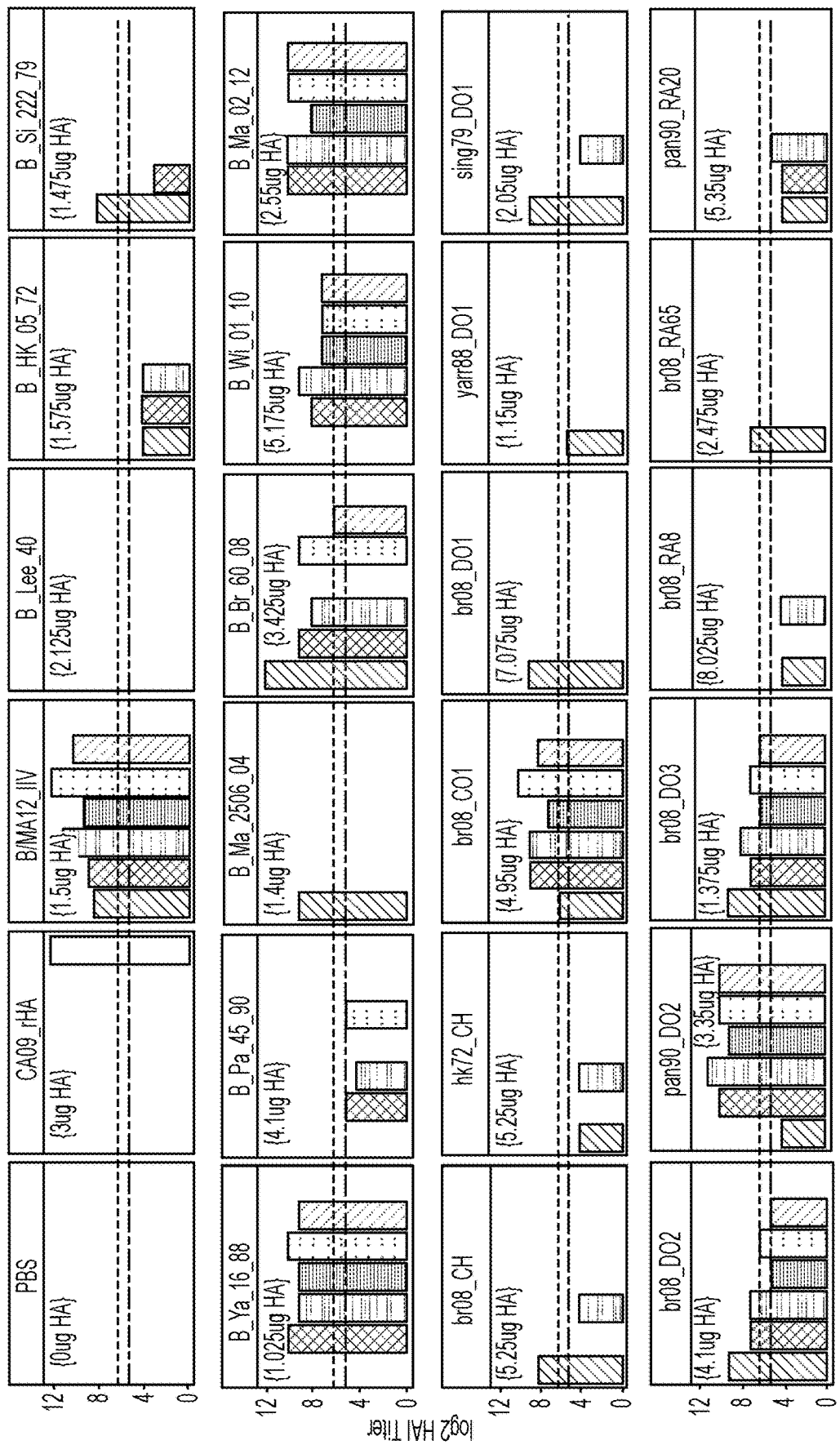
Figure 23:
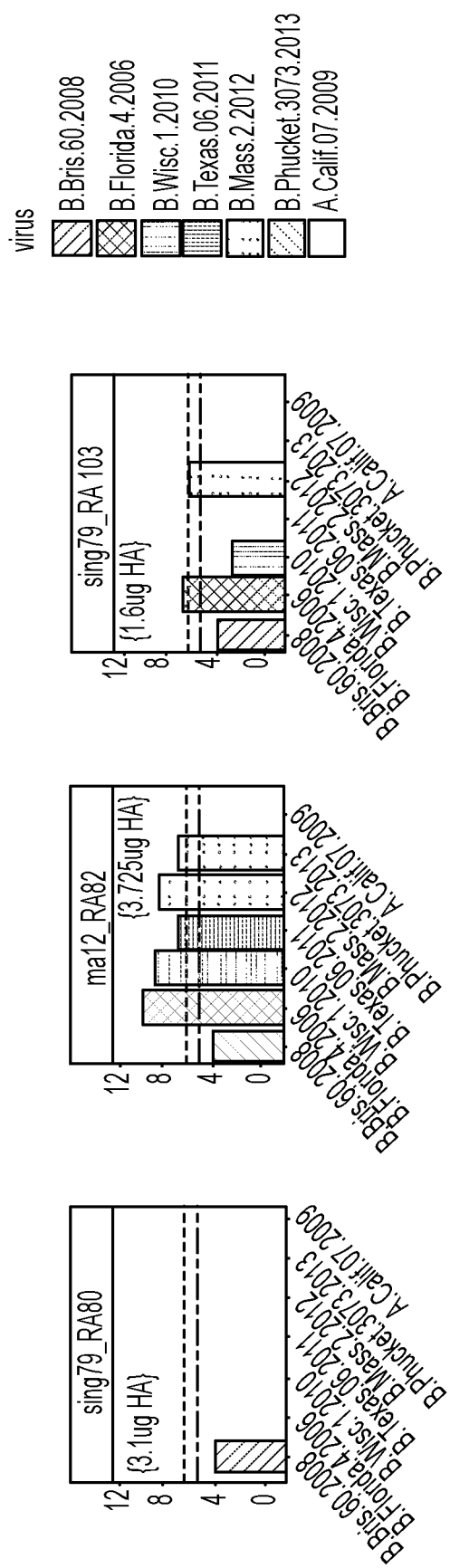

Terminal bleeds were taken on D56 and evaluated by HAI to a panel of Influenza B viruses. The immunogenicity data for these constructs are presented in FIG. 23 and Table 11. 5 of the 15 SMARt HA constructs demonstrated some breadth of response against the Influenza B panel (Note: The current influenza B panel is limited and includes only a single representative of the Victoria lineage; additionally the panel is biased to recent strains]. 3 of the 15 SMARt HA constructs were cross-reactive to the 6 influenza B strains tested (both Yamagata and Victoria lineage). Similar breadth of response was only observed for the B/Massachusetts/ 2012 Inactivated vaccine (IIV); the use of B/Massachusetts/ 2012 recombinant HA was not cross-reactive to the Victoria lineage strain.

TABLE 11

| | [HA] | B/Florida/ 4/2006 | B/Bris/ 60/ 2008 | B/Wisc/ 1/2010 | B/Mass/ 2/ 2012 | B/Texas/ 06/ 2011 | B/Phuket/ 3073/ 2013 | A/Calif/ 07/ 2009 |
|---|---|---|---|---|---|---|---|---|
| PBS | 0 | <10 | <10 | <10 | <10 | <10 | <10 | <10 |
| br08_CH | 5.2 | <10 | 320 | 20 | <10 | <10 | <10 | <10 |
| br08_CO1 | 4.95 | 640 | 80 | 640 | 1280 | 160 | 320 | <10 |
| br08_DO1 | 7.075 | <10 | 640 | <10 | <10 | <10 | <10 | <10 |
| br08_DO2 | 4.1 | 160 | 640 | 160 | 80 | 40 | 40 | <10 |
| br08_DO3 | 1.375 | 160 | 640 | 320 | 160 | 80 | 80 | <10 |
| br08_RA65 | 2.475 | <10 | 160 | <10 | <10 | <10 | <10 | <10 |
| br08_RA8 | 8.025 | <10 | 20 | 20 | <10 | <10 | <10 | <10 |
| hk72_CH | 5.25 | <10 | 20 | 20 | <10 | <10 | <10 | <10 |
| B/MA12_IIV | 1.5 | 512 | 320 | 2560 | 5120 | 640 | 1280 | <10 |
| ma12_RA82 | 3.725 | 1280 | 20 | 640 | 640 | 160 | 160 | <10 |
| pan90_DO2 | 3.35 | 1280 | 20 | 2560 | 1280 | 640 | 1280 | <10 |
| pan90_RA20 | 5.35 | 20 | 20 | 40 | <10 | <10 | <10 | <10 |
| sing79_DO1 | 2.05 | <10 | 640 | 20 | <10 | <10 | <10 | <10 |
| sing79_RA103 | 1.6 | 160 | 20 | 20 | 80 | <10 | <10 | <10 |
| sing79_RA80 | 3.1 | <10 | 20 | <10 | <10 | <10 | <10 | <10 |
| yam88_DO1 | 1.15 | <10 | 40 | <10 | <10 | <10 | <10 | <10 |
| B_Lee_40 | 2.125 | <10 | <10 | <10 | <10 | <10 | <10 | <10 |
| B_HK_05_72 | 1.575 | 20 | 20 | 20 | <10 | <10 | <10 | <10 |
| B_Si_222_79 | 1.475 | 10 | 320 | <10 | <10 | <10 | <10 | <10 |
| B_Ya_16_88 | 1.025 | 1280 | <10 | 640 | 1280 | 640 | 640 | <10 |
| B_Pa_45_90 | 4.1 | 40 | <10 | 20 | 40 | <10 | <10 | <10 |

TABLE 11-continued

| | [HA] | B/Florida/ 4/2006 | B/Bris/ 60/ 2008 | B/Wisc/ 1/2010 | B/Mass/ 2/ 2012 | B/Texas/ 06/ 2011 | B/Phuket/ 3073/ 2013 | A/Calif/ 07/ 2009 |
|---|---|---|---|---|---|---|---|---|
| B_Ma_2506_04 | 1.4 | <10 | 640 | <10 | <10 | <10 | <10 | <10 |
| B_Br_60_08 | 3.425 | 640 | 5120 | 320 | 640 | <10 | 80 | <10 |
| B_Wi_01_10 | 5.175 | 320 | <10 | 640 | 160 | 160 | 160 | <10 |
| B_Ma_02_12 | 2.55 | 1280 | <10 | 1280 | 1280 | 320 | 1280 | <10 |
| CA09_rHA | 3 | <10 | <10 | <10 | <10 | <10 | <10 | 5120 |

Having thus described several aspects of at least one embodiment of this invention, it is to be appreciated that various alterations, modifications, and improvements will readily be apparent to those skilled in the art. Such alterations, modifications, and improvements are intended to be part of this disclosure, and are intended to be within the spirit and scope of the invention. Accordingly, the foregoing description and drawings are by way of example only and the invention is described in detail by the claims that follow.

EQUIVALENTS

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

We claim:

1. An engineered mosaic influenza B hemagglutinin (HA) polypeptide produced by a method comprising
    aligning HA amino acid sequences from multiple circulating strains of a particular type and/or subtype of influenza B virus to generate an alignment;
    identifying positions of amino acids corresponding to epitopes and antigenic regions, or defined set of residue positions;
    compiling amino acid residues across the alignment at the identified positions for epitopes and antigenic regions, or defined set of residue positions thereby generating antigenic repertoires;
    defining a set of amino acid sequence patterns within the antigenic repertoires—for each epitope and antigenic region, or defined set of residue positions, wherein each amino acid sequence pattern in the set is represented only once;
    selecting one or more sequences based on the defined amino acid sequence patterns in the set for each epitope or antigenic region, or defined set of residue positions, thereby resulting in combinations of selected sequences for epitopes and antigenic regions or defined set of residue positions across the alignment according to pre-determined criteria; and
    inserting selected sequences into corresponding locations in a structural backbone of influenza B HA, thereby generating engineered mosaic influenza B HA polypeptides, wherein the engineered mosaic influenza B HA polypeptides are distinct from naturally circulating strains; and
    evaluating each of the engineered mosaic influenza B HA polypeptides based on conformational stability and breadth of coverage across naturally occurring strains;
    wherein the engineered mosaic influenza B HA polypeptide comprises a mosaic amino acid sequence pattern defined by 131H, 159P, 160N, 161A, 162T, 163N, 164K, 165S and 213K as indexed by reference to a B/Brisbane/60/2008 HA.

2. The engineered mosaic influenza B hemagglutinin (HA) polypeptide of claim 1, wherein the mosaic amino acid sequence pattern is further defined by amino acid substitutions at residues 110, 140, 141, 143, 145, 146, 153, 154, 155, 156, 174, 175, 176, 177, 179, 180, 181, 209, 210, 211, 212, 215, 216, 217, 228, 258, 259, 279 or a subset thereof, in the receptor binding site (RBS), as indexed by reference to a B/Brisbane/60/2008 amino acid sequence.

3. The engineered mosaic influenza B hemagglutinin (HA) polypeptide of claim 2, wherein the mosaic amino acid sequence pattern is further defined by amino acid substitutions 110F, 140I, 141D/N, 143E, 145A, 146P, 153G, 154T, 155S, 156G/R, 174A, 175V, 176P, 177K, 179D, 180N/S, 181N, 209H, 210S, 211D, 212N/D, 215Q, 216M, 217K/V, 228F, 258S, 259G, 279Q, or a subset thereof in the receptor binding site (RBS), as indexed by reference to a B/Brisbane/60/2008 amino acid sequence.

4. The engineered mosaic influenza B HA polypeptide of claim 1, wherein the structural backbone is derived from a type B influenza virus selected from
CAA25425|HA|Human|fluB|B/Singapore/222/79|Singapore|1979|,
AGL06036|HA|Human|fluB|B/Massachusetts/02/2012|USA|2012/03/13|,
ABL76694|HA|Human|fluB|B/Panama/45/1990|Panama|1990/03/07|,or
AFH57909|HA|Human|fluB|B/Brisbane/60/2008|Australia|2008|.

5. An isolated nucleic acid molecule encoding an engineered mosaic influenza B HA polypeptide of claim 1.

6. A vector comprising the nucleic acid sequence of claim 5.

7. An isolated cell comprising the vector of claim 6.

8. A fusion protein comprising an engineered mosaic influenza B HA polypeptide of claim 1.

9. A vaccine composition comprising an engineered mosaic influenza B HA polypeptide of claim 1.

10. The vaccine composition of claim 9, wherein the vaccine composition is a split inactivated virus.

11. A method of immunizing a subject against influenza virus, comprising administering to the subject a vaccine composition of claim 9.

12. The engineered mosaic influenza B hemagglutinin (HA) polypeptide of claim 1, wherein the mosaic amino acid sequence pattern is further defined by 128G, 130E, 131H, 133R, 136T/N, 137Q/H/Y, 138N, 173W, 195I, 196C, 197T/A, 198E, 199G, 200E, 213K, 214T, 225P, 227K, 245G/D, 248D/N, 250T, 251E, 257Q, and 277V/T as indexed by reference to a B/Brisbane/60/2008 HA amino acid sequence.

13. The engineered mosaic influenza B hemagglutinin (HA) polypeptide of claim 1, comprising an amino acid sequence that is at least 98% identical to SEQ ID NO:41.

14. An engineered mosaic influenza B hemagglutinin (HA) polypeptide comprising a mosaic amino acid sequence pattern defined by 131H, 159P, 160N, 161A, 162T, 163N, 164K, 165S and 213K as indexed by reference to a B/Brisbane/60/2008 HA.

15. The engineered mosaic influenza B HA polypeptide of claim 14, further comprising 128G, 130E, 133R, 136T/N, 137Q/H/Y, 138N, 173W, 195I, 196C, 197T/A, 198E, 199G, 200E, 214T, 225P, 227K, 245G/D, 248D/N, 250T, 251E, 257Q, and 277V/T as indexed by reference to a B/Brisbane/60/2008 HA amino acid sequence.

16. The engineered mosaic influenza B HA polypeptide of claim 14, comprising an amino acid sequence that is at least 98% identical to SEQ ID NO:41.

17. A fusion protein comprising an engineered mosaic influenza B HA polypeptide of claim 14.

18. A vaccine composition comprising an engineered mosaic influenza B HA polypeptide of claim 14.

19. The vaccine composition of claim 18, wherein the vaccine composition is a split inactivated virus.

20. A method of immunizing a subject against influenza virus, comprising administering to the subject a vaccine composition of claim 18.

* * * * *

UNITED STATES PATENT AND TRADEMARK OFFICE
CERTIFICATE OF CORRECTION

PATENT NO. : 10,844,097 B2
APPLICATION NO. : 16/306346
DATED : November 24, 2020
INVENTOR(S) : Tod Strugnell et al.

It is certified that error appears in the above-identified patent and that said Letters Patent is hereby corrected as shown below:

In the Claims

At Column 199, Line 14, "Australia|20081." should be --Australia|2008|.--

Signed and Sealed this
Twenty-seventh Day of December, 2022

Katherine Kelly Vidal
*Director of the United States Patent and Trademark Office*

SEQUENCE LISTING

```
<160> NUMBER OF SEQ ID NOS: 163

<210> SEQ ID NO 1
<211> LENGTH: 512
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(20)
<223> OTHER INFORMATION: Any amino acid or absent
<220> FEATURE:
<221> NAME/KEY: MOD_RES
<222> LOCATION: (24)..(25)
<223> OTHER INFORMATION: Any amino acid or absent
<220> FEATURE:
<221> NAME/KEY: MOD_RES
<222> LOCATION: (27)..(36)
<223> OTHER INFORMATION: Any amino acid or absent
<220> FEATURE:
<221> NAME/KEY: MOD_RES
<222> LOCATION: (39)..(42)
```

```
<223> OTHER INFORMATION: Any amino acid or absent
<220> FEATURE:
<221> NAME/KEY: MOD_RES
<222> LOCATION: (44)..(44)
<223> OTHER INFORMATION: Any amino acid or absent
<220> FEATURE:
<221> NAME/KEY: MOD_RES
<222> LOCATION: (48)..(51)
<223> OTHER INFORMATION: Any amino acid or absent
<220> FEATURE:
<221> NAME/KEY: MOD_RES
<222> LOCATION: (57)..(57)
<223> OTHER INFORMATION: Any amino acid or absent
<220> FEATURE:
<221> NAME/KEY: MOD_RES
<222> LOCATION: (59)..(59)
<223> OTHER INFORMATION: Any amino acid or absent
<220> FEATURE:
<221> NAME/KEY: MOD_RES
<222> LOCATION: (61)..(61)
<223> OTHER INFORMATION: Any amino acid or absent
<220> FEATURE:
<221> NAME/KEY: MOD_RES
<222> LOCATION: (64)..(66)
<223> OTHER INFORMATION: Any amino acid or absent
<220> FEATURE:
<221> NAME/KEY: MOD_RES
<222> LOCATION: (68)..(69)
<223> OTHER INFORMATION: Any amino acid or absent
<220> FEATURE:
<221> NAME/KEY: MOD_RES
<222> LOCATION: (71)..(72)
<223> OTHER INFORMATION: Any amino acid or absent
<220> FEATURE:
<221> NAME/KEY: MOD_RES
<222> LOCATION: (78)..(84)
<223> OTHER INFORMATION: Any amino acid or absent
<220> FEATURE:
<221> NAME/KEY: MOD_RES
<222> LOCATION: (87)..(88)
<223> OTHER INFORMATION: Any amino acid or absent
<220> FEATURE:
<221> NAME/KEY: MOD_RES
<222> LOCATION: (96)..(99)
<223> OTHER INFORMATION: Any amino acid or absent
<220> FEATURE:
<221> NAME/KEY: MOD_RES
<222> LOCATION: (107)..(109)
<223> OTHER INFORMATION: Any amino acid or absent
<220> FEATURE:
<221> NAME/KEY: MOD_RES
<222> LOCATION: (111)..(127)
<223> OTHER INFORMATION: Any amino acid or absent
<220> FEATURE:
<221> NAME/KEY: MOD_RES
<222> LOCATION: (129)..(129)
<223> OTHER INFORMATION: Any amino acid or absent
<220> FEATURE:
<221> NAME/KEY: MOD_RES
<222> LOCATION: (132)..(132)
<223> OTHER INFORMATION: Any amino acid or absent
<220> FEATURE:
<221> NAME/KEY: MOD_RES
<222> LOCATION: (134)..(135)
<223> OTHER INFORMATION: Any amino acid or absent
<220> FEATURE:
<221> NAME/KEY: MOD_RES
<222> LOCATION: (139)..(139)
<223> OTHER INFORMATION: Any amino acid or absent
<220> FEATURE:
<221> NAME/KEY: MOD_RES
<222> LOCATION: (142)..(142)
<223> OTHER INFORMATION: Any amino acid or absent
<220> FEATURE:
<221> NAME/KEY: MOD_RES
<222> LOCATION: (144)..(144)
<223> OTHER INFORMATION: Any amino acid or absent
<220> FEATURE:
<221> NAME/KEY: MOD_RES
```

```
<222> LOCATION: (147)..(152)
<223> OTHER INFORMATION: Any amino acid or absent
<220> FEATURE:
<221> NAME/KEY: MOD_RES
<222> LOCATION: (157)..(158)
<223> OTHER INFORMATION: Any amino acid or absent
<220> FEATURE:
<221> NAME/KEY: MOD_RES
<222> LOCATION: (163)..(163)
<223> OTHER INFORMATION: Any amino acid or absent
<220> FEATURE:
<221> NAME/KEY: MOD_RES
<222> LOCATION: (166)..(172)
<223> OTHER INFORMATION: Any amino acid or absent
<220> FEATURE:
<221> NAME/KEY: MOD_RES
<222> LOCATION: (178)..(178)
<223> OTHER INFORMATION: Any amino acid or absent
<220> FEATURE:
<221> NAME/KEY: MOD_RES
<222> LOCATION: (182)..(194)
<223> OTHER INFORMATION: Any amino acid or absent
<220> FEATURE:
<221> NAME/KEY: MOD_RES
<222> LOCATION: (201)..(208)
<223> OTHER INFORMATION: Any amino acid or absent
<220> FEATURE:
<221> NAME/KEY: MOD_RES
<222> LOCATION: (218)..(224)
<223> OTHER INFORMATION: Any amino acid or absent
<220> FEATURE:
<221> NAME/KEY: MOD_RES
<222> LOCATION: (226)..(226)
<223> OTHER INFORMATION: Any amino acid or absent
<220> FEATURE:
<221> NAME/KEY: MOD_RES
<222> LOCATION: (229)..(244)
<223> OTHER INFORMATION: Any amino acid or absent
<220> FEATURE:
<221> NAME/KEY: MOD_RES
<222> LOCATION: (246)..(247)
<223> OTHER INFORMATION: Any amino acid or absent
<220> FEATURE:
<221> NAME/KEY: MOD_RES
<222> LOCATION: (249)..(249)
<223> OTHER INFORMATION: Any amino acid or absent
<220> FEATURE:
<221> NAME/KEY: MOD_RES
<222> LOCATION: (252)..(256)
<223> OTHER INFORMATION: Any amino acid or absent
<220> FEATURE:
<221> NAME/KEY: MOD_RES
<222> LOCATION: (260)..(268)
<223> OTHER INFORMATION: Any amino acid or absent
<220> FEATURE:
<221> NAME/KEY: MOD_RES
<222> LOCATION: (272)..(276)
<223> OTHER INFORMATION: Any amino acid or absent
<220> FEATURE:
<221> NAME/KEY: MOD_RES
<222> LOCATION: (278)..(278)
<223> OTHER INFORMATION: Any amino acid or absent
<220> FEATURE:
<221> NAME/KEY: MOD_RES
<222> LOCATION: (280)..(289)
<223> OTHER INFORMATION: Any amino acid or absent
<220> FEATURE:
<221> NAME/KEY: MOD_RES
<222> LOCATION: (291)..(299)
<223> OTHER INFORMATION: Any amino acid or absent
<220> FEATURE:
<221> NAME/KEY: MOD_RES
<222> LOCATION: (310)..(313)
<223> OTHER INFORMATION: Any amino acid or absent
<220> FEATURE:
<221> NAME/KEY: MOD_RES
<222> LOCATION: (316)..(318)
<223> OTHER INFORMATION: Any amino acid or absent
<220> FEATURE:
```

```
<221> NAME/KEY: MOD_RES
<222> LOCATION: (324)..(347)
<223> OTHER INFORMATION: Any amino acid or absent
<220> FEATURE:
<221> NAME/KEY: MOD_RES
<222> LOCATION: (349)..(353)
<223> OTHER INFORMATION: Any amino acid or absent
<220> FEATURE:
<221> NAME/KEY: MOD_RES
<222> LOCATION: (357)..(376)
<223> OTHER INFORMATION: Any amino acid or absent
<220> FEATURE:
<221> NAME/KEY: MOD_RES
<222> LOCATION: (379)..(379)
<223> OTHER INFORMATION: Any amino acid or absent
<220> FEATURE:
<221> NAME/KEY: MOD_RES
<222> LOCATION: (384)..(386)
<223> OTHER INFORMATION: Any amino acid or absent
<220> FEATURE:
<221> NAME/KEY: MOD_RES
<222> LOCATION: (388)..(391)
<223> OTHER INFORMATION: Any amino acid or absent
<220> FEATURE:
<221> NAME/KEY: MOD_RES
<222> LOCATION: (393)..(393)
<223> OTHER INFORMATION: Any amino acid or absent
<220> FEATURE:
<221> NAME/KEY: MOD_RES
<222> LOCATION: (399)..(399)
<223> OTHER INFORMATION: Any amino acid or absent
<220> FEATURE:
<221> NAME/KEY: MOD_RES
<222> LOCATION: (402)..(402)
<223> OTHER INFORMATION: Any amino acid or absent
<220> FEATURE:
<221> NAME/KEY: MOD_RES
<222> LOCATION: (409)..(409)
<223> OTHER INFORMATION: Any amino acid or absent
<220> FEATURE:
<221> NAME/KEY: MOD_RES
<222> LOCATION: (416)..(416)
<223> OTHER INFORMATION: Any amino acid or absent
<220> FEATURE:
<221> NAME/KEY: MOD_RES
<222> LOCATION: (423)..(469)
<223> OTHER INFORMATION: Any amino acid or absent
<220> FEATURE:
<221> NAME/KEY: MOD_RES
<222> LOCATION: (471)..(507)
<223> OTHER INFORMATION: Any amino acid or absent
<220> FEATURE:
<221> NAME/KEY: MOD_RES
<222> LOCATION: (509)..(511)
<223> OTHER INFORMATION: Any amino acid or absent

<400> SEQUENCE: 1

Xaa Xaa Xaa Xaa Xaa Xaa Xaa Xaa Xaa Xaa Xaa Xaa Xaa Xaa Xaa
1               5                   10                  15

Xaa Xaa Xaa Xaa Gly Ile Thr Xaa Xaa Asn Xaa Xaa Xaa Xaa Xaa
            20                  25                  30

Xaa Xaa Xaa Xaa Gly Glu Xaa Xaa Xaa Xaa Gly Xaa Ile Pro Leu Xaa
        35                  40                  45

Xaa Xaa Xaa Thr Lys Ser Tyr Phe Xaa Asn Xaa Lys Xaa Thr Glu Xaa
    50                  55                  60

Xaa Xaa Lys Xaa Xaa Pro Xaa Xaa Leu Asn Cys Thr Asp Xaa Xaa
65                  70                  75                  80

Xaa Xaa Xaa Xaa Pro Lys Xaa Xaa Gly Lys Ile Pro Ser Ala Lys Xaa
            85                  90                  95

Xaa Xaa Xaa His Glu Val Arg Pro Val Thr Xaa Xaa Xaa Phe Xaa Xaa
        100                 105                 110
```

```
Xaa Xaa Xaa Xaa Xaa Xaa Xaa Xaa Xaa Xaa Xaa Gly
        115                 120                 125

Xaa Glu His Xaa Arg Xaa Thr Gln Asn Xaa Ile Asp Xaa Glu Xaa
    130             135                 140

Ala Pro Xaa Xaa Xaa Xaa Xaa Gly Thr Ser Gly Xaa Xaa Pro Asn
145             150                 155                 160

Ala Thr Xaa Lys Ser Xaa Xaa Xaa Xaa Xaa Xaa Trp Ala Val Pro
            165                 170                 175

Lys Xaa Asp Asn Xaa Xaa Xaa Xaa Xaa Xaa Xaa Xaa Xaa Xaa Xaa
        180                 185                 190

Xaa Xaa Ile Cys Thr Glu Gly Glu Xaa Xaa Xaa Xaa Xaa Xaa Xaa
        195                 200                 205

His Ser Asp Asn Lys Thr Gln Met Lys Xaa Xaa Xaa Xaa Xaa Xaa
    210                 215                 220

Pro Xaa Lys Phe Xaa Xaa Xaa Xaa Xaa Xaa Xaa Xaa Xaa Xaa Xaa
225             230                 235                 240

Xaa Xaa Xaa Xaa Gly Xaa Xaa Asp Xaa Thr Glu Xaa Xaa Xaa Xaa
            245                 250                 255

Gln Ser Gly Xaa Xaa Xaa Xaa Xaa Xaa Xaa Xaa Lys Pro Gly Xaa
            260                 265                 270

Xaa Xaa Xaa Xaa Val Xaa Gln Xaa Xaa Xaa Xaa Xaa Xaa Xaa Xaa
        275                 280                 285

Xaa Cys Xaa Xaa Xaa Xaa Xaa Xaa Xaa Xaa Gly Ser Leu Pro Leu
    290                 295                 300

Ile Gly Glu Ala Asp Xaa Xaa Xaa Xaa Lys Tyr Xaa Xaa Xaa Asn Lys
305                 310                 315                 320

Ser Lys Pro Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Asn Xaa Xaa Xaa Xaa
            340                 345                 350

Xaa Pro Pro Ala Xaa Xaa Xaa Xaa Xaa Xaa Xaa Xaa Xaa Xaa Xaa
        355                 360                 365

Xaa Xaa Xaa Xaa Xaa Xaa Xaa Glu Gly Xaa Val Ala Gly Trp Xaa
370                 375                 380

Xaa Xaa Thr Xaa Xaa Xaa Xaa His Xaa Val Ala Val Ala Ala Xaa Leu
        385                 390                 395                 400

Lys Xaa Thr Gln Glu Ala Ile Asn Xaa Ile Thr Lys Asn Leu Asn Xaa
            405                 410                 415

Leu Ser Glu Leu Glu Ile Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa
            435                 440                 445

Xaa Xaa Xaa Xaa Xaa Xaa Xaa Xaa Xaa Xaa Xaa Xaa Xaa Xaa Xaa
        450                 455                 460

Xaa Xaa Xaa Xaa Ile Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Gln Xaa Xaa Xaa Asp
        500                 505                 510

<210> SEQ ID NO 2
<211> LENGTH: 512
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(20)
<223> OTHER INFORMATION: Any amino acid or absent
<220> FEATURE:
<221> NAME/KEY: MOD_RES
<222> LOCATION: (24)..(25)
<223> OTHER INFORMATION: Any amino acid or absent
<220> FEATURE:
<221> NAME/KEY: MOD_RES
<222> LOCATION: (27)..(36)
<223> OTHER INFORMATION: Any amino acid or absent
<220> FEATURE:
<221> NAME/KEY: MOD_RES
<222> LOCATION: (39)..(42)
<223> OTHER INFORMATION: Any amino acid or absent
<220> FEATURE:
<221> NAME/KEY: MOD_RES
<222> LOCATION: (44)..(44)
<223> OTHER INFORMATION: Any amino acid or absent
<220> FEATURE:
<221> NAME/KEY: MOD_RES
<222> LOCATION: (48)..(51)
<223> OTHER INFORMATION: Any amino acid or absent
<220> FEATURE:
<221> NAME/KEY: MOD_RES
<222> LOCATION: (57)..(57)
<223> OTHER INFORMATION: Any amino acid or absent
<220> FEATURE:
<221> NAME/KEY: MOD_RES
<222> LOCATION: (59)..(59)
<223> OTHER INFORMATION: Any amino acid or absent
<220> FEATURE:
<221> NAME/KEY: MOD_RES
<222> LOCATION: (61)..(61)
<223> OTHER INFORMATION: Any amino acid or absent
<220> FEATURE:
<221> NAME/KEY: MOD_RES
<222> LOCATION: (64)..(66)
<223> OTHER INFORMATION: Any amino acid or absent
<220> FEATURE:
<221> NAME/KEY: MOD_RES
<222> LOCATION: (68)..(69)
<223> OTHER INFORMATION: Any amino acid or absent
<220> FEATURE:
<221> NAME/KEY: MOD_RES
<222> LOCATION: (71)..(72)
<223> OTHER INFORMATION: Any amino acid or absent
<220> FEATURE:
<221> NAME/KEY: MOD_RES
<222> LOCATION: (78)..(84)
<223> OTHER INFORMATION: Any amino acid or absent
<220> FEATURE:
<221> NAME/KEY: MOD_RES
<222> LOCATION: (87)..(88)
<223> OTHER INFORMATION: Any amino acid or absent
<220> FEATURE:
<221> NAME/KEY: MOD_RES
<222> LOCATION: (96)..(99)
<223> OTHER INFORMATION: Any amino acid or absent
<220> FEATURE:
<221> NAME/KEY: MOD_RES
<222> LOCATION: (107)..(109)
<223> OTHER INFORMATION: Any amino acid or absent
<220> FEATURE:
<221> NAME/KEY: MOD_RES
<222> LOCATION: (111)..(127)
<223> OTHER INFORMATION: Any amino acid or absent
<220> FEATURE:
<221> NAME/KEY: MOD_RES
<222> LOCATION: (129)..(129)
<223> OTHER INFORMATION: Any amino acid or absent
<220> FEATURE:
<221> NAME/KEY: MOD_RES
```

```
<222> LOCATION: (132)..(132)
<223> OTHER INFORMATION: Any amino acid or absent
<220> FEATURE:
<221> NAME/KEY: MOD_RES
<222> LOCATION: (134)..(135)
<223> OTHER INFORMATION: Any amino acid or absent
<220> FEATURE:
<221> NAME/KEY: MOD_RES
<222> LOCATION: (139)..(139)
<223> OTHER INFORMATION: Any amino acid or absent
<220> FEATURE:
<221> NAME/KEY: MOD_RES
<222> LOCATION: (142)..(142)
<223> OTHER INFORMATION: Any amino acid or absent
<220> FEATURE:
<221> NAME/KEY: MOD_RES
<222> LOCATION: (144)..(144)
<223> OTHER INFORMATION: Any amino acid or absent
<220> FEATURE:
<221> NAME/KEY: MOD_RES
<222> LOCATION: (147)..(152)
<223> OTHER INFORMATION: Any amino acid or absent
<220> FEATURE:
<221> NAME/KEY: MOD_RES
<222> LOCATION: (157)..(158)
<223> OTHER INFORMATION: Any amino acid or absent
<220> FEATURE:
<221> NAME/KEY: MOD_RES
<222> LOCATION: (163)..(163)
<223> OTHER INFORMATION: Any amino acid or absent
<220> FEATURE:
<221> NAME/KEY: MOD_RES
<222> LOCATION: (166)..(172)
<223> OTHER INFORMATION: Any amino acid or absent
<220> FEATURE:
<221> NAME/KEY: MOD_RES
<222> LOCATION: (178)..(178)
<223> OTHER INFORMATION: Any amino acid or absent
<220> FEATURE:
<221> NAME/KEY: MOD_RES
<222> LOCATION: (182)..(194)
<223> OTHER INFORMATION: Any amino acid or absent
<220> FEATURE:
<221> NAME/KEY: MOD_RES
<222> LOCATION: (201)..(208)
<223> OTHER INFORMATION: Any amino acid or absent
<220> FEATURE:
<221> NAME/KEY: MOD_RES
<222> LOCATION: (218)..(224)
<223> OTHER INFORMATION: Any amino acid or absent
<220> FEATURE:
<221> NAME/KEY: MOD_RES
<222> LOCATION: (226)..(226)
<223> OTHER INFORMATION: Any amino acid or absent
<220> FEATURE:
<221> NAME/KEY: MOD_RES
<222> LOCATION: (229)..(244)
<223> OTHER INFORMATION: Any amino acid or absent
<220> FEATURE:
<221> NAME/KEY: MOD_RES
<222> LOCATION: (246)..(247)
<223> OTHER INFORMATION: Any amino acid or absent
<220> FEATURE:
<221> NAME/KEY: MOD_RES
<222> LOCATION: (249)..(249)
<223> OTHER INFORMATION: Any amino acid or absent
<220> FEATURE:
<221> NAME/KEY: MOD_RES
<222> LOCATION: (252)..(256)
<223> OTHER INFORMATION: Any amino acid or absent
<220> FEATURE:
<221> NAME/KEY: MOD_RES
<222> LOCATION: (260)..(268)
<223> OTHER INFORMATION: Any amino acid or absent
<220> FEATURE:
<221> NAME/KEY: MOD_RES
<222> LOCATION: (272)..(276)
<223> OTHER INFORMATION: Any amino acid or absent
<220> FEATURE:
```

```
<221> NAME/KEY: MOD_RES
<222> LOCATION: (278)..(278)
<223> OTHER INFORMATION: Any amino acid or absent
<220> FEATURE:
<221> NAME/KEY: MOD_RES
<222> LOCATION: (280)..(289)
<223> OTHER INFORMATION: Any amino acid or absent
<220> FEATURE:
<221> NAME/KEY: MOD_RES
<222> LOCATION: (291)..(299)
<223> OTHER INFORMATION: Any amino acid or absent
<220> FEATURE:
<221> NAME/KEY: MOD_RES
<222> LOCATION: (310)..(313)
<223> OTHER INFORMATION: Any amino acid or absent
<220> FEATURE:
<221> NAME/KEY: MOD_RES
<222> LOCATION: (316)..(318)
<223> OTHER INFORMATION: Any amino acid or absent
<220> FEATURE:
<221> NAME/KEY: MOD_RES
<222> LOCATION: (324)..(347)
<223> OTHER INFORMATION: Any amino acid or absent
<220> FEATURE:
<221> NAME/KEY: MOD_RES
<222> LOCATION: (349)..(353)
<223> OTHER INFORMATION: Any amino acid or absent
<220> FEATURE:
<221> NAME/KEY: MOD_RES
<222> LOCATION: (357)..(376)
<223> OTHER INFORMATION: Any amino acid or absent
<220> FEATURE:
<221> NAME/KEY: MOD_RES
<222> LOCATION: (379)..(379)
<223> OTHER INFORMATION: Any amino acid or absent
<220> FEATURE:
<221> NAME/KEY: MOD_RES
<222> LOCATION: (384)..(386)
<223> OTHER INFORMATION: Any amino acid or absent
<220> FEATURE:
<221> NAME/KEY: MOD_RES
<222> LOCATION: (388)..(391)
<223> OTHER INFORMATION: Any amino acid or absent
<220> FEATURE:
<221> NAME/KEY: MOD_RES
<222> LOCATION: (393)..(393)
<223> OTHER INFORMATION: Any amino acid or absent
<220> FEATURE:
<221> NAME/KEY: MOD_RES
<222> LOCATION: (399)..(399)
<223> OTHER INFORMATION: Any amino acid or absent
<220> FEATURE:
<221> NAME/KEY: MOD_RES
<222> LOCATION: (402)..(402)
<223> OTHER INFORMATION: Any amino acid or absent
<220> FEATURE:
<221> NAME/KEY: MOD_RES
<222> LOCATION: (409)..(409)
<223> OTHER INFORMATION: Any amino acid or absent
<220> FEATURE:
<221> NAME/KEY: MOD_RES
<222> LOCATION: (416)..(416)
<223> OTHER INFORMATION: Any amino acid or absent
<220> FEATURE:
<221> NAME/KEY: MOD_RES
<222> LOCATION: (423)..(469)
<223> OTHER INFORMATION: Any amino acid or absent
<220> FEATURE:
<221> NAME/KEY: MOD_RES
<222> LOCATION: (471)..(507)
<223> OTHER INFORMATION: Any amino acid or absent
<220> FEATURE:
<221> NAME/KEY: MOD_RES
<222> LOCATION: (509)..(511)
<223> OTHER INFORMATION: Any amino acid or absent

<400> SEQUENCE: 2

Xaa Xaa Xaa Xaa Xaa Xaa Xaa Xaa Xaa Xaa Xaa Xaa Xaa Xaa Xaa Xaa
```

-continued

```
1               5                   10                  15
Xaa Xaa Xaa Xaa Gly Ile Thr Xaa Xaa Asn Xaa Xaa Xaa Xaa Xaa
                20                  25                  30

Xaa Xaa Xaa Xaa Gly Glu Xaa Xaa Xaa Gly Xaa Ile Ser Leu Xaa
                35                  40                  45

Xaa Xaa Xaa Thr Lys Ser His Phe Xaa Asn Xaa Lys Xaa Thr Lys Xaa
        50                  55                  60

Xaa Xaa Lys Xaa Xaa Pro Xaa Xaa Pro Asn Cys Thr Asp Xaa Xaa
65                  70                  75                  80

Xaa Xaa Xaa Xaa Pro Met Xaa Xaa Gly Thr Ile Pro Ser Ala Lys Xaa
                    85                  90                  95

Xaa Xaa Xaa His Glu Val Arg Pro Val Thr Xaa Xaa Xaa Phe Xaa Xaa
                100                 105                 110

Xaa Xaa Xaa Xaa Xaa Xaa Xaa Xaa Xaa Xaa Xaa Xaa Xaa Gly
            115                 120                 125

Xaa Glu His Xaa Arg Xaa Xaa Thr His Asn Xaa Ile Asn Xaa Glu Xaa
    130                 135                 140

Ala Pro Xaa Xaa Xaa Xaa Xaa Gly Thr Ser Gly Xaa Xaa Pro Asn
145                 150                 155                 160

Ala Thr Xaa Lys Ile Xaa Xaa Xaa Xaa Xaa Xaa Trp Ala Val Pro
            165                 170                 175

Lys Xaa Asp Asn Xaa Xaa Xaa Xaa Xaa Xaa Xaa Xaa Xaa Xaa
        180                 185                 190

Xaa Xaa Ile Cys Ala Glu Gly Glu Xaa Xaa Xaa Xaa Xaa Xaa Xaa
            195                 200                 205

His Ser Asp Asp Lys Thr Gln Met Lys Xaa Xaa Xaa Xaa Xaa Xaa
    210                 215                 220

Pro Xaa Lys Phe Xaa Xaa Xaa Xaa Xaa Xaa Xaa Xaa Xaa Xaa Xaa
225                 230                 235                 240

Xaa Xaa Xaa Xaa Asp Xaa Xaa Asn Xaa Thr Glu Xaa Xaa Xaa Xaa
            245                 250                 255

Gln Ser Gly Xaa Xaa Xaa Xaa Xaa Xaa Xaa Xaa Lys Pro Gly Xaa
            260                 265                 270

Xaa Xaa Xaa Xaa Thr Xaa Gln Xaa Xaa Xaa Xaa Xaa Xaa Xaa Xaa
        275                 280                 285

Xaa Cys Xaa Xaa Xaa Xaa Xaa Xaa Xaa Xaa Gly Ser Leu Pro Leu
    290                 295                 300

Ile Gly Glu Ala Asp Xaa Xaa Xaa Xaa Lys Tyr Xaa Xaa Xaa Asn Lys
305                 310                 315                 320

Ser Lys Pro Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Asn Xaa Xaa Xaa
            340                 345                 350

Xaa Pro Pro Thr Xaa Xaa Xaa Xaa Xaa Xaa Xaa Xaa Xaa Xaa
        355                 360                 365

Xaa Xaa Xaa Xaa Xaa Xaa Xaa Glu Gly Xaa Ile Ala Gly Trp Xaa
            370                 375                 380

Xaa Xaa Thr Xaa Xaa Xaa Xaa His Xaa Val Ala Val Ala Ala Xaa Leu
385                 390                 395                 400

Lys Xaa Thr Gln Glu Ala Ile Asn Xaa Ile Thr Lys Asn Leu Asn Xaa
            405                 410                 415

Leu Ser Glu Leu Glu Val Xaa Xaa Xaa Xaa Xaa Xaa Xaa Xaa Xaa
            420                 425                 430
```

```
Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa
    450                 455                 460

Xaa Xaa Xaa Xaa Xaa Ile Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Gln Xaa Xaa Xaa Asn
        500                 505                 510

<210> SEQ ID NO 3
<211> LENGTH: 512
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(20)
<223> OTHER INFORMATION: Any amino acid or absent
<220> FEATURE:
<221> NAME/KEY: MOD_RES
<222> LOCATION: (24)..(25)
<223> OTHER INFORMATION: Any amino acid or absent
<220> FEATURE:
<221> NAME/KEY: MOD_RES
<222> LOCATION: (27)..(36)
<223> OTHER INFORMATION: Any amino acid or absent
<220> FEATURE:
<221> NAME/KEY: MOD_RES
<222> LOCATION: (39)..(42)
<223> OTHER INFORMATION: Any amino acid or absent
<220> FEATURE:
<221> NAME/KEY: MOD_RES
<222> LOCATION: (44)..(44)
<223> OTHER INFORMATION: Any amino acid or absent
<220> FEATURE:
<221> NAME/KEY: MOD_RES
<222> LOCATION: (48)..(51)
<223> OTHER INFORMATION: Any amino acid or absent
<220> FEATURE:
<221> NAME/KEY: MOD_RES
<222> LOCATION: (57)..(57)
<223> OTHER INFORMATION: Any amino acid or absent
<220> FEATURE:
<221> NAME/KEY: MOD_RES
<222> LOCATION: (59)..(59)
<223> OTHER INFORMATION: Any amino acid or absent
<220> FEATURE:
<221> NAME/KEY: MOD_RES
<222> LOCATION: (61)..(61)
<223> OTHER INFORMATION: Any amino acid or absent
<220> FEATURE:
<221> NAME/KEY: MOD_RES
<222> LOCATION: (64)..(66)
<223> OTHER INFORMATION: Any amino acid or absent
<220> FEATURE:
<221> NAME/KEY: MOD_RES
<222> LOCATION: (68)..(69)
<223> OTHER INFORMATION: Any amino acid or absent
<220> FEATURE:
<221> NAME/KEY: MOD_RES
<222> LOCATION: (71)..(72)
<223> OTHER INFORMATION: Any amino acid or absent
<220> FEATURE:
<221> NAME/KEY: MOD_RES
<222> LOCATION: (78)..(84)
<223> OTHER INFORMATION: Any amino acid or absent
<220> FEATURE:
<221> NAME/KEY: MOD_RES
```

```
<222> LOCATION: (87)..(88)
<223> OTHER INFORMATION: Any amino acid or absent
<220> FEATURE:
<221> NAME/KEY: MOD_RES
<222> LOCATION: (96)..(99)
<223> OTHER INFORMATION: Any amino acid or absent
<220> FEATURE:
<221> NAME/KEY: MOD_RES
<222> LOCATION: (107)..(109)
<223> OTHER INFORMATION: Any amino acid or absent
<220> FEATURE:
<221> NAME/KEY: MOD_RES
<222> LOCATION: (111)..(127)
<223> OTHER INFORMATION: Any amino acid or absent
<220> FEATURE:
<221> NAME/KEY: MOD_RES
<222> LOCATION: (129)..(129)
<223> OTHER INFORMATION: Any amino acid or absent
<220> FEATURE:
<221> NAME/KEY: MOD_RES
<222> LOCATION: (132)..(132)
<223> OTHER INFORMATION: Any amino acid or absent
<220> FEATURE:
<221> NAME/KEY: MOD_RES
<222> LOCATION: (134)..(135)
<223> OTHER INFORMATION: Any amino acid or absent
<220> FEATURE:
<221> NAME/KEY: MOD_RES
<222> LOCATION: (139)..(139)
<223> OTHER INFORMATION: Any amino acid or absent
<220> FEATURE:
<221> NAME/KEY: MOD_RES
<222> LOCATION: (142)..(142)
<223> OTHER INFORMATION: Any amino acid or absent
<220> FEATURE:
<221> NAME/KEY: MOD_RES
<222> LOCATION: (144)..(144)
<223> OTHER INFORMATION: Any amino acid or absent
<220> FEATURE:
<221> NAME/KEY: MOD_RES
<222> LOCATION: (147)..(152)
<223> OTHER INFORMATION: Any amino acid or absent
<220> FEATURE:
<221> NAME/KEY: MOD_RES
<222> LOCATION: (157)..(158)
<223> OTHER INFORMATION: Any amino acid or absent
<220> FEATURE:
<221> NAME/KEY: MOD_RES
<222> LOCATION: (163)..(163)
<223> OTHER INFORMATION: Any amino acid or absent
<220> FEATURE:
<221> NAME/KEY: MOD_RES
<222> LOCATION: (166)..(172)
<223> OTHER INFORMATION: Any amino acid or absent
<220> FEATURE:
<221> NAME/KEY: MOD_RES
<222> LOCATION: (178)..(178)
<223> OTHER INFORMATION: Any amino acid or absent
<220> FEATURE:
<221> NAME/KEY: MOD_RES
<222> LOCATION: (182)..(194)
<223> OTHER INFORMATION: Any amino acid or absent
<220> FEATURE:
<221> NAME/KEY: MOD_RES
<222> LOCATION: (201)..(208)
<223> OTHER INFORMATION: Any amino acid or absent
<220> FEATURE:
<221> NAME/KEY: MOD_RES
<222> LOCATION: (218)..(224)
<223> OTHER INFORMATION: Any amino acid or absent
<220> FEATURE:
<221> NAME/KEY: MOD_RES
<222> LOCATION: (226)..(226)
<223> OTHER INFORMATION: Any amino acid or absent
<220> FEATURE:
<221> NAME/KEY: MOD_RES
<222> LOCATION: (229)..(244)
<223> OTHER INFORMATION: Any amino acid or absent
<220> FEATURE:
```

```
<221> NAME/KEY: MOD_RES
<222> LOCATION: (246)..(247)
<223> OTHER INFORMATION: Any amino acid or absent
<220> FEATURE:
<221> NAME/KEY: MOD_RES
<222> LOCATION: (249)..(249)
<223> OTHER INFORMATION: Any amino acid or absent
<220> FEATURE:
<221> NAME/KEY: MOD_RES
<222> LOCATION: (252)..(256)
<223> OTHER INFORMATION: Any amino acid or absent
<220> FEATURE:
<221> NAME/KEY: MOD_RES
<222> LOCATION: (260)..(268)
<223> OTHER INFORMATION: Any amino acid or absent
<220> FEATURE:
<221> NAME/KEY: MOD_RES
<222> LOCATION: (272)..(276)
<223> OTHER INFORMATION: Any amino acid or absent
<220> FEATURE:
<221> NAME/KEY: MOD_RES
<222> LOCATION: (278)..(278)
<223> OTHER INFORMATION: Any amino acid or absent
<220> FEATURE:
<221> NAME/KEY: MOD_RES
<222> LOCATION: (280)..(289)
<223> OTHER INFORMATION: Any amino acid or absent
<220> FEATURE:
<221> NAME/KEY: MOD_RES
<222> LOCATION: (291)..(299)
<223> OTHER INFORMATION: Any amino acid or absent
<220> FEATURE:
<221> NAME/KEY: MOD_RES
<222> LOCATION: (310)..(313)
<223> OTHER INFORMATION: Any amino acid or absent
<220> FEATURE:
<221> NAME/KEY: MOD_RES
<222> LOCATION: (316)..(318)
<223> OTHER INFORMATION: Any amino acid or absent
<220> FEATURE:
<221> NAME/KEY: MOD_RES
<222> LOCATION: (324)..(347)
<223> OTHER INFORMATION: Any amino acid or absent
<220> FEATURE:
<221> NAME/KEY: MOD_RES
<222> LOCATION: (349)..(353)
<223> OTHER INFORMATION: Any amino acid or absent
<220> FEATURE:
<221> NAME/KEY: MOD_RES
<222> LOCATION: (357)..(376)
<223> OTHER INFORMATION: Any amino acid or absent
<220> FEATURE:
<221> NAME/KEY: MOD_RES
<222> LOCATION: (379)..(379)
<223> OTHER INFORMATION: Any amino acid or absent
<220> FEATURE:
<221> NAME/KEY: MOD_RES
<222> LOCATION: (384)..(386)
<223> OTHER INFORMATION: Any amino acid or absent
<220> FEATURE:
<221> NAME/KEY: MOD_RES
<222> LOCATION: (388)..(391)
<223> OTHER INFORMATION: Any amino acid or absent
<220> FEATURE:
<221> NAME/KEY: MOD_RES
<222> LOCATION: (393)..(393)
<223> OTHER INFORMATION: Any amino acid or absent
<220> FEATURE:
<221> NAME/KEY: MOD_RES
<222> LOCATION: (399)..(399)
<223> OTHER INFORMATION: Any amino acid or absent
<220> FEATURE:
<221> NAME/KEY: MOD_RES
<222> LOCATION: (402)..(402)
<223> OTHER INFORMATION: Any amino acid or absent
<220> FEATURE:
<221> NAME/KEY: MOD_RES
<222> LOCATION: (409)..(409)
<223> OTHER INFORMATION: Any amino acid or absent
```

```
<220> FEATURE:
<221> NAME/KEY: MOD_RES
<222> LOCATION: (416)..(416)
<223> OTHER INFORMATION: Any amino acid or absent
<220> FEATURE:
<221> NAME/KEY: MOD_RES
<222> LOCATION: (423)..(469)
<223> OTHER INFORMATION: Any amino acid or absent
<220> FEATURE:
<221> NAME/KEY: MOD_RES
<222> LOCATION: (471)..(507)
<223> OTHER INFORMATION: Any amino acid or absent
<220> FEATURE:
<221> NAME/KEY: MOD_RES
<222> LOCATION: (509)..(511)
<223> OTHER INFORMATION: Any amino acid or absent

<400> SEQUENCE: 3

Xaa Xaa Xaa Xaa Xaa Xaa Xaa Xaa Xaa Xaa Xaa Xaa Xaa Xaa Xaa
 1               5                   10                  15

Xaa Xaa Xaa Xaa Gly Ile Thr Xaa Xaa Asn Xaa Xaa Xaa Xaa Xaa
                20                  25                  30

Xaa Xaa Xaa Xaa Gly Glu Xaa Xaa Xaa Gly Xaa Ile Pro Leu Xaa
                35                  40                  45

Xaa Xaa Xaa Thr Lys Ser His Phe Xaa Asn Xaa Lys Xaa Thr Glu Xaa
 50                  55                  60

Xaa Xaa Lys Xaa Xaa Pro Xaa Xaa Leu Asn Cys Thr Asp Xaa Xaa
 65                  70                  75                  80

Xaa Xaa Xaa Xaa Pro Lys Xaa Xaa Gly Lys Ile Pro Ser Ala Arg Xaa
                85                  90                  95

Xaa Xaa Xaa His Glu Val Arg Pro Val Thr Xaa Xaa Phe Xaa Xaa
                100                 105                 110

Xaa Xaa Xaa Xaa Xaa Xaa Xaa Xaa Xaa Xaa Xaa Xaa Xaa Xaa Gly
                115                 120                 125

Xaa Glu His Xaa Arg Xaa Xaa Thr Gln Asn Xaa Ile Asn Xaa Glu Xaa
 130                 135                 140

Ala Pro Xaa Xaa Xaa Xaa Xaa Gly Thr Ser Gly Xaa Xaa Pro Asn
145                 150                 155                 160

Ala Thr Xaa Lys Ser Xaa Xaa Xaa Xaa Xaa Xaa Trp Ala Val Pro
                165                 170                 175

Lys Xaa Asp Asn Asn Xaa Xaa Xaa Xaa Xaa Xaa Xaa Xaa Xaa Xaa
                180                 185                 190

Xaa Xaa Ile Cys Thr Glu Gly Glu Xaa Xaa Xaa Xaa Xaa Xaa Xaa
                195                 200                 205

His Ser Asp Asn Lys Thr Gln Met Lys Xaa Xaa Xaa Xaa Xaa Xaa
210                 215                 220

Pro Xaa Lys Phe Xaa Xaa Xaa Xaa Xaa Xaa Xaa Xaa Xaa Xaa Xaa
225                 230                 235                 240

Xaa Xaa Xaa Xaa Gly Xaa Xaa Asn Xaa Thr Glu Xaa Xaa Xaa Xaa
                245                 250                 255

Gln Ser Gly Xaa Xaa Xaa Xaa Xaa Xaa Xaa Xaa Lys Pro Gly Xaa
                260                 265                 270

Xaa Xaa Xaa Xaa Val Xaa Gln Xaa Xaa Xaa Xaa Xaa Xaa Xaa Xaa
                275                 280                 285

Xaa Cys Xaa Xaa Xaa Xaa Xaa Xaa Xaa Xaa Gly Ser Leu Pro Leu
                290                 295                 300

Ile Gly Glu Ala Asp Xaa Xaa Xaa Xaa Lys Tyr Xaa Xaa Xaa Asn Lys
305                 310                 315                 320
```

```
Ser Lys Pro Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Asn Xaa Xaa Xaa
        340                 345                 350

Xaa Pro Pro Ala Xaa Xaa Xaa Xaa Xaa Xaa Xaa Xaa Xaa Xaa
        355                 360                 365

Xaa Xaa Xaa Xaa Xaa Xaa Xaa Xaa Glu Gly Xaa Ile Ala Gly Trp Xaa
    370                 375                 380

Xaa Xaa Thr Xaa Xaa Xaa Xaa Xaa His Xaa Val Ala Val Ala Ala Xaa Leu
385                 390                 395                 400

Lys Xaa Thr Gln Glu Ala Ile Asn Xaa Ile Thr Lys Asn Leu Asn Xaa
            405                 410                 415

Leu Ser Glu Leu Glu Val Xaa Xaa Xaa Xaa Xaa Xaa Xaa Xaa
                420                 425                 430

Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa
    450                 455                 460

Xaa Xaa Xaa Xaa Xaa Ile Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa
        485                 490                 495

Xaa Xaa Xaa Xaa Xaa Xaa Xaa Xaa Xaa Gln Xaa Xaa Xaa Asp
        500                 505                 510

<210> SEQ ID NO 4
<211> LENGTH: 512
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(20)
<223> OTHER INFORMATION: Any amino acid or absent
<220> FEATURE:
<221> NAME/KEY: MOD_RES
<222> LOCATION: (24)..(25)
<223> OTHER INFORMATION: Any amino acid or absent
<220> FEATURE:
<221> NAME/KEY: MOD_RES
<222> LOCATION: (27)..(36)
<223> OTHER INFORMATION: Any amino acid or absent
<220> FEATURE:
<221> NAME/KEY: MOD_RES
<222> LOCATION: (39)..(42)
<223> OTHER INFORMATION: Any amino acid or absent
<220> FEATURE:
<221> NAME/KEY: MOD_RES
<222> LOCATION: (44)..(44)
<223> OTHER INFORMATION: Any amino acid or absent
<220> FEATURE:
<221> NAME/KEY: MOD_RES
<222> LOCATION: (48)..(51)
<223> OTHER INFORMATION: Any amino acid or absent
<220> FEATURE:
<221> NAME/KEY: MOD_RES
<222> LOCATION: (57)..(57)
<223> OTHER INFORMATION: Any amino acid or absent
<220> FEATURE:
<221> NAME/KEY: MOD_RES
<222> LOCATION: (59)..(59)
<223> OTHER INFORMATION: Any amino acid or absent
<220> FEATURE:
<221> NAME/KEY: MOD_RES
```

```
<222> LOCATION: (61)..(61)
<223> OTHER INFORMATION: Any amino acid or absent
<220> FEATURE:
<221> NAME/KEY: MOD_RES
<222> LOCATION: (64)..(66)
<223> OTHER INFORMATION: Any amino acid or absent
<220> FEATURE:
<221> NAME/KEY: MOD_RES
<222> LOCATION: (68)..(69)
<223> OTHER INFORMATION: Any amino acid or absent
<220> FEATURE:
<221> NAME/KEY: MOD_RES
<222> LOCATION: (71)..(72)
<223> OTHER INFORMATION: Any amino acid or absent
<220> FEATURE:
<221> NAME/KEY: MOD_RES
<222> LOCATION: (78)..(84)
<223> OTHER INFORMATION: Any amino acid or absent
<220> FEATURE:
<221> NAME/KEY: MOD_RES
<222> LOCATION: (87)..(88)
<223> OTHER INFORMATION: Any amino acid or absent
<220> FEATURE:
<221> NAME/KEY: MOD_RES
<222> LOCATION: (96)..(99)
<223> OTHER INFORMATION: Any amino acid or absent
<220> FEATURE:
<221> NAME/KEY: MOD_RES
<222> LOCATION: (107)..(109)
<223> OTHER INFORMATION: Any amino acid or absent
<220> FEATURE:
<221> NAME/KEY: MOD_RES
<222> LOCATION: (111)..(127)
<223> OTHER INFORMATION: Any amino acid or absent
<220> FEATURE:
<221> NAME/KEY: MOD_RES
<222> LOCATION: (129)..(129)
<223> OTHER INFORMATION: Any amino acid or absent
<220> FEATURE:
<221> NAME/KEY: MOD_RES
<222> LOCATION: (132)..(132)
<223> OTHER INFORMATION: Any amino acid or absent
<220> FEATURE:
<221> NAME/KEY: MOD_RES
<222> LOCATION: (134)..(135)
<223> OTHER INFORMATION: Any amino acid or absent
<220> FEATURE:
<221> NAME/KEY: MOD_RES
<222> LOCATION: (139)..(139)
<223> OTHER INFORMATION: Any amino acid or absent
<220> FEATURE:
<221> NAME/KEY: MOD_RES
<222> LOCATION: (142)..(142)
<223> OTHER INFORMATION: Any amino acid or absent
<220> FEATURE:
<221> NAME/KEY: MOD_RES
<222> LOCATION: (144)..(144)
<223> OTHER INFORMATION: Any amino acid or absent
<220> FEATURE:
<221> NAME/KEY: MOD_RES
<222> LOCATION: (147)..(152)
<223> OTHER INFORMATION: Any amino acid or absent
<220> FEATURE:
<221> NAME/KEY: MOD_RES
<222> LOCATION: (157)..(158)
<223> OTHER INFORMATION: Any amino acid or absent
<220> FEATURE:
<221> NAME/KEY: MOD_RES
<222> LOCATION: (163)..(163)
<223> OTHER INFORMATION: Any amino acid or absent
<220> FEATURE:
<221> NAME/KEY: MOD_RES
<222> LOCATION: (166)..(172)
<223> OTHER INFORMATION: Any amino acid or absent
<220> FEATURE:
<221> NAME/KEY: MOD_RES
<222> LOCATION: (178)..(178)
<223> OTHER INFORMATION: Any amino acid or absent
<220> FEATURE:
```

```
<221> NAME/KEY: MOD_RES
<222> LOCATION: (182)..(194)
<223> OTHER INFORMATION: Any amino acid or absent
<220> FEATURE:
<221> NAME/KEY: MOD_RES
<222> LOCATION: (201)..(208)
<223> OTHER INFORMATION: Any amino acid or absent
<220> FEATURE:
<221> NAME/KEY: MOD_RES
<222> LOCATION: (218)..(224)
<223> OTHER INFORMATION: Any amino acid or absent
<220> FEATURE:
<221> NAME/KEY: MOD_RES
<222> LOCATION: (226)..(226)
<223> OTHER INFORMATION: Any amino acid or absent
<220> FEATURE:
<221> NAME/KEY: MOD_RES
<222> LOCATION: (229)..(244)
<223> OTHER INFORMATION: Any amino acid or absent
<220> FEATURE:
<221> NAME/KEY: MOD_RES
<222> LOCATION: (246)..(247)
<223> OTHER INFORMATION: Any amino acid or absent
<220> FEATURE:
<221> NAME/KEY: MOD_RES
<222> LOCATION: (249)..(249)
<223> OTHER INFORMATION: Any amino acid or absent
<220> FEATURE:
<221> NAME/KEY: MOD_RES
<222> LOCATION: (252)..(256)
<223> OTHER INFORMATION: Any amino acid or absent
<220> FEATURE:
<221> NAME/KEY: MOD_RES
<222> LOCATION: (260)..(268)
<223> OTHER INFORMATION: Any amino acid or absent
<220> FEATURE:
<221> NAME/KEY: MOD_RES
<222> LOCATION: (272)..(276)
<223> OTHER INFORMATION: Any amino acid or absent
<220> FEATURE:
<221> NAME/KEY: MOD_RES
<222> LOCATION: (278)..(278)
<223> OTHER INFORMATION: Any amino acid or absent
<220> FEATURE:
<221> NAME/KEY: MOD_RES
<222> LOCATION: (280)..(289)
<223> OTHER INFORMATION: Any amino acid or absent
<220> FEATURE:
<221> NAME/KEY: MOD_RES
<222> LOCATION: (291)..(299)
<223> OTHER INFORMATION: Any amino acid or absent
<220> FEATURE:
<221> NAME/KEY: MOD_RES
<222> LOCATION: (308)..(308)
<223> OTHER INFORMATION: Any amino acid or absent
<220> FEATURE:
<221> NAME/KEY: MOD_RES
<222> LOCATION: (310)..(313)
<223> OTHER INFORMATION: Any amino acid or absent
<220> FEATURE:
<221> NAME/KEY: MOD_RES
<222> LOCATION: (316)..(318)
<223> OTHER INFORMATION: Any amino acid or absent
<220> FEATURE:
<221> NAME/KEY: MOD_RES
<222> LOCATION: (324)..(347)
<223> OTHER INFORMATION: Any amino acid or absent
<220> FEATURE:
<221> NAME/KEY: MOD_RES
<222> LOCATION: (349)..(353)
<223> OTHER INFORMATION: Any amino acid or absent
<220> FEATURE:
<221> NAME/KEY: MOD_RES
<222> LOCATION: (357)..(376)
<223> OTHER INFORMATION: Any amino acid or absent
<220> FEATURE:
<221> NAME/KEY: MOD_RES
<222> LOCATION: (379)..(379)
<223> OTHER INFORMATION: Any amino acid or absent
```

-continued

```
<220> FEATURE:
<221> NAME/KEY: MOD_RES
<222> LOCATION: (384)..(386)
<223> OTHER INFORMATION: Any amino acid or absent
<220> FEATURE:
<221> NAME/KEY: MOD_RES
<222> LOCATION: (388)..(391)
<223> OTHER INFORMATION: Any amino acid or absent
<220> FEATURE:
<221> NAME/KEY: MOD_RES
<222> LOCATION: (393)..(393)
<223> OTHER INFORMATION: Any amino acid or absent
<220> FEATURE:
<221> NAME/KEY: MOD_RES
<222> LOCATION: (399)..(399)
<223> OTHER INFORMATION: Any amino acid or absent
<220> FEATURE:
<221> NAME/KEY: MOD_RES
<222> LOCATION: (402)..(402)
<223> OTHER INFORMATION: Any amino acid or absent
<220> FEATURE:
<221> NAME/KEY: MOD_RES
<222> LOCATION: (409)..(409)
<223> OTHER INFORMATION: Any amino acid or absent
<220> FEATURE:
<221> NAME/KEY: MOD_RES
<222> LOCATION: (416)..(416)
<223> OTHER INFORMATION: Any amino acid or absent
<220> FEATURE:
<221> NAME/KEY: MOD_RES
<222> LOCATION: (423)..(469)
<223> OTHER INFORMATION: Any amino acid or absent
<220> FEATURE:
<221> NAME/KEY: MOD_RES
<222> LOCATION: (471)..(507)
<223> OTHER INFORMATION: Any amino acid or absent
<220> FEATURE:
<221> NAME/KEY: MOD_RES
<222> LOCATION: (509)..(511)
<223> OTHER INFORMATION: Any amino acid or absent

<400> SEQUENCE: 4

Xaa Xaa Xaa Xaa Xaa Xaa Xaa Xaa Xaa Xaa Xaa Xaa Xaa Xaa Xaa
1               5                   10                  15

Xaa Xaa Xaa Xaa Gly Ile Thr Xaa Xaa Lys Xaa Xaa Xaa Xaa Xaa
            20                  25                  30

Xaa Xaa Xaa Xaa Gly Glu Xaa Xaa Xaa Xaa Gly Xaa Ile Pro Leu Xaa
        35                  40                  45

Xaa Xaa Xaa Thr Lys Ser His Phe Xaa Asn Xaa Arg Xaa Thr Lys Xaa
    50                  55                  60

Xaa Lys Xaa Xaa Pro Xaa Xaa Leu Asn Cys Thr Asp Xaa Xaa Xaa
65              70                  75                  80

Xaa Xaa Xaa Xaa Pro Lys Xaa Xaa Gly Asn Thr Pro Ser Ala Lys Xaa
            85                  90                  95

Xaa Xaa Xaa His Glu Val Arg Pro Val Thr Xaa Xaa Xaa Phe Xaa Xaa
        100                 105                 110

Xaa Xaa Xaa Xaa Xaa Xaa Xaa Xaa Xaa Xaa Xaa Xaa Xaa Xaa Gly
    115                 120                 125

Xaa Glu His Xaa Arg Xaa Xaa Asn Tyr Asn Xaa Ile Asp Xaa Glu Xaa
130                 135                 140

Ala Pro Xaa Xaa Xaa Xaa Xaa Xaa Gly Thr Ser Arg Xaa Xaa Pro Asn
145                 150                 155                 160

Val Thr Xaa Arg Ser Xaa Xaa Xaa Xaa Xaa Xaa Trp Ala Val Pro
            165                 170                 175

Lys Xaa Asp Ser Asn Xaa Xaa Xaa Xaa Xaa Xaa Xaa Xaa Xaa
        180                 185                 190
```

```
Xaa Xaa Ile Cys Thr Glu Gly Glu Xaa Xaa Xaa Xaa Xaa Xaa
        195                 200                 205

His Ser Asp Asn Lys Thr Gln Met Val Xaa Xaa Xaa Xaa Xaa
    210                 215                 220

Pro Xaa Lys Phe Xaa Xaa Xaa Xaa Xaa Xaa Xaa Xaa Xaa Xaa
225             230                 235                 240

Xaa Xaa Xaa Xaa Asp Xaa Xaa Asn Xaa Thr Glu Xaa Xaa Xaa
            245                 250                 255

Gln Ser Gly Xaa Xaa Xaa Xaa Xaa Xaa Xaa Lys Ser Gly Xaa
            260                 265                 270

Xaa Xaa Xaa Xaa Thr Xaa Gln Xaa Xaa Xaa Xaa Xaa Xaa Xaa
            275                 280                 285

Xaa Cys Xaa Xaa Xaa Xaa Xaa Xaa Xaa Xaa Gly Thr Leu Pro Leu
        290                 295                 300

Ile Gly Glu Xaa Asp Xaa Xaa Xaa Xaa Lys Tyr Xaa Xaa Xaa Asn Lys
305             310                 315                 320

Ser Lys Pro Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Asn Xaa Xaa Xaa Xaa
            340                 345                 350

Xaa Pro Pro Ala Xaa Xaa Xaa Xaa Xaa Xaa Xaa Xaa Xaa Xaa
    355                 360                 365

Xaa Xaa Xaa Xaa Xaa Xaa Xaa Glu Gly Xaa Ile Ala Gly Trp Xaa
        370                 375                 380

Xaa Xaa Thr Xaa Xaa Xaa Xaa His Xaa Val Ala Val Ala Ala Xaa Leu
385             390                 395                 400

Lys Xaa Thr Gln Glu Ala Ile Asn Xaa Ile Thr Lys Asn Leu Asn Xaa
            405                 410                 415

Leu Ser Glu Leu Glu Val Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa
            435                 440                 445

Xaa Xaa Xaa Xaa Xaa Xaa Xaa Xaa Xaa Xaa Xaa Xaa Xaa
            450                 455                 460

Xaa Xaa Xaa Xaa Xaa Ile Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Gln Xaa Xaa Xaa Asp
            500                 505                 510

<210> SEQ ID NO 5
<211> LENGTH: 512
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(20)
<223> OTHER INFORMATION: Any amino acid or absent
<220> FEATURE:
<221> NAME/KEY: MOD_RES
<222> LOCATION: (24)..(25)
<223> OTHER INFORMATION: Any amino acid or absent
<220> FEATURE:
<221> NAME/KEY: MOD_RES
```

-continued

```
<222> LOCATION: (27)..(36)
<223> OTHER INFORMATION: Any amino acid or absent
<220> FEATURE:
<221> NAME/KEY: MOD_RES
<222> LOCATION: (39)..(42)
<223> OTHER INFORMATION: Any amino acid or absent
<220> FEATURE:
<221> NAME/KEY: MOD_RES
<222> LOCATION: (44)..(44)
<223> OTHER INFORMATION: Any amino acid or absent
<220> FEATURE:
<221> NAME/KEY: MOD_RES
<222> LOCATION: (48)..(51)
<223> OTHER INFORMATION: Any amino acid or absent
<220> FEATURE:
<221> NAME/KEY: MOD_RES
<222> LOCATION: (57)..(57)
<223> OTHER INFORMATION: Any amino acid or absent
<220> FEATURE:
<221> NAME/KEY: MOD_RES
<222> LOCATION: (59)..(59)
<223> OTHER INFORMATION: Any amino acid or absent
<220> FEATURE:
<221> NAME/KEY: MOD_RES
<222> LOCATION: (61)..(61)
<223> OTHER INFORMATION: Any amino acid or absent
<220> FEATURE:
<221> NAME/KEY: MOD_RES
<222> LOCATION: (64)..(66)
<223> OTHER INFORMATION: Any amino acid or absent
<220> FEATURE:
<221> NAME/KEY: MOD_RES
<222> LOCATION: (68)..(69)
<223> OTHER INFORMATION: Any amino acid or absent
<220> FEATURE:
<221> NAME/KEY: MOD_RES
<222> LOCATION: (71)..(72)
<223> OTHER INFORMATION: Any amino acid or absent
<220> FEATURE:
<221> NAME/KEY: MOD_RES
<222> LOCATION: (78)..(84)
<223> OTHER INFORMATION: Any amino acid or absent
<220> FEATURE:
<221> NAME/KEY: MOD_RES
<222> LOCATION: (87)..(88)
<223> OTHER INFORMATION: Any amino acid or absent
<220> FEATURE:
<221> NAME/KEY: MOD_RES
<222> LOCATION: (96)..(99)
<223> OTHER INFORMATION: Any amino acid or absent
<220> FEATURE:
<221> NAME/KEY: MOD_RES
<222> LOCATION: (107)..(109)
<223> OTHER INFORMATION: Any amino acid or absent
<220> FEATURE:
<221> NAME/KEY: MOD_RES
<222> LOCATION: (111)..(127)
<223> OTHER INFORMATION: Any amino acid or absent
<220> FEATURE:
<221> NAME/KEY: MOD_RES
<222> LOCATION: (129)..(129)
<223> OTHER INFORMATION: Any amino acid or absent
<220> FEATURE:
<221> NAME/KEY: MOD_RES
<222> LOCATION: (132)..(132)
<223> OTHER INFORMATION: Any amino acid or absent
<220> FEATURE:
<221> NAME/KEY: MOD_RES
<222> LOCATION: (134)..(135)
<223> OTHER INFORMATION: Any amino acid or absent
<220> FEATURE:
<221> NAME/KEY: MOD_RES
<222> LOCATION: (139)..(139)
<223> OTHER INFORMATION: Any amino acid or absent
<220> FEATURE:
<221> NAME/KEY: MOD_RES
<222> LOCATION: (142)..(142)
<223> OTHER INFORMATION: Any amino acid or absent
<220> FEATURE:
```

```
<221> NAME/KEY: MOD_RES
<222> LOCATION: (144)..(144)
<223> OTHER INFORMATION: Any amino acid or absent
<220> FEATURE:
<221> NAME/KEY: MOD_RES
<222> LOCATION: (147)..(152)
<223> OTHER INFORMATION: Any amino acid or absent
<220> FEATURE:
<221> NAME/KEY: MOD_RES
<222> LOCATION: (157)..(158)
<223> OTHER INFORMATION: Any amino acid or absent
<220> FEATURE:
<221> NAME/KEY: MOD_RES
<222> LOCATION: (163)..(163)
<223> OTHER INFORMATION: Any amino acid or absent
<220> FEATURE:
<221> NAME/KEY: MOD_RES
<222> LOCATION: (166)..(172)
<223> OTHER INFORMATION: Any amino acid or absent
<220> FEATURE:
<221> NAME/KEY: MOD_RES
<222> LOCATION: (178)..(178)
<223> OTHER INFORMATION: Any amino acid or absent
<220> FEATURE:
<221> NAME/KEY: MOD_RES
<222> LOCATION: (182)..(194)
<223> OTHER INFORMATION: Any amino acid or absent
<220> FEATURE:
<221> NAME/KEY: MOD_RES
<222> LOCATION: (201)..(208)
<223> OTHER INFORMATION: Any amino acid or absent
<220> FEATURE:
<221> NAME/KEY: MOD_RES
<222> LOCATION: (218)..(224)
<223> OTHER INFORMATION: Any amino acid or absent
<220> FEATURE:
<221> NAME/KEY: MOD_RES
<222> LOCATION: (226)..(226)
<223> OTHER INFORMATION: Any amino acid or absent
<220> FEATURE:
<221> NAME/KEY: MOD_RES
<222> LOCATION: (229)..(244)
<223> OTHER INFORMATION: Any amino acid or absent
<220> FEATURE:
<221> NAME/KEY: MOD_RES
<222> LOCATION: (246)..(247)
<223> OTHER INFORMATION: Any amino acid or absent
<220> FEATURE:
<221> NAME/KEY: MOD_RES
<222> LOCATION: (249)..(249)
<223> OTHER INFORMATION: Any amino acid or absent
<220> FEATURE:
<221> NAME/KEY: MOD_RES
<222> LOCATION: (252)..(256)
<223> OTHER INFORMATION: Any amino acid or absent
<220> FEATURE:
<221> NAME/KEY: MOD_RES
<222> LOCATION: (260)..(268)
<223> OTHER INFORMATION: Any amino acid or absent
<220> FEATURE:
<221> NAME/KEY: MOD_RES
<222> LOCATION: (272)..(276)
<223> OTHER INFORMATION: Any amino acid or absent
<220> FEATURE:
<221> NAME/KEY: MOD_RES
<222> LOCATION: (278)..(278)
<223> OTHER INFORMATION: Any amino acid or absent
<220> FEATURE:
<221> NAME/KEY: MOD_RES
<222> LOCATION: (280)..(289)
<223> OTHER INFORMATION: Any amino acid or absent
<220> FEATURE:
<221> NAME/KEY: MOD_RES
<222> LOCATION: (291)..(299)
<223> OTHER INFORMATION: Any amino acid or absent
<220> FEATURE:
<221> NAME/KEY: MOD_RES
<222> LOCATION: (310)..(313)
<223> OTHER INFORMATION: Any amino acid or absent
```

```
<220> FEATURE:
<221> NAME/KEY: MOD_RES
<222> LOCATION: (316)..(318)
<223> OTHER INFORMATION: Any amino acid or absent
<220> FEATURE:
<221> NAME/KEY: MOD_RES
<222> LOCATION: (324)..(347)
<223> OTHER INFORMATION: Any amino acid or absent
<220> FEATURE:
<221> NAME/KEY: MOD_RES
<222> LOCATION: (349)..(353)
<223> OTHER INFORMATION: Any amino acid or absent
<220> FEATURE:
<221> NAME/KEY: MOD_RES
<222> LOCATION: (357)..(376)
<223> OTHER INFORMATION: Any amino acid or absent
<220> FEATURE:
<221> NAME/KEY: MOD_RES
<222> LOCATION: (379)..(379)
<223> OTHER INFORMATION: Any amino acid or absent
<220> FEATURE:
<221> NAME/KEY: MOD_RES
<222> LOCATION: (384)..(386)
<223> OTHER INFORMATION: Any amino acid or absent
<220> FEATURE:
<221> NAME/KEY: MOD_RES
<222> LOCATION: (388)..(391)
<223> OTHER INFORMATION: Any amino acid or absent
<220> FEATURE:
<221> NAME/KEY: MOD_RES
<222> LOCATION: (393)..(393)
<223> OTHER INFORMATION: Any amino acid or absent
<220> FEATURE:
<221> NAME/KEY: MOD_RES
<222> LOCATION: (399)..(399)
<223> OTHER INFORMATION: Any amino acid or absent
<220> FEATURE:
<221> NAME/KEY: MOD_RES
<222> LOCATION: (402)..(402)
<223> OTHER INFORMATION: Any amino acid or absent
<220> FEATURE:
<221> NAME/KEY: MOD_RES
<222> LOCATION: (409)..(409)
<223> OTHER INFORMATION: Any amino acid or absent
<220> FEATURE:
<221> NAME/KEY: MOD_RES
<222> LOCATION: (416)..(416)
<223> OTHER INFORMATION: Any amino acid or absent
<220> FEATURE:
<221> NAME/KEY: MOD_RES
<222> LOCATION: (423)..(469)
<223> OTHER INFORMATION: Any amino acid or absent
<220> FEATURE:
<221> NAME/KEY: MOD_RES
<222> LOCATION: (471)..(507)
<223> OTHER INFORMATION: Any amino acid or absent
<220> FEATURE:
<221> NAME/KEY: MOD_RES
<222> LOCATION: (509)..(511)
<223> OTHER INFORMATION: Any amino acid or absent

<400> SEQUENCE: 5

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Gly Ile Thr Xaa Xaa Asn Xaa Xaa Xaa Xaa Xaa Xaa
            20                  25                  30

Xaa Xaa Xaa Xaa Gly Glu Xaa Xaa Xaa Xaa Gly Xaa Ile Pro Leu Xaa
        35                  40                  45

Xaa Xaa Xaa Thr Lys Ser Tyr Phe Xaa Asn Xaa Lys Xaa Thr Lys Xaa
    50                  55                  60

Xaa Xaa Lys Xaa Xaa Pro Xaa Xaa Leu Asn Cys Thr Asp Xaa Xaa Xaa
65                  70                  75                  80

Xaa Xaa Xaa Xaa Pro Met Xaa Xaa Gly Thr Ile Pro Ser Ala Lys Xaa
```

-continued

```
                 85                  90                  95
Xaa Xaa Xaa His Glu Val Arg Pro Val Thr Xaa Xaa Xaa Phe Xaa Xaa
            100                 105                 110
Xaa Xaa Xaa Xaa Xaa Xaa Xaa Xaa Xaa Xaa Xaa Xaa Xaa Xaa Xaa Gly
            115                 120                 125
Xaa Glu Asn Xaa Arg Xaa Xaa Thr His Asn Xaa Ile Asn Xaa Glu Xaa
            130                 135                 140
Ala Pro Xaa Xaa Xaa Xaa Xaa Gly Thr Ser Gly Xaa Xaa Pro Asn
145                 150                 155                 160
Ala Thr Xaa Lys Asn Xaa Xaa Xaa Xaa Xaa Xaa Trp Ala Val Pro
            165                 170                 175
Lys Xaa Asp Asn Asn Xaa Xaa Xaa Xaa Xaa Xaa Xaa Xaa Xaa Xaa
            180                 185                 190
Xaa Xaa Ile Cys Thr Glu Gly Glu Xaa Xaa Xaa Xaa Xaa Xaa
            195                 200                 205
His Ser Asp Asn Lys Thr Gln Met Lys Xaa Xaa Xaa Xaa Xaa Xaa
210                 215                 220
Pro Xaa Lys Phe Xaa Xaa Xaa Xaa Xaa Xaa Xaa Xaa Xaa Xaa Xaa
225                 230                 235                 240
Xaa Xaa Xaa Xaa Gly Xaa Xaa Asp Xaa Thr Glu Xaa Xaa Xaa Xaa
                245                 250                 255
Gln Ser Gly Xaa Xaa Xaa Xaa Xaa Xaa Xaa Lys Ser Gly Xaa
            260                 265                 270
Xaa Xaa Xaa Xaa Thr Xaa Gln Xaa Xaa Xaa Xaa Xaa Xaa Xaa Xaa
            275                 280                 285
Xaa Cys Xaa Xaa Xaa Xaa Xaa Xaa Xaa Xaa Gly Ser Leu Pro Leu
            290                 295                 300
Ile Gly Glu Ala Asp Xaa Xaa Xaa Xaa Lys Tyr Xaa Xaa Xaa Asn Lys
305                 310                 315                 320
Ser Lys Pro Xaa Xaa Xaa Xaa Xaa Xaa Xaa Xaa Xaa Xaa Xaa
            325                 330                 335
Xaa Xaa Xaa Xaa Xaa Xaa Xaa Xaa Xaa Xaa Asn Xaa Xaa Xaa Xaa
            340                 345                 350
Xaa Pro Pro Ala Xaa Xaa Xaa Xaa Xaa Xaa Xaa Xaa Xaa Xaa Xaa
            355                 360                 365
Xaa Xaa Xaa Xaa Xaa Xaa Xaa Glu Gly Xaa Ile Ala Gly Trp Xaa
            370                 375                 380
Xaa Xaa Thr Xaa Xaa Xaa Xaa His Xaa Val Ala Val Ala Ala Xaa Leu
385                 390                 395                 400
Lys Xaa Thr Gln Glu Ala Ile Asn Xaa Ile Thr Lys Asn Leu Asn Xaa
                405                 410                 415
Leu Ser Glu Leu Glu Val Xaa Xaa Xaa Xaa Xaa Xaa Xaa Xaa Xaa
            420                 425                 430
Xaa Xaa Xaa Xaa Xaa Xaa Xaa Xaa Xaa Xaa Xaa Xaa Xaa Xaa Xaa
            435                 440                 445
Xaa Xaa Xaa Xaa Xaa Xaa Xaa Xaa Xaa Xaa Xaa Xaa Xaa Xaa Xaa
            450                 455                 460
Xaa Xaa Xaa Xaa Xaa Ile Xaa Xaa Xaa Xaa Xaa Xaa Xaa Xaa Xaa
465                 470                 475                 480
Xaa Xaa Xaa Xaa Xaa Xaa Xaa Xaa Xaa Xaa Xaa Xaa Xaa Xaa Xaa
            485                 490                 495
Xaa Xaa Xaa Xaa Xaa Xaa Xaa Xaa Xaa Xaa Gln Xaa Xaa Xaa Asp
            500                 505                 510
```

<210> SEQ ID NO 6
<211> LENGTH: 568
<212> TYPE: PRT
<213> ORGANISM: Influenza virus

<400> SEQUENCE: 6

```
Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Lys
        35                  40                  45

Thr Arg Gly Lys Leu Cys Pro Asn Cys Leu Asn Cys Thr Asp Leu Asp
    50                  55                  60

Val Ala Leu Gly Arg Pro Lys Cys Met Gly Thr Ile Pro Ser Ala Lys
65                  70                  75                  80

Ala Ser Ile Leu His Glu Val Lys Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu Asn Ile Arg Leu Ser Thr Arg Asn Val Ile Asn Ala Glu
        115                 120                 125

Arg Ala Pro Gly Gly Pro Tyr Ile Ile Gly Thr Ser Gly Ser Cys Pro
    130                 135                 140

Asn Val Thr Asn Gly Asn Gly Phe Phe Ala Thr Met Ala Trp Ala Val
145                 150                 155                 160

Pro Lys Asp Asn Lys Thr Ala Thr Asn Pro Leu Thr Val Glu Val Pro
                165                 170                 175

Tyr Ile Cys Thr Lys Gly Glu Asp Gln Ile Thr Val Trp Gly Phe His
            180                 185                 190

Ser Asp Thr Glu Thr Gln Met Val Lys Leu Tyr Gly Asp Ser Lys Pro
        195                 200                 205

Gln Lys Phe Thr Ser Ser Ala Asn Gly Val Thr Thr His Tyr Val Ser
    210                 215                 220

Gln Ile Gly Gly Phe Pro Asn Gln Thr Glu Asp Gly Gly Leu Pro Gln
225                 230                 235                 240

Ser Gly Arg Ile Val Val Asp Tyr Met Val Gln Lys Pro Gly Lys Thr
                245                 250                 255

Gly Thr Ile Val Tyr Gln Arg Gly Val Leu Leu Pro Gln Lys Val Trp
            260                 265                 270

Cys Ala Ser Gly Arg Ser Lys Val Ile Lys Gly Ser Leu Pro Leu Ile
        275                 280                 285

Gly Glu Ala Asp Cys Leu His Glu Lys Tyr Gly Gly Leu Asn Lys Ser
    290                 295                 300

Lys Pro Tyr Tyr Thr Gly Glu His Ala Lys Ala Ile Gly Asn Cys Pro
305                 310                 315                 320

Ile Trp Val Lys Thr Pro Leu Lys Leu Ala Asn Gly Thr Lys Tyr Arg
                325                 330                 335

Pro Pro Ala Lys Leu Leu Lys Glu Arg Gly Phe Phe Gly Ala Ile Ala
            340                 345                 350

Gly Phe Leu Glu Gly Gly Trp Glu Gly Met Ile Ala Gly Trp His Gly
        355                 360                 365

Tyr Thr Ser His Gly Ala His Gly Val Ala Val Ala Ala Asp Leu Lys
```

```
                370                 375                 380
Ser Thr Gln Glu Ala Ile Asn Lys Ile Thr Lys Asn Leu Asn Ser Leu
385                 390                 395                 400

Ser Glu Leu Glu Val Lys Asn Leu Gln Arg Leu Ser Gly Ala Met Asp
                405                 410                 415

Glu Leu His Asn Glu Ile Leu Glu Leu Asp Glu Lys Val Asp Asp Leu
                420                 425                 430

Arg Ala Asp Thr Ile Ser Ser Gln Ile Glu Leu Ala Val Leu Leu Ser
            435                 440                 445

Asn Glu Gly Ile Ile Asn Ser Glu Asp Glu His Leu Leu Ala Leu Glu
    450                 455                 460

Arg Lys Leu Lys Lys Met Leu Gly Pro Ser Ala Val Asp Ile Gly Asn
465                 470                 475                 480

Gly Cys Phe Glu Thr Lys His Lys Cys Asn Gln Thr Cys Leu Asp Arg
                485                 490                 495

Ile Ala Ala Gly Thr Phe Asn Ala Gly Glu Phe Ser Leu Pro Thr Phe
                500                 505                 510

Asp Ser Leu Asn Ile Thr Ala Ala Ser Leu Asn Asp Asp Gly Leu Asp
            515                 520                 525

Asn His Thr Ile Leu Leu Tyr Tyr Ser Thr Ala Ala Ser Ser Leu Ala
    530                 535                 540

Val Thr Leu Met Ile Ala Ile Phe Ile Val Tyr Met Val Ser Arg Asp
545                 550                 555                 560

Asn Val Ser Cys Ser Ile Cys Leu
                565

<210> SEQ ID NO 7
<211> LENGTH: 569
<212> TYPE: PRT
<213> ORGANISM: Influenza virus

<400> SEQUENCE:

Pro Tyr Ile Cys Ala Glu Gly Glu Asp Gln Ile Thr Val Trp Gly Phe
                180                 185                 190

His Ser Asp Asp Lys Thr Gln Met Lys Asn Leu Tyr Gly Asp Ser Asn
            195                 200                 205

Pro Gln Lys Phe Thr Ser Ser Ala Asn Gly Val Thr Thr His Tyr Val
        210                 215                 220

Ser Gln Ile Gly Gly Phe Pro Asp Gln Thr Glu Asp Gly Gly Leu Pro
225                 230                 235                 240

Gln Ser Gly Arg Ile Val Val Asp Tyr Met Met Gln Lys Pro Gly Lys
                245                 250                 255

Thr Gly Thr Ile Val Tyr Gln Arg Gly Val Leu Leu Pro Gln Lys Val
            260                 265                 270

Trp Cys Ala Ser Gly Arg Ser Lys Val Ile Lys Gly Ser Leu Pro Leu
        275                 280                 285

Ile Gly Glu Ala Asp Cys Leu His Glu Lys Tyr Gly Gly Leu Asn Lys
290                 295                 300

Ser Lys Pro Tyr Tyr Thr Gly Glu His Ala Lys Ala Ile Gly Asn Cys
305                 310                 315                 320

Pro Ile Trp Val Lys Thr Pro Leu Lys Leu Ala Asn Gly Thr Lys Tyr
                325                 330                 335

Arg Pro Pro Ala Lys Leu Leu Lys Glu Arg Gly Phe Phe Gly Ala Ile
            340                 345                 350

Ala Gly Phe Leu Glu Gly Gly Trp Glu Gly Met Ile Ala Gly Trp His
        355                 360                 365

Gly Tyr Thr Ser His Gly Ala His Gly Val Ala Val Ala Ala Asp Leu
        370                 375                 380

Lys Ser Thr Gln Glu Ala Ile Asn Lys Ile Thr Lys Asn Leu Asn Ser
385                 390                 395                 400

Leu Ser Glu Leu Glu Val Lys Asn Leu Gln Arg Leu Ser Gly Ala Met
                405                 410                 415

Asp Glu Leu His Asn Glu Ile Leu Glu Leu Asp Glu Lys Val Asp Asp
            420                 425                 430

Leu Arg Ala Asp Thr Ile Ser Ser Gln Ile Glu Leu Ala Val Leu Leu
        435                 440                 445

Ser Asn Glu Gly Ile Ile Asn Ser Glu Asp Glu His Leu Leu Ala Leu
450                 455                 460

Glu Arg Lys Leu Lys Lys Met Leu Gly Pro Ser Ala Val Asp Ile Gly
465                 470                 475                 480

Asn Gly Cys Phe Glu Thr Lys His Lys Cys Asn Gln Thr Cys Leu Asp
                485                 490                 495

Arg Ile Ala Ala Gly Thr Phe Asn Ala Gly Glu Phe Ser Leu Pro Thr
            500                 505                 510

Phe Asp Ser Leu Asn Ile Thr Ala Ala Ser Leu Asn Asp Asp Gly Leu
        515                 520                 525

Asp Asn His Thr Ile Leu Leu Tyr Tyr Ser Thr Ala Ala Ser Ser Leu
530                 535                 540

Ala Val Thr Leu Met Leu Ala Ile Phe Ile Val Tyr Met Val Ser Arg
545                 550                 555                 560

Asp Asn Val Ser Cys Ser Ile Cys Leu
                565

<210> SEQ ID NO 8
<211> LENGTH: 568
<212> TYPE: PRT

<213> ORGANISM: Influenza virus

<400> SEQUENCE: 8

Asp Arg Ile Cys Thr Gly Ile Thr Ser Ser Asn Ser Pro His Val Val
1               5 10 15

Lys Thr Ala Thr Gln Gly Glu Val Asn Val Thr Gly Val Ile Pro Leu
20 25 30

Thr Thr Thr Pro Thr Lys Ser His Phe Ala Asn Leu Lys Gly Thr Lys
35 40 45

Thr Arg Gly Lys Leu Cys Pro Asn Cys Leu Asn Cys Thr Asp Leu Asp
50 55 60

Val Ala Leu Gly Arg Pro Met Cys Val Gly Thr Thr Pro Ser Ala Lys
65 70 75 80

Ala Ser Ile Leu His Glu Val Arg Pro Val Thr Ser Gly Cys Phe Pro
85 90 95

Ile Met His Asp Arg Thr Lys Ile Arg Gln Leu Pro Asn Leu Leu Arg
100 105 110

Gly Tyr Glu Asn Ile Arg Leu Ser Thr Gln Asn Val Ile Asn Ala Glu
115 120 125

Arg Ala Pro Gly Gly Pro Tyr Arg Leu Gly Thr Ser Gly Ser Cys Pro
130 135 140

Asn Val Thr Ser Arg Asp Gly Phe Phe Ala Thr Met Ala Trp Ala Val
145 150 155 160

Pro Arg Asp Asn Lys Thr Ala Thr Asn Pro Leu Thr Val Glu Val Pro
165 170 175

Tyr Ile Cys Thr Lys Gly Glu Asp Gln Ile Thr Val Trp Gly Phe His
180 185 190

Ser Asp Asn Lys Thr Gln Met Lys Asn Leu Tyr Gly Asp Ser Asn Pro
195 200 205

Gln Lys Phe Thr Ser Ser Ala Asn Gly Val Thr Thr His Tyr Val Ser
210 215 220

Gln Ile Gly Gly Phe Pro Asn Gln Thr Glu Asp Gly Gly Leu Pro Gln
225 230 235 240

Ser Gly Arg Ile Val Val Asp Tyr Met Val Gln Lys Pro Gly Lys Thr
245 250 255

Gly Thr Ile Val Tyr Gln Arg Gly Val Leu Leu Pro Gln Lys Val Trp
260 265 270

Cys Ala Ser Gly Arg Ser Lys Val Ile Lys Gly Ser Leu Pro Leu Ile
275 280 285

Gly Glu Ala Asp Cys Leu His Glu Lys Tyr Gly Gly Leu Asn Lys Ser
290 295 300

Lys Pro Tyr Tyr Thr Gly Glu His Ala Lys Ala Ile Gly Asn Cys Pro
305 310 315 320

Ile Trp Val Lys Thr Pro Leu Lys Leu Ala Asn Gly Thr Lys Tyr Arg
325 330 335

Pro Pro Ala Lys Leu Leu Lys Glu Arg Gly Phe Phe Gly Ala Ile Ala
340 345 350

Gly Phe Leu Glu Gly Gly Trp Glu Gly Met Ile Ala Gly Trp His Gly
355 360 365

Tyr Thr Ser His Gly Ala His Gly Val Ala Val Ala Ala Asp Leu Lys
370 375 380

Ser Thr Gln Glu Ala Ile Asn Lys Ile Thr Lys Asn Leu Asn Ser Leu
385 390 395 400

Ser Glu Leu Glu Val Lys Asn Leu Gln Arg Leu Ser Gly Ala Met Asp
                405                 410                 415

Glu Leu His Asn Glu Ile Leu Glu Leu Asp Glu Lys Val Asp Asp Leu
            420                 425                 430

Arg Ala Asp Thr Ile Ser Ser Gln Ile Glu Leu Ala Val Leu Leu Ser
            435                 440                 445

Asn Glu Gly Ile Ile Asn Ser Glu Asp Glu His Leu Leu Ala Leu Glu
        450                 455                 460

Arg Lys Leu Lys Lys Met Leu Gly Pro Ser Ala Val Asp Ile Gly Asn
465                 470                 475                 480

Gly Cys Phe Glu Thr Lys His Lys Cys Asn Gln Thr Cys Leu Asp Arg
                485                 490                 495

Ile Ala Ala Gly Thr Phe Asn Ala Gly Glu Phe Ser Leu Pro Thr Phe
                500                 505                 510

Asp Ser Leu Asn Ile Thr Ala Ala Ser Leu Asn Asp Asp Gly Leu Asp
            515                 520                 525

Asn His Thr Ile Leu Leu Tyr Tyr Ser Thr Ala Ala Ser Ser Leu Ala
        530                 535                 540

Val Thr Leu Met Ile Ala Ile Phe Ile Val Tyr Met Val Ser Arg Asp
545                 550                 555                 560

Asn Val Ser Cys Ser Ile Cys Leu
                565

<210> SEQ ID NO 9
<211> LENGTH: 570
<212> TYPE: PRT
<213> ORGANISM: Influenza virus

<400> SEQUENCE: 9

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Glu
        35                  40                  45

Thr Arg Gly Lys Leu Cys Pro Lys Cys Leu Asn Cys Thr Asp Leu Asp
    50                  55                  60

Val Ala Leu Gly Arg Pro Lys Cys Thr Gly Lys Ile Pro Ser Ala Arg
65                  70                  75                  80

Val Ser Ile Leu His Glu Val Arg Pro Val Thr Ser Gly Cys Phe Pro
                85                  90                  95

Ile Met His Asp Arg Thr Lys Ile Arg Gln Leu Pro Asn Leu Leu Arg
                100                 105                 110

Gly Tyr Glu His Ile Arg Leu Ser Thr His Asn Val Ile Asn Ala Glu
            115                 120                 125

Asn Ala Pro Gly Gly Pro Tyr Lys Ile Gly Thr Ser Gly Ser Cys Pro
        130                 135                 140

Asn Ile Thr Asn Gly Asn Gly Phe Phe Ala Thr Met Ala Trp Ala Val
145                 150                 155                 160

Pro Lys Asn Asp Lys Asn Lys Thr Ala Thr Asn Pro Leu Thr Ile Glu
                165                 170                 175

Val Pro Tyr Ile Cys Thr Glu Gly Glu Asp Gln Ile Thr Val Trp Gly
            180                 185                 190

Phe His Ser Asp Asp Glu Thr Gln Met Ala Lys Leu Tyr Gly Asp Ser
        195                 200                 205

Lys Pro Gln Lys Phe Thr Ser Ala Asn Gly Val Thr Thr His Tyr
210                 215                 220

Val Ser Gln Ile Gly Gly Phe Pro Asn Gln Thr Glu Asp Gly Gly Leu
225                 230                 235                 240

Pro Gln Ser Gly Arg Ile Val Asp Tyr Met Val Gln Lys Ser Gly
                245                 250                 255

Lys Thr Gly Thr Ile Thr Tyr Gln Arg Gly Ile Leu Leu Pro Gln Lys
                260                 265                 270

Val Trp Cys Ala Ser Gly Arg Ser Lys Val Ile Lys Gly Ser Leu Pro
            275                 280                 285

Leu Ile Gly Glu Ala Asp Cys Leu His Glu Lys Tyr Gly Gly Leu Asn
        290                 295                 300

Lys Ser Lys Pro Tyr Tyr Thr Gly Glu His Ala Lys Ala Ile Gly Asn
305                 310                 315                 320

Cys Pro Ile Trp Val Lys Thr Pro Leu Lys Leu Ala Asn Gly Thr Lys
                325                 330                 335

Tyr Arg Pro Pro Ala Lys Leu Leu Lys Glu Arg Gly Phe Phe Gly Ala
                340                 345                 350

Ile Ala Gly Phe Leu Glu Gly Gly Trp Glu Gly Met Ile Ala Gly Trp
            355                 360                 365

His Gly Tyr Thr Ser His Gly Ala His Gly Val Ala Val Ala Ala Asp
        370                 375                 380

Leu Lys Ser Thr Gln Glu Ala Ile Asn Lys Ile Thr Lys Asn Leu Asn
385                 390                 395                 400

Ser Leu Ser Glu Leu Glu Val Lys Asn Leu Gln Arg Leu Ser Gly Ala
                405                 410                 415

Met Asp Glu Leu His Asn Glu Ile Leu Glu Leu Asp Glu Lys Val Asp
            420                 425                 430

Asp Leu Arg Ala Asp Thr Ile Ser Ser Gln Ile Glu Leu Ala Val Leu
        435                 440                 445

Leu Ser Asn Glu Gly Ile Ile Asn Ser Glu Asp Glu His Leu Leu Ala
450                 455                 460

Leu Glu Arg Lys Leu Lys Lys Met Leu Gly Pro Ser Ala Val Glu Ile
465                 470                 475                 480

Gly Asn Gly Cys Phe Glu Thr Lys His Lys Cys Asn Gln Thr Cys Leu
                485                 490                 495

Asp Arg Ile Ala Ala Gly Thr Phe Asp Ala Gly Glu Phe Ser Leu Pro
            500                 505                 510

Thr Phe Asp Ser Leu Asn Ile Thr Ala Ala Ser Leu Asn Asp Asp Gly
        515                 520                 525

Leu Asp Asn His Thr Ile Leu Leu Tyr Tyr Ser Thr Ala Ala Ser Ser
530                 535                 540

Leu Ala Val Thr Leu Met Ile Ala Ile Phe Val Val Tyr Met Val Ser
545                 550                 555                 560

Arg Asp Asn Val Ser Cys Ser Ile Cys Leu
                565                 570

<210> SEQ ID NO 10

<400> SEQUENCE: 10

000

<210> SEQ ID NO 11

```
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gly Val Thr Ala Ser Ser Trp Leu Thr His His Pro Ser Asn Gly Asp
1               5                   10                  15

Gln Gln Thr Leu Lys Asp Gln Glu Gly Arg
            20                  25

<210> SEQ ID NO 12
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Val Ser Ala Ser Ser Trp Leu Thr His His Pro Ser Thr Ala Asp
1               5                   10                  15

Gln Gln Thr Leu Lys Asp Gln Glu Gly Arg
            20                  25

<210> SEQ ID NO 13
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Gly Val Thr Ala Ser Lys Trp Leu Val His His Pro Ser Thr Ala Asp
1               5                   10                  15

Gln Gln Ser Leu Lys Asp Gln Glu Gly Arg
            20                  25

<210> SEQ ID NO 14
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gly Val Ser Ala Ser Ser Trp Leu Thr His His Pro Pro Asn Gly Asp
1               5                   10                  15

Gln Arg Ala Leu Lys Asp Gln Glu Gly Arg
            20                  25

<210> SEQ ID NO 15
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 15

Gly Val Ser Ala Ser Ser Trp Leu Thr His His Pro Pro Asn Gly Asp
1               5                   10                  15

Gln Lys Thr Leu Lys Asp Gln Glu Gly Arg
            20                  25

<210> SEQ ID NO 16
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gly Val Ser Ala Ala Ser Trp Leu Thr His His Pro Ser Thr Ala Asp
1               5                   10                  15

Gln Gln Thr Leu Lys Asp Gln Glu Gly Arg
            20                  25

<210> SEQ ID NO 17
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gly Val Thr Ala Ala Lys Trp Leu Val His His Pro Ser Thr Ala Asp
1               5                   10                  15

Gln Gln Ser Leu Lys Asp Gln Glu Gly Arg
            20                  25

<210> SEQ ID NO 18
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gly Val Ser Ala Ala Ser Trp Leu Thr His His Pro Pro Asn Gly Asp
1               5                   10                  15

Gln Arg Ala Leu Lys Asp Gln Glu Gly Arg
            20                  25

<210> SEQ ID NO 19
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gly Val Ser Ala Ala Ser Trp Leu Thr His His Pro Pro Asn Gly Asp
1               5                   10                  15

Gln Lys Thr Leu Lys Asp Gln Glu Gly Arg
```

```
                        20                  25

<210> SEQ ID NO 20
<211> LENGTH: 54
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Cys Tyr Pro Thr Val Thr Gly Val Thr Ala Ser Cys Ser Lys Ser Ser
1               5                   10                  15

Phe Leu Trp Leu Thr Gly Val His His Pro Ser Asn Ile Gly Asp Gln
            20                  25                  30

Gln Thr Leu Tyr Gln Glu Ile Ala Lys Arg Pro Lys Val Arg Asp Gln
        35                  40                  45

Glu Gly Arg Met Asn Ile
    50

<210> SEQ ID NO 21
<211> LENGTH: 54
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Cys Tyr Pro Asp Val Thr Gly Val Ser Ala Ser Cys Ser Ala Ser Ser
1               5                   10                  15

Phe Leu Trp Leu Thr Lys Val His His Pro Ser Thr Ile Ala Asp Gln
            20                  25                  30

Gln Thr Leu Tyr His Glu Ile Ala Ile Arg Pro Lys Val Arg Asp Gln
        35                  40                  45

Glu Gly Arg Ile Asn Ile
    50

<210> SEQ ID NO 22
<211> LENGTH: 54
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Cys Tyr Pro Asp Ser Asn Gly Val Thr Ala Ser Cys Pro Ala Lys Ser
1               5                   10                  15

Phe Leu Trp Leu Val Lys Val His His Pro Ser Thr Ser Ala Asp Gln
            20                  25                  30

Gln Ser Leu Tyr Gln Glu Ile Ala Ile Arg Pro Lys Val Arg Asp Gln
        35                  40                  45

Glu Gly Arg Met Asn Ile
    50

<210> SEQ ID NO 23
<211> LENGTH: 54
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 23

Cys Tyr Pro Thr Val Thr Gly Val Ser Ala Ser Cys Ser Lys Ser Ser
1               5                  10                  15

Phe Leu Trp Leu Thr Gly Val His His Pro Pro Asn Ile Gly Asp Gln
            20                  25                  30

Arg Ala Leu Tyr His Glu Ile Ala Lys Arg Pro Lys Val Arg Asp Gln
        35                  40                  45

Glu Gly Arg Ile Asn Ile
    50

<210> SEQ ID NO 24
<211> LENGTH: 54
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Cys Tyr Pro Thr Val Thr Gly Val Ser Ala Ser Cys Pro Glu Ser Ser
1               5                  10                  15

Phe Leu Trp Leu Thr Gly Val His His Pro Pro Asn Ile Gly Asp Gln
            20                  25                  30

Lys Thr Leu Tyr His Glu Ile Ala Lys Arg Pro Lys Val Arg Asp Gln
        35                  40                  45

Glu Gly Arg Ile Asn Ile
    50

<210> SEQ ID NO 25
<211> LENGTH: 55
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Cys Tyr Pro Thr Val Thr Lys Gly Val Thr Ala Ala Cys Ser Lys Ser
1               5                  10                  15

Ser Phe Ile Trp Leu Thr Gly Ile His His Pro Ser Asn Ile Gly Asp
            20                  25                  30

Gln Gln Thr Leu Tyr Gln Glu Ile Ala Lys Arg Pro Lys Val Arg Asp
        35                  40                  45

Gln Glu Gly Arg Met Asn Val
    50                  55

<210> SEQ ID NO 26
<211> LENGTH: 55
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26
```

```
Cys Tyr Pro Asp Val Thr Lys Gly Val Ser Ala Ala Cys Ser Ala Ser
1               5                   10                  15

Ser Phe Ile Trp Leu Thr Lys Ile His His Pro Ser Thr Ile Ala Asp
            20                  25                  30

Gln Gln Thr Leu Tyr His Glu Ile Ala Ile Arg Pro Lys Val Arg Asp
        35                  40                  45

Gln Glu Gly Arg Ile Asn Val
    50                  55

<210> SEQ ID NO 27
<211> LENGTH: 55
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Cys Tyr Pro Asp Ser Asn Lys Gly Val Thr Ala Ala Cys Pro Ala Lys
1               5                   10                  15

Ser Phe Ile Trp Leu Val Lys Ile His His Pro Ser Thr Ser Ala Asp
            20                  25                  30

Gln Gln Ser Leu Tyr Gln Glu Ile Ala Ile Arg Pro Lys Val Arg Asp
        35                  40                  45

Gln Glu Gly Arg Met Asn Val
    50                  55

<210> SEQ ID NO 28
<211> LENGTH: 55
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Cys Tyr Pro Thr Val Thr Lys Gly Val Ser Ala Ala Cys Ser Lys Ser
1               5                   10                  15

Ser Phe Ile Trp Leu Thr Gly Ile His His Pro Pro Asn Ile Gly Asp
            20                  25                  30

Gln Arg Ala Leu Tyr His Glu Ile Ala Lys Arg Pro Lys Val Arg Asp
        35                  40                  45

Gln Glu Gly Arg Ile Asn Val
    50                  55

<210> SEQ ID NO 29
<211> LENGTH: 55
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Cys Tyr Pro Thr Val Thr Lys Gly Val Ser Ala Ala Cys Pro Glu Ser
1               5                   10                  15

Ser Phe Ile Trp Leu Thr Gly Ile His His Pro Pro Asn Ile Gly Asp
            20                  25                  30

Gln Lys Thr Leu Tyr His Glu Ile Ala Lys Arg Pro Lys Val Arg Asp
```

```
                    35                  40                  45

Gln Glu Gly Arg Ile Asn Val
    50                  55

<210> SEQ ID NO 30
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Leu Gly Asn Pro Gly Thr Cys Tyr Pro Gly Tyr Lys Trp Asn His Thr
1               5                   10                  15

Val Thr Gly Val Thr Ala Ser Cys Ser His Ala Gly Lys Ser Ser Phe
                20                  25                  30

Tyr Arg Asn Leu Leu Trp Leu Thr Gly Lys Asn Gly Ser Tyr Pro Trp
            35                  40                  45

Gly Val His His Pro Ser Asn Ile Gly Asp Gln Gln Thr Leu Tyr Gln
    50                  55                  60

Thr Glu Asn Ala Phe Thr Pro Glu Ile Ala Lys Arg Pro Lys Val Arg
65                  70                  75                  80

Asp Gln Glu Gly Arg Met Asn Tyr Ala Asn Gly Asn Leu Ile Ala Pro
                85                  90                  95

Trp

<210> SEQ ID NO 31
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Leu Gly Asn Pro Gly Thr Cys Tyr Pro Gly Tyr Lys Trp Asn His Asp
1               5                   10                  15

Val Thr Gly Val Ser Ala Ser Cys Ser His Asn Gly Ala Ser Ser Phe
                20                  25                  30

Tyr Arg Asn Leu Leu Trp Leu Thr Lys Lys Asn Asn Leu Tyr Pro Trp
            35                  40                  45

Gly Val His His Pro Ser Thr Ile Ala Asp Gln Gln Thr Leu Tyr His
    50                  55                  60

Thr Glu Asn Ala Phe Thr Pro Glu Ile Ala Ile Arg Pro Lys Val Arg
65                  70                  75                  80

Asp Gln Glu Gly Arg Ile Asn Tyr Ala Asn Gly Asn Leu Ile Ala Pro
                85                  90                  95

Trp

<210> SEQ ID NO 32
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 32

Leu Gly Asn Pro Gly Thr Cys Tyr Pro Gly Tyr Lys Trp Asn His Asp
1               5                   10                  15

Ser Asn Gly Val Thr Ala Ser Cys Pro His Ala Gly Ala Lys Ser Phe
            20                  25                  30

Tyr Arg Asn Leu Leu Trp Leu Val Lys Lys Gly Asn Ser Tyr Pro Trp
        35                  40                  45

Gly Val His His Pro Ser Thr Ser Ala Asp Gln Gln Ser Leu Tyr Gln
    50                  55                  60

Asn Ala Asn Ala Phe Thr Pro Glu Ile Ala Ile Arg Pro Lys Val Arg
65                  70                  75                  80

Asp Gln Glu Gly Arg Met Asn Tyr Ala Thr Gly Asn Leu Ile Ala Pro
                85                  90                  95

Trp

<210> SEQ ID NO 33
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Leu Gly Asn Pro Gly Thr Cys Tyr Pro Gly Tyr Lys Trp Asn His Thr
1               5                   10                  15

Val Thr Gly Val Ser Ala Ser Cys Ser His Asn Gly Lys Ser Ser Phe
            20                  25                  30

Tyr Arg Asn Leu Leu Trp Leu Thr Gly Lys Asn Gly Leu Tyr Pro Trp
        35                  40                  45

Gly Val His His Pro Pro Asn Ile Gly Asp Gln Arg Ala Leu Tyr His
    50                  55                  60

Thr Glu Asn Ala Phe Thr Pro Glu Ile Ala Lys Arg Pro Lys Val Arg
65                  70                  75                  80

Asp Gln Glu Gly Arg Ile Asn Tyr Ala Asn Gly Asn Leu Ile Ala Pro
                85                  90                  95

Trp

<210> SEQ ID NO 34
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Leu Gly Asn Pro Gly Thr Cys Tyr Pro Gly Tyr Lys Trp Asn His Thr
1               5                   10                  15

Val Thr Gly Val Ser Ala Ser Cys Pro His Asn Gly Glu Ser Ser Phe
            20                  25                  30

Tyr Arg Asn Leu Leu Trp Leu Thr Gly Lys Asn Gly Leu Tyr Pro Trp
        35                  40                  45

Gly Val His His Pro Pro Asn Ile Gly Asp Gln Lys Thr Leu Tyr His
    50                  55                  60

Thr Glu Asn Ala Phe Thr Pro Glu Ile Ala Lys Arg Pro Lys Val Arg

```
                65                  70                  75                  80

Asp Gln Glu Gly Arg Ile Asn Tyr Ala Asn Gly Asn Leu Ile Ala Pro
                85                  90                  95

Trp

<210> SEQ ID NO 35
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Leu Gly Asn Pro Gly Thr Cys Tyr Pro Gly Asp Lys Trp Asn His Thr
1               5                   10                  15

Val Thr Lys Gly Val Thr Ala Ala Cys Ser His Ala Gly Lys Ser Ser
                20                  25                  30

Phe Tyr Lys Asn Leu Ile Trp Leu Thr Gly Lys Asn Gly Ser Tyr Pro
            35                  40                  45

Trp Gly Ile His His Pro Ser Asn Ile Gly Asp Gln Gln Thr Leu Tyr
        50                  55                  60

Gln Thr Glu Asp Thr Phe Lys Pro Glu Ile Ala Lys Arg Pro Lys Val
65                  70                  75                  80

Arg Asp Gln Glu Gly Arg Met Asn Tyr Ala Asn Gly Asn Leu Val Val
                85                  90                  95

Pro Arg

<210> SEQ ID NO 36
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Leu Gly Asn Pro Gly Thr Cys Tyr Pro Gly Asp Lys Trp Asn His Asp
1               5                   10                  15

Val Thr Lys Gly Val Ser Ala Ala Cys Ser His Asn Gly Ala Ser Ser
                20                  25                  30

Phe Tyr Lys Asn Leu Ile Trp Leu Thr Lys Lys Asn Asn Leu Tyr Pro
            35                  40                  45

Trp Gly Ile His His Pro Ser Thr Ile Ala Asp Gln Gln Thr Leu Tyr
        50                  55                  60

His Thr Glu Asp Thr Phe Lys Pro Glu Ile Ala Ile Arg Pro Lys Val
65                  70                  75                  80

Arg Asp Gln Glu Gly Arg Ile Asn Tyr Ala Asn Gly Asn Leu Val Val
                85                  90                  95

Pro Arg

<210> SEQ ID NO 37
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 37

Leu Gly Asn Pro Gly Thr Cys Tyr Pro Gly Asp Lys Trp Asn His Asp
1               5                   10                  15

Ser Asn Lys Gly Val Thr Ala Ala Cys Pro His Ala Gly Ala Lys Ser
            20                  25                  30

Phe Tyr Lys Asn Leu Ile Trp Leu Val Lys Lys Gly Asn Ser Tyr Pro
        35                  40                  45

Trp Gly Ile His His Pro Ser Thr Ser Ala Asp Gln Gln Ser Leu Tyr
    50                  55                  60

Gln Asn Ala Asp Thr Phe Lys Pro Glu Ile Ala Ile Arg Pro Lys Val
65                  70                  75                  80

Arg Asp Gln Glu Gly Arg Met Asn Tyr Ala Thr Gly Asn Leu Val Val
                85                  90                  95

Pro Arg

<210> SEQ ID NO 38
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Leu Gly Asn Pro Gly Thr Cys Tyr Pro Gly Asp Lys Trp Asn His Thr
1               5                   10                  15

Val Thr Lys Gly Val Ser Ala Ala Cys Ser His Asn Gly Lys Ser Ser
            20                  25                  30

Phe Tyr Lys Asn Leu Ile Trp Leu Thr Gly Lys Asn Gly Leu Tyr Pro
        35                  40                  45

Trp Gly Ile His His Pro Pro Asn Ile Gly Asp Gln Arg Ala Leu Tyr
    50                  55                  60

His Thr Glu Asp Thr Phe Lys Pro Glu Ile Ala Lys Arg Pro Lys Val
65                  70                  75                  80

Arg Asp Gln Glu Gly Arg Ile Asn Tyr Ala Asn Gly Asn Leu Val Val
                85                  90                  95

Pro Arg

<210> SEQ ID NO 39
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Leu Gly Asn Pro Gly Thr Cys Tyr Pro Gly Asp Lys Trp Asn His Thr
1               5                   10                  15

Val Thr Lys Gly Val Ser Ala Ala Cys Pro His Asn Gly Glu Ser Ser
            20                  25                  30

Phe Tyr Lys Asn Leu Ile Trp Leu Thr Gly Lys Asn Gly Leu Tyr Pro
        35                  40                  45

Trp Gly Ile His His Pro Pro Asn Ile Gly Asp Gln Lys Thr Leu Tyr
    50                  55                  60

```
His Thr Glu Asp Thr Phe Lys Pro Glu Ile Ala Lys Arg Pro Lys Val
 65                  70                  75                  80

Arg Asp Gln Glu Gly Arg Ile Asn Tyr Ala Asn Gly Asn Leu Val Val
                 85                  90                  95

Pro Arg

<210> SEQ ID NO 40
<211> LENGTH: 585
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Met Lys Ala Ile Ile Val Leu Leu Met Val Val Thr Ser Asn Ala Asp
 1               5                  10                  15

Arg Ile Cys Thr Gly Ile Thr Ser Ser Asn Ser Pro His Val Val Lys
                 20                  25                  30

Thr Ala Thr Gln Gly Glu Val Asn Val Thr Gly Val Ile Pro Leu Thr
             35                  40                  45

Thr Thr Pro Thr Lys Ser His Phe Ala Asn Leu Lys Gly Thr Glu Thr
 50                  55                  60

Arg Gly Lys Leu Cys Pro Lys Cys Leu Asn Cys Thr Asp Leu Asp Val
 65                  70                  75                  80

Ala Leu Gly Arg Pro Lys Cys Thr Gly Lys Ile Pro Ser Ala Arg Val
                 85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
            115                 120                 125

Tyr Glu His Ile Arg Leu Ser Thr Gln Asn Val Ile Asn Ala Glu Asn
130                 135                 140

Ala Pro Gly Gly Pro Tyr Lys Ile Gly Thr Ser Gly Ser Cys Pro Asn
145                 150                 155                 160

Ala Thr Asn Lys Ser Gly Phe Phe Ala Thr Met Ala Trp Ala Val Pro
                165                 170                 175

Lys Asn Asp Asn Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
            195                 200                 205

His Ser Asp Asn Lys Thr Gln Met Lys Lys Leu Tyr Gly Asp Ser Lys
210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Pro Gly Lys
            260                 265                 270

Thr Gly Thr Ile Val Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
290                 295                 300

Ile Gly Glu Ala Asp Cys Leu His Glu Lys Tyr Gly Gly Leu Asn Lys
```

```
            305                 310                 315                 320
Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Ala Lys Leu Leu Lys Glu Arg Gly Phe Phe Gly Ala Ile
                355                 360                 365

Ala Gly Phe Leu Glu Gly Gly Trp Glu Gly Met Ile Ala Gly Trp His
            370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
                435                 440                 445

Leu Arg Ala Asp Thr Ile Ser Ser Gln Ile Glu Leu Ala Val Leu Leu
                450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
                515                 520                 525

Phe Asp Ser Leu Asn Ile Thr Ala Ala Ser Leu Asn Asp Asp Gly Leu
                530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
                580                 585

<210> SEQ ID NO 41
<211> LENGTH: 585
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser Tyr Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80
```

```
Ala Leu Gly Arg Pro Lys Cys Thr Gly Lys Ile Pro Ser Ala Lys Val
            85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr Gln Asn Val Ile Asp Ala Glu Asn
            130                 135                 140

Ala Pro Gly Gly Pro Tyr Lys Ile Gly Thr Ser Gly Ser Cys Pro Asn
145                 150                 155                 160

Ala Thr Asn Lys Ser Gly Phe Phe Ala Thr Met Ala Trp Ala Val Pro
            165                 170                 175

Lys Asn Asp Asn Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Lys Thr Gln Met Lys Lys Leu Tyr Gly Asp Ser Lys
            210                 215                 220

Pro Gln Lys Phe Thr Ser Ser Ala Asn Gly Val Thr Thr His Tyr Val
225                 230                 235                 240

Ser Gln Ile Gly Gly Phe Pro Asp Gln Thr Glu Asp Gly Gly Leu Pro
            245                 250                 255

Gln Ser Gly Arg Ile Val Val Asp Tyr Met Val Gln Lys Pro Gly Lys
            260                 265                 270

Thr Gly Thr Ile Val Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
            290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
            325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Val Ala Gly Trp His
            370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
            405                 410                 415

Leu Ser Glu Leu Glu Ile Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
            450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
            485                 490                 495
```

```
Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ala Ser Leu Asn Asp Asp Gly Leu
            530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585

<210> SEQ ID NO 42
<211> LENGTH: 585
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Ser Leu Thr
            35                  40                  45

Thr Thr Pro Thr Lys Ser His Phe Ala Asn Leu Lys Gly Thr Lys Thr
50                  55                  60

Arg Gly Lys Leu Cys Pro Lys Cys Pro Asn Cys Thr Asp Leu Asp Val
65                  70                  75                  80

Ala Leu Gly Arg Pro Met Cys Thr Gly Thr Ile Pro Ser Ala Lys Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
            115                 120                 125

Tyr Glu His Ile Arg Leu Ser Thr His Asn Val Ile Asn Ala Glu Asn
            130                 135                 140

Ala Pro Gly Gly Pro Tyr Lys Ile Gly Thr Ser Gly Ser Cys Pro Asn
145                 150                 155                 160

Ala Thr Asn Lys Ile Gly Phe Phe Ala Thr Met Ala Trp Ala Val Pro
                165                 170                 175

Lys Asn Asp Asn Asn Lys Thr Ala Thr Asn Pro Leu Thr Ile Glu Val
            180                 185                 190

Pro Tyr Ile Cys Ala Glu Gly Glu Asp Gln Ile Thr Val Trp Gly Phe
            195                 200                 205

His Ser Asp Asp Lys Thr Gln Met Lys Lys Leu Tyr Gly Asp Ser Lys
            210                 215                 220

Pro Gln Lys Phe Thr Ser Ser Ala Asn Gly Val Thr Thr His Tyr Val
225                 230                 235                 240

Ser Gln Ile Gly Asp Phe Pro Asn Gln Thr Glu Asp Gly Gly Leu Pro
                245                 250                 255

Gln Ser Gly Arg Ile Val Val Asp Tyr Met Val Gln Lys Pro Gly Lys
```

```
                260                 265                 270
Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Thr Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
        370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asn
            500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu Asn Asp Asp Gly Leu
530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585

<210> SEQ ID NO 43
<211> LENGTH: 585
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30
```

-continued

```
Thr Ala Thr Gln Gly Glu Val Asn Val Thr Gly Val Ile Pro Leu Thr
        35                  40                  45
Thr Thr Pro Thr Lys Ser Tyr Phe Ala Asn Leu Lys Gly Thr Glu Thr
 50                  55                  60
Arg Gly Lys Leu Cys Pro Asn Cys Leu Asn Cys Thr Asp Leu Asp Val
 65                  70                  75                  80
Ala Leu Gly Arg Pro Lys Cys Val Gly Lys Ile Pro Ser Ala Lys Ala
                 85                  90                  95
Ser Ile Leu His Glu Val Arg Pro Val Thr Ser Gly Cys Phe Pro Ile
                100                 105                 110
Met His Asp Arg Thr Lys Ile Arg Gln Leu Pro Asn Leu Leu Arg Gly
            115                 120                 125
Tyr Glu His Ile Arg Leu Ser Thr Gln Asn Val Ile Asp Ala Glu Arg
        130                 135                 140
Ala Pro Gly Gly Pro Tyr Arg Leu Gly Thr Ser Gly Ser Cys Pro Asn
145                 150                 155                 160
Ala Thr Ser Lys Ser Gly Phe Phe Ala Thr Met Ala Trp Ala Val Pro
                165                 170                 175
Lys Asp Asp Asn Asn Lys Thr Ala Thr Asn Pro Leu Thr Val Glu Val
                180                 185                 190
Pro Tyr Ile Cys Thr Glu Gly Glu Asp Gln Ile Thr Val Trp Gly Phe
            195                 200                 205
His Ser Asp Asn Lys Thr Gln Met Lys Asn Leu Tyr Gly Asp Ser Asn
        210                 215                 220
Pro Gln Lys Phe Thr Ser Ser Ala Asn Gly Val Thr Thr His Tyr Val
225                 230                 235                 240
Ser Gln Ile Gly Gly Phe Pro Asp Gln Thr Glu Asp Gly Gly Leu Pro
                245                 250                 255
Gln Ser Gly Arg Ile Val Val Asp Tyr Met Val Gln Lys Pro Gly Lys
                260                 265                 270
Thr Gly Thr Ile Val Tyr Gln Arg Gly Val Leu Leu Pro Gln Lys Val
            275                 280                 285
Trp Cys Ala Ser Gly Arg Ser Lys Val Ile Lys Gly Ser Leu Pro Leu
        290                 295                 300
Ile Gly Glu Ala Asp Cys Leu His Glu Lys Tyr Gly Gly Leu Asn Lys
305                 310                 315                 320
Ser Lys Pro Tyr Tyr Thr Gly Glu His Ala Lys Ala Ile Gly Asn Cys
                325                 330                 335
Pro Ile Trp Val Lys Thr Pro Leu Lys Leu Ala Asn Gly Thr Lys Tyr
            340                 345                 350
Arg Pro Pro Ala Lys Leu Leu Lys Glu Arg Gly Phe Phe Gly Ala Ile
        355                 360                 365
Ala Gly Phe Leu Glu Gly Gly Trp Glu Gly Met Val Ala Gly Trp His
    370                 375                 380
Gly Tyr Thr Ser His Gly Ala His Gly Val Ala Val Ala Ala Asp Leu
385                 390                 395                 400
Lys Ser Thr Gln Glu Ala Ile Asn Lys Ile Thr Lys Asn Leu Asn Ser
                405                 410                 415
Leu Ser Glu Leu Glu Ile Lys Asn Leu Gln Arg Leu Ser Gly Ala Met
            420                 425                 430
Asp Glu Leu His Asn Glu Ile Leu Glu Leu Asp Glu Lys Val Asp Asp
        435                 440                 445
```

```
Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Asp Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asn Ala Gly Glu Phe Ser Leu Pro Thr
        515                 520                 525

Phe Asp Ser Leu Asn Ile Thr Ala Ala Ser Leu Asn Asp Asp Gly Leu
530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Ile Val Tyr Met Val Ser Arg
                565                 570                 575

Asp Asn Val Ser Cys Ser Ile Cys Leu
                580                 585

<210> SEQ ID NO 44
<211> LENGTH: 585
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Met Lys Ala Ile Ile Val Leu Leu Met Val Val Thr Ser Asn Ala Asp
1               5                   10                  15

Arg Ile Cys Thr Gly Ile Thr Ser Ser Lys Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Arg Gly Thr Lys Thr
    50                  55                  60

Arg Gly Lys Leu Cys Pro Asp Cys Leu Asn Cys Thr Asp Leu Asp Val
65                  70                  75                  80

Ala Leu Gly Arg Pro Lys Cys Val Gly Asn Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Ala Asn Leu Leu Arg Gly
        115                 120                 125

Tyr Glu His Ile Arg Leu Ser Asn Tyr Asn Val Ile Asp Ala Glu Lys
    130                 135                 140

Ala Pro Gly Gly Pro Tyr Arg Leu Gly Thr Ser Arg Ser Cys Pro Asn
145                 150                 155                 160

Val Thr Ser Arg Ser Gly Phe Phe Ala Thr Met Ala Trp Ala Val Pro
                165                 170                 175

Lys Asp Asp Ser Asn Lys Asn Ala Thr Asn Pro Leu Thr Val Glu Val
            180                 185                 190

Pro Tyr Ile Cys Thr Glu Gly Glu Asp Gln Ile Thr Val Trp Gly Phe
        195                 200                 205

His Ser Asp Asn Lys Thr Gln Met Val Asn Leu Tyr Gly Asp Ser Asn
```

```
              210                 215                 220
Pro Gln Lys Phe Thr Ser Ser Ala Asn Gly Val Thr Thr His Tyr Val
225                 230                 235                 240

Ser Gln Ile Gly Asp Phe Pro Asn Gln Thr Glu Asp Gly Gly Leu Pro
                245                 250                 255

Gln Ser Gly Arg Ile Val Val Asp Tyr Met Met Gln Lys Ser Gly Lys
                260                 265                 270

Thr Gly Thr Ile Thr Tyr Gln Arg Gly Val Leu Leu Pro Gln Lys Val
            275                 280                 285

Trp Cys Ala Ser Gly Arg Ser Lys Val Ile Lys Gly Thr Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp His
        370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
        450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Asp Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asn Ala Gly Glu Phe Ser Leu Pro Thr
            515                 520                 525

Phe Asp Ser Leu Asn Ile Thr Ala Ala Ser Leu Asn Asp Asp Gly Leu
        530                 535                 540

Asp Asn His Thr Ile Leu Leu Tyr Tyr Ser Thr Ala Ala Ser Ser Leu
545                 550                 555                 560

Ala Val Thr Leu Met Leu Ala Ile Phe Ile Val Tyr Met Val Ser Arg
                565                 570                 575

Asp Asn Val Ser Cys Ser Ile Cys Leu
                580                 585
```

<210> SEQ ID NO 45
<211> LENGTH: 585
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 45

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Lys Thr
    50                  55                  60

Arg Gly Lys Leu Cys Pro Asn Cys Leu Asn Cys Thr Asp Leu Asp Val
65                  70                  75                  80

Ala Leu Gly Arg Pro Met Cys Met Gly Thr Ile Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr His Asn Val Ile Asn Ala Glu Arg
    130                 135                 140

Ala Pro Gly Gly Pro Tyr Ile Ile Gly Thr Ser Gly Ser Cys Pro Asn
145                 150                 155                 160

Ala Thr Asn Lys Asn Gly Phe Phe Ala Thr Met Ala Trp Ala Val Pro
                165                 170                 175

Lys Asp Asp Asn Asn Lys Thr Ala Thr Asn Pro Leu Thr Val Glu Val
            180                 185                 190

Pro Tyr Ile Cys Thr Glu Gly Glu Asp Gln Ile Thr Val Trp Gly Phe
        195                 200                 205

His Ser Asp Asn Lys Thr Gln Met Lys Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asp Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Val Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400
```

-continued

```
Lys Ser Thr Gln Glu Ala Ile Asn Lys Ile Thr Lys Asn Leu Asn Ser
            405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Asp Ile Gly
            485                 490                 495

Asn Gly Cys Phe Glu Thr Lys His Lys Cys Asn Gln Thr Cys Leu Asp
            500                 505                 510

Arg Ile Ala Ala Gly Thr Phe Asn Ala Gly Glu Phe Ser Leu Pro Thr
            515                 520                 525

Phe Asp Ser Leu Asn Ile Thr Ala Ala Ser Leu Asn Asp Asp Gly Leu
            530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Ile Val Tyr Met Val Ser Arg
            565                 570                 575

Asp Asn Val Ser Cys Ser Ile Cys Leu
            580                 585
```

<210> SEQ ID NO 46
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

```
Gly Lys Ala Pro Leu Lys Pro Glu Ser Leu Thr Ser Asp Gly Asp Pro
1               5                   10                  15

Val His
```

<210> SEQ ID NO 47
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

```
Gly Lys Ala Pro Leu Asn Pro Glu Leu Leu Lys Asn Glu Gly Asn Pro
1               5                   10                  15

Met Asp
```

<210> SEQ ID NO 48
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 48

Gly Lys Ala Pro Leu Asn Pro Glu Leu Leu Thr Asn Glu Gly Asn Pro
1               5                   10                  15

Met Asp

<210> SEQ ID NO 49
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gly Lys Ala Pro Leu Lys Pro Glu Thr Leu Thr Ser Asp Gly Asp Pro
1               5                   10                  15

Val His

<210> SEQ ID NO 50
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Gly Lys Ala Pro Leu Asn Pro Glu Leu Leu Thr Asn Glu Gly Asn Pro
1               5                   10                  15

Met Gly

<210> SEQ ID NO 51
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Tyr Asp Asn Lys Gly Val Thr Ala Lys Trp Val Lys Lys Gly Asn Ser
1               5                   10                  15

His Ser Thr Ser Ala Asp Gln Ser Leu Gln Ile Asp Gln Glu
            20                  25                  30

<210> SEQ ID NO 52
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Tyr Asp Asn Lys Gly Val Thr Ala Lys Trp Val Lys Lys Gly Asn Ser
1               5                   10                  15

His Ser Thr Thr Ala Asp Gln Ser Leu Gln Ile Asp Gln Glu
            20                  25                  30
```

```
<210> SEQ ID NO 53
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Tyr Thr Thr Gly Val Ser Ala Ser Trp Thr Gly Lys Asn Gly Leu His
1               5                   10                  15

Pro Asn Ile Gly Asp Arg Ala Leu His Lys Asp Gln Glu
            20                  25

<210> SEQ ID NO 54
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Tyr Asp Asn Lys Gly Val Thr Ala Lys Trp Val Lys Lys Gly Asn Ser
1               5                   10                  15

His Ser Thr Ser Ala Asp Gln Ser Leu Gln Ile Glu Gln Glu
            20                  25                  30

<210> SEQ ID NO 55
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Tyr Thr Thr Gly Val Ser Ala Ser Trp Thr Gly Lys Asn Gly Leu His
1               5                   10                  15

Pro Asn Ile Gly Asp Lys Ala Leu His Lys Asp Gln Glu
            20                  25

<210> SEQ ID NO 56
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Ser His Asn Gly Glu Ser Arg Asp
1               5

<210> SEQ ID NO 57
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57
```

Ser His Asn Gly Lys Ser Arg Asp
1               5

<210> SEQ ID NO 58
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Pro His Ala Gly Ala Lys Arg Glu
1               5

<210> SEQ ID NO 59
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Pro His Ala Gly Ala Lys Arg Gly
1               5

<210> SEQ ID NO 60
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Tyr His His Ser Leu Val Asp Gly Trp Leu Thr Gln Ala Ile Asp Ile
1               5                   10                  15

Thr Lys Val Asn Val Ile Thr
            20

<210> SEQ ID NO 61
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Tyr His His Ser Leu Val Asp Gly Trp Gln Thr Gln Ala Ile Asn Ile
1               5                   10                  15

Thr Lys Val Asn Val Ile Thr
            20

<210> SEQ ID NO 62
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Tyr His His Ser Leu Ile Asp Gly Trp Gln Thr Gln Ala Ile Asn Ile
1               5                   10                  15

Thr Lys Val Asn Val Ile Thr
            20

<210> SEQ ID NO 63
<211> LENGTH: 53
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Asn Ile Thr Ala Ala Ser Ser Gly Arg Ser Leu Val Pro Arg Gly Ser
1               5                   10                  15

Pro Gly Ser Gly Tyr Ile Pro Glu Ala Pro Arg Asp Gly Gln Ala Tyr
            20                  25                  30

Val Arg Lys Asp Gly Glu Trp Val Leu Leu Ser Thr Phe Leu Gly His
        35                  40                  45

His His His His His
    50

<210> SEQ ID NO 64
<211> LENGTH: 22
<212> TYPE: PRT
<213> ORGANISM: Influenza virus

<400> SEQUENCE: 64

Ile Leu Gly Asn Ser Glu Cys Glu Leu Leu Ile Ser Lys Glu Ser Trp
1               5                   10                  15

Ser Tyr Ile Val Glu Lys
            20

<210> SEQ ID NO 65
<211> LENGTH: 22
<212> TYPE: PRT
<213> ORGANISM: Influenza virus

<400> SEQUENCE: 65

Ile Leu Gly Asn Pro Glu Cys Asp Ser Leu Leu Pro Ala Ser Ser Trp
1               5                   10                  15

Ser Tyr Ile Val Glu Thr
            20

<210> SEQ ID NO 66
<211> LENGTH: 22
<212> TYPE: PRT
<213> ORGANISM: Influenza virus

<400> SEQUENCE: 66

Val Leu Gly Asn Pro Glu Cys Glu Ser Leu Leu Ser Asn Arg Ser Trp
1               5                   10                  15

Ser Tyr Ile Ala Glu Thr
            20

<210> SEQ ID NO 67
<211> LENGTH: 22
<212> TYPE: PRT

<213> ORGANISM: Influenza virus

<400> SEQUENCE: 67

Leu Leu Gly Asn Pro Glu Cys Asp Pro Leu Leu Pro Val Arg Ser Trp
1               5                   10                  15

Ser Tyr Ile Val Glu Thr
            20

<210> SEQ ID NO 68
<211> LENGTH: 22
<212> TYPE: PRT
<213> ORGANISM: Influenza virus

<400> SEQUENCE: 68

Leu Leu Gly Asn Pro Glu Cys Asp Ser Leu Leu Pro Ala Ser Ser Trp
1               5                   10                  15

Ser Tyr Ile Val Glu Thr
            20

<210> SEQ ID NO 69
<211> LENGTH: 22
<212> TYPE: PRT
<213> ORGANISM: Influenza virus

<400> SEQUENCE: 69

Ile Leu Gly Asn Pro Glu Cys Glu Leu Leu Val Ser Lys Glu Ser Trp
1               5                   10                  15

Ser Tyr Ile Val Glu Lys
            20

<210> SEQ ID NO 70
<211> LENGTH: 22
<212> TYPE: PRT
<213> ORGANISM: Influenza virus

<400> SEQUENCE: 70

Val Leu Gly Asn Pro Glu Cys Glu Ser Leu Leu Ser Asn Arg Ser Trp
1               5                   10                  15

Ser Tyr Ile Ala Glu Thr
            20

<210> SEQ ID NO 71
<211> LENGTH: 22
<212> TYPE: PRT
<213> ORGANISM: Influenza virus

<400> SEQUENCE: 71

Leu Leu Gly Asn Pro Glu Cys Asp Pro Leu Leu Pro Ala Arg Ser Trp
1               5                   10                  15

Ser Tyr Ile Val Glu Thr
            20

<210> SEQ ID NO 72
<211> LENGTH: 22
<212> TYPE: PRT
<213> ORGANISM: Influenza virus

<400> SEQUENCE: 72

Leu Leu Gly Asn Pro Glu Cys Asp Ser Leu Leu Pro Ala Arg Ser Trp
1               5                   10                  15

Ser Tyr Ile Val Glu Thr
            20

```
<210> SEQ ID NO 73
<211> LENGTH: 22
<212> TYPE: PRT
<213> ORGANISM: Influenza virus

<400> SEQUENCE: 73

Leu Leu Gly Asn Pro Glu Cys Asp Pro Leu Leu Pro Val Arg Ser Trp
1               5                   10                  15

Ser Tyr Ile Val Glu Thr
            20

<210> SEQ ID NO 74
<211> LENGTH: 22
<212> TYPE: PRT
<213> ORGANISM: Influenza virus

<400> SEQUENCE: 74

Leu Leu Gly Asn Pro Glu Cys Asp Pro Leu Leu Pro Val Arg Ser Trp
1               5                   10                  15

Ser Tyr Ile Val Glu Thr
            20

<210> SEQ ID NO 75
<211> LENGTH: 22
<212> TYPE: PRT
<213> ORGANISM: Influenza virus

<400> SEQUENCE: 75

Leu Leu Gly Asn Pro Glu Cys Asp Pro Leu Leu Pro Val Arg Ser Trp
1               5                   10                  15

Ser Tyr Ile Val Glu Thr
            20

<210> SEQ ID NO 76
<211> LENGTH: 22
<212> TYPE: PRT
<213> ORGANISM: Influenza virus

<400> SEQUENCE: 76

Leu Leu Gly Asn Pro Glu Cys Asp Ser Leu Leu Pro Ala Arg Ser Trp
1               5                   10                  15

Ser Tyr Ile Val Glu Thr
            20

<210> SEQ ID NO 77
<211> LENGTH: 22
<212> TYPE: PRT
<213> ORGANISM: Influenza virus

<400> SEQUENCE: 77

Leu Leu Gly Asn Pro Glu Cys Asp Ser Leu Leu Pro Ala Arg Ser Trp
1               5                   10                  15

Ser Tyr Ile Val Glu Thr
            20

<210> SEQ ID NO 78
<211> LENGTH: 22
<212> TYPE: PRT
<213> ORGANISM: Influenza virus

<400> SEQUENCE: 78
```

Leu Leu Gly Asn Pro Glu Cys Glu Leu Leu Thr Val Ser Ser Trp
1               5                   10                  15

Ser Tyr Ile Val Glu Thr
            20

<210> SEQ ID NO 79
<211> LENGTH: 22
<212> TYPE: PRT
<213> ORGANISM: Influenza virus

<400> SEQUENCE: 79

Leu Leu Gly Asn Pro Glu Cys Glu Leu Leu Thr Val Ser Ser Trp
1               5                   10                  15

Ser Tyr Ile Val Glu Thr
            20

<210> SEQ ID NO 80
<211> LENGTH: 22
<212> TYPE: PRT
<213> ORGANISM: Influenza virus

<400> SEQUENCE: 80

Leu Leu Gly Asn Pro Glu Cys Glu Leu Leu Phe Thr Ala Ser Ser Trp
1               5                   10                  15

Ser Tyr Ile Val Glu Thr
            20

<210> SEQ ID NO 81
<211> LENGTH: 22
<212> TYPE: PRT
<213> ORGANISM: Influenza virus

<400> SEQUENCE: 81

Leu Leu Gly Asn Pro Glu Cys Glu Leu Leu Phe Thr Ala Ser Ser Trp
1               5                   10                  15

Ser Tyr Ile Val Glu Thr
            20

<210> SEQ ID NO 82
<211> LENGTH: 22
<212> TYPE: PRT
<213> ORGANISM: Influenza virus

<400> SEQUENCE: 82

Leu Leu Gly Asn Pro Glu Cys Glu Leu Leu Phe Thr Ala Ser Ser Trp
1               5                   10                  15

Ser Tyr Ile Val Glu Thr
            20

<210> SEQ ID NO 83
<211> LENGTH: 22
<212> TYPE: PRT
<213> ORGANISM: Influenza virus

<400> SEQUENCE: 83

Leu Leu Gly Asn Pro Glu Cys Glu Ser Leu Ser Thr Ala Ser Ser Trp
1               5                   10                  15

Ser Tyr Ile Val Glu Thr
            20

<210> SEQ ID NO 84
<211> LENGTH: 22

```
<212> TYPE: PRT
<213> ORGANISM: Influenza virus

<400> SEQUENCE: 84

Leu Leu Gly Asn Pro Glu Cys Glu Leu Le

```
<211> LENGTH: 6
<212> TYPE: PRT
<213> ORGANISM: Influenza virus

<400> SEQUENCE: 91

Leu Leu Ser Asn Arg Ser
1               5

<210> SEQ ID NO 92
<211> LENGTH: 6
<212> TYPE: PRT
<213> ORGANISM: Influenza virus

<400> SEQUENCE: 92

Leu Leu Pro Ala Arg Ser
1               5

<210> SEQ ID NO 93
<211> LENGTH: 6
<212> TYPE: PRT
<213> ORGANISM: Influenza virus

<400> SEQUENCE: 93

Leu Leu Pro Ala Arg Ser
1               5

<210> SEQ ID NO 94
<211> LENGTH: 6
<212> TYPE: PRT
<213> ORGANISM: Influenza virus

<400> SEQUENCE: 94

Leu Leu Pro Val Arg Ser
1               5

<210> SEQ ID NO 95
<211> LENGTH: 6
<212> TYPE: PRT
<213> ORGANISM: Influenza virus

<400> SEQUENCE: 95

Leu Leu Pro Val Arg Ser
1               5

<210> SEQ ID NO 96
<211> LENGTH: 6
<212> TYPE: PRT
<213> ORGANISM: Influenza virus

<400> SEQUENCE: 96

Leu Leu Pro Val Arg Ser
1               5

<210> SEQ ID NO 97
<211> LENGTH: 6
<212> TYPE: PRT
<213> ORGANISM: Influenza virus

<400> SEQUENCE: 97

Leu Leu Pro Ala Arg Ser
1               5

<210> SEQ ID NO 98
<211> LENGTH: 6
<212> TYPE: PRT
```

<213> ORGANISM: Influenza virus

<400> SEQUENCE: 98

Leu Leu Pro Ala Arg Ser
1               5

<210> SEQ ID NO 99
<211> LENGTH: 6
<212> TYPE: PRT
<213> ORGANISM: Influenza virus

<400> SEQUENCE: 99

Leu Leu Thr Val Ser Ser
1 5

<210> SEQ ID NO 100
<211> LENGTH: 6
<212> TYPE: PRT
<213> ORGANISM: Influenza virus

<400> SEQUENCE: 100

Leu Leu Thr Val Ser Ser
1 5

<210> SEQ ID NO 101
<211> LENGTH: 6
<212> TYPE: PRT
<213> ORGANISM: Influenza virus

<400> SEQUENCE: 101

Leu Phe Thr Ala Ser Ser
1 5

<210> SEQ ID NO 102
<211> LENGTH: 6
<212> TYPE: PRT
<213> ORGANISM: Influenza virus

<400> SEQUENCE: 102

Leu Phe Thr Ala Ser Ser
1 5

<210> SEQ ID NO 103
<211> LENGTH: 6
<212> TYPE: PRT
<213> ORGANISM: Influenza virus

<400> SEQUENCE: 103

Leu Phe Thr Ala Ser Ser
1 5

<210> SEQ ID NO 104
<211> LENGTH: 6
<212> TYPE: PRT
<213> ORGANISM: Influenza virus

<400> SEQUENCE: 104

Leu Ser Thr Ala Ser Ser
1 5

<210> SEQ ID NO 105
<211> LENGTH: 6
<212> TYPE: PRT
<213> ORGANISM: Influenza virus

<400> SEQUENCE: 105

Leu Phe Thr Val Ser Ser
1               5

<210> SEQ ID NO 106
<211> LENGTH: 6
<212> TYPE: PRT
<213> ORGANISM: Influenza virus

<400> SEQUENCE: 106

Leu Ile Ser Lys Glu Ser
1               5

<210> SEQ ID NO 107
<211> LENGTH: 6
<212> TYPE: PRT
<213> ORGANISM: Influenza virus

<400> SEQUENCE: 107

Leu Leu Pro Ala Ser Ser
1               5

<210> SEQ ID NO 108
<211> LENGTH: 6
<212> TYPE: PRT
<213> ORGANISM: Influenza virus

<400> SEQUENCE: 108

Leu Leu Ser Asn Arg Ser
1               5

<210> SEQ ID NO 109
<211> LENGTH: 6
<212> TYPE: PRT
<213> ORGANISM: Influenza virus

<400> SEQUENCE: 109

Leu Leu Pro Val Arg Ser
1               5

<210> SEQ ID NO 110
<211> LENGTH: 6
<212> TYPE: PRT
<213> ORGANISM: Influenza virus

<400> SEQUENCE: 110

Leu Val Ser Lys Glu Ser
1               5

<210> SEQ ID NO 111
<211> LENGTH: 6
<212> TYPE: PRT
<213> ORGANISM: Influenza virus

<400> SEQUENCE: 111

Leu Leu Pro Ala Arg Ser
1               5

<210> SEQ ID NO 112
<211> LENGTH: 6
<212> TYPE: PRT
<213> ORGANISM: Influenza virus

<400> SEQUENCE: 112

Leu Leu Thr Val Ser Ser
1               5

<210> SEQ ID NO 113
<211> LENGTH: 6
<212> TYPE: PRT
<213> ORGANISM: Influenza virus

<400> SEQUENCE: 113

Leu Phe Thr Ala Ser Ser
1               5

<210> SEQ ID NO 114
<211> LENGTH: 6
<212> TYPE: PRT
<213> ORGANISM: Influenza virus

<400> SEQUENCE: 114

Leu Ser Thr Ala Ser Ser
1               5

<210> SEQ ID NO 115
<211> LENGTH: 6
<212> TYPE: PRT
<213> ORGANISM: Influenza virus

<400> SEQUENCE: 115

Leu Phe Thr Val Ser Ser
1               5

<210> SEQ ID NO 116
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Leu Ile Ser Lys Glu Ser
1               5

<210> SEQ ID NO 117
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Leu Leu Pro Val Arg Ser
1               5

<210> SEQ ID NO 118
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Leu Leu Thr Val Ser Ser

```
1               5

<210> SEQ ID NO 119
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Leu Leu Pro Ala Ser Ser
1               5

<210> SEQ ID NO 120
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Leu Val Ser Lys Glu Ser
1               5

<210> SEQ ID NO 121
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Leu Phe Thr Ala Ser Ser
1               5

<210> SEQ ID NO 122
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Leu Leu Ser Asn Arg Ser
1               5

<210> SEQ ID NO 123
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Leu Leu Pro Ala Arg Ser
1               5

<210> SEQ ID NO 124
```

```
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Leu Ser Thr Ala Ser Ser
1               5

<210> SEQ ID NO 125
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Leu Leu Pro Val Arg Ser
1               5

<210> SEQ ID NO 126
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Leu Leu Thr Val Ser Ser
1               5

<210> SEQ ID NO 127
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Leu Phe Thr Val Ser Ser
1               5

<210> SEQ ID NO 128
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Leu Val Ser Lys Glu Ser
1               5

<210> SEQ ID NO 129
<211> LENGTH: 6
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 129

Leu Phe Thr Ala Ser Ser
1               5

<210> SEQ ID NO 130
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

Leu Leu Pro Val Arg Ser
1               5

<210> SEQ ID NO 131
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Val Asn Asn Lys Glu Ser Ser Asn Glu Pro Gly
1               5                   10

<210> SEQ ID NO 132
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

Ser His Ala Arg Lys Ser Arg Asn
1               5

<210> SEQ ID NO 133
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

Leu Leu Pro Ala Arg Ser Trp Ser
1               5

<210> SEQ ID NO 134
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 134

Leu Leu Pro Ala Arg Ser Trp Ser
1               5

<210> SEQ ID NO 135
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Glu Ile Phe Pro
1

<210> SEQ ID NO 136
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Ser Trp Pro Asn
1

<210> SEQ ID NO 137
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Ser His Ala Arg Lys Ser
1               5

<210> SEQ ID NO 138
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Ile Asn Asp Lys Gly Thr Ser Arg Glu Pro Gly
1               5                   10

<210> SEQ ID NO 139
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

Pro His Ala Gly Ala Lys Arg Asp
1               5

```
<210> SEQ ID NO 140
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Leu Ser Thr Ala Ser Ser Trp Ser
1               5

<210> SEQ ID NO 141
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Leu Ser Thr Ala Ser Ser Trp Ser
1               5

<210> SEQ ID NO 142
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Glu Ile Phe Pro
1

<210> SEQ ID NO 143
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Ser Trp Pro Asn
1

<210> SEQ ID NO 144
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

Pro His Ala Gly Ala Lys
1               5

<210> SEQ ID NO 145
<211> LENGTH: 11
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Val Asn Asn Lys Glu Ser Ser Asn Glu Pro Gly
1               5                   10

<210> SEQ ID NO 146
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Ser His Ala Arg Lys Ser Arg Asn
1               5

<210> SEQ ID NO 147
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Leu Leu Pro Ala Arg Ser Trp Ser
1               5

<210> SEQ ID NO 148
<211> LENGTH: 72
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 148

Leu Leu Pro Ala Arg Ser Trp Ser Tyr Ile Val Glu Thr Pro Asn Pro
1               5                   10                  15

Glu Asn Gly Thr Cys Tyr Pro Gly Tyr Phe Ala Asp Tyr Glu Glu Leu
            20                  25                  30

Arg Glu Gln Leu Ser Ser Val Ser Ser Phe Glu Arg Phe Glu Ile Phe
        35                  40                  45

Pro Lys Glu Ser Ser Trp Pro Asn His Glu Thr Asn Gly Val Ser Ala
    50                  55                  60

Ser Cys Ser His Ala Arg Lys Ser
65                  70

<210> SEQ ID NO 149
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 149

Ile Asn Asp Lys Gly Thr Ser Arg Glu Pro Gly
1               5                   10

<210> SEQ ID NO 150
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Pro His Ala Gly Ala Lys Arg Asp
1               5

<210> SEQ ID NO 151
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Leu Ser Thr Ala Ser Ser Trp Ser
1               5

<210> SEQ ID NO 152
<211> LENGTH: 72
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 152

Leu Ser Thr Ala Ser Ser Trp Ser Tyr Ile Val Glu Thr Pro Asn Pro
1               5                   10                  15

Glu Asn Gly Thr Cys Tyr Pro Gly Tyr Phe Ala Asp Tyr Glu Glu Leu
                20                  25                  30

Arg Glu Gln Leu Ser Ser Val Ser Ser Phe Glu Arg Phe Glu Ile Phe
            35                  40                  45

Pro Lys Glu Ser Ser Trp Pro Asn His Thr Val Thr Gly Val Ser Ala
    50                  55                  60

Ser Cys Pro His Ala Gly Ala Lys
65                  70

<210> SEQ ID NO 153
<211> LENGTH: 4
<212> TYPE: PRT
<213> ORGANISM: Influenza virus

<400> SEQUENCE: 153

Val Asp Gly Trp
1

<210> SEQ ID NO 154
<211> LENGTH: 15
<212> TYPE: PRT
<213> ORGANISM: Influenza virus

<400> SEQUENCE: 154

Ser Ser Pro Asn Lys Gly Ser Ser Tyr Pro Lys Ser Lys Ser Val
1               5                   10                  15

<210> SEQ ID NO 155
<211> LENGTH: 8
<212> TYPE: PRT
<213> ORGANISM: Influenza virus

<400> SEQUENCE: 155

Ile Ile Pro Lys Ser Ser Trp Ser
1               5

<210> SEQ ID NO 156
<211> LENGTH: 7
<212> TYPE: PRT
<213> ORGANISM: Influenza virus

<400> SEQUENCE: 156

Ile Ile Trp Glu Ser Lys Asn
1               5

<210> SEQ ID NO 157
<211> LENGTH: 8
<212> TYPE: PRT
<213> ORGANISM: Influenza virus

<400> SEQUENCE: 157

Gln Ile Ile Pro Glu Ala Ser Leu
1               5

<210> SEQ ID NO 158
<211> LENGTH: 7
<212> TYPE: PRT
<213> ORGANISM: Influenza virus

<400> SEQUENCE: 158

Ser Trp Ser Tyr Asn Asn Thr
1               5

<210> SEQ ID NO 159
<211> LENGTH: 9
<212> TYPE: PRT
<213> ORGANISM: Influenza virus

<400> SEQUENCE: 159

Asn Phe Asp Lys Leu Tyr Ile Trp Gly
1               5

<210> SEQ ID NO 160
<211> LENGTH: 13
<212> TYPE: PRT
<213> ORGANISM: Influenza virus

<400> SEQUENCE: 160

Pro Asn Lys Lys Gly Asn Ser Pro Lys Leu Ser Lys Ser
1               5                   10

<210> SEQ ID NO 161
<211> LENGTH: 5
<212> TYPE: PRT
<213> ORGANISM: Influenza virus

<400> SEQUENCE: 161

```
Val Asn Asn Lys Glu
1               5

<210> SEQ ID NO 162
<211> LENGTH: 66
<212> TYPE: PRT
<213> ORGANISM: Influenza virus

<400> SEQUENCE: 162

Phe Glu Ile Phe Pro Lys Thr Ser Ser Trp Pro Asn His Glu Thr Thr
1               5                   10                  15

Lys Gly Val Thr Ala Ala Cys Ser Tyr Ala Gly Ala Ser Ser Phe Tyr
                20                  25                  30

Arg Asn Leu Leu Trp Leu Thr Lys Lys Gly Ser Ser Tyr Pro Lys Leu
            35                  40                  45

Ser Lys Ser Tyr Val Asn Asn Lys Gly Lys Glu Val Leu Val Leu Trp
        50                  55                  60

Gly Val
65

<210> SEQ ID NO 163
<211> LENGTH: 62
<212> TYPE: PRT
<213> ORGANISM: Influenza virus

<400> SEQUENCE: 163

Asn Asn Glu Ser Phe Asn Trp Thr Gly Val Thr Gln Asn Gly Thr Ser
1               5                   10                  15

Ser Ala Cys Lys Arg Arg Ser Asn Asn Ser Phe Phe Ser Arg Leu Asn
                20                  25                  30

Trp Leu Thr Gln Leu Lys Phe Lys Tyr Pro Ala Leu Lys Val Thr Met
            35                  40                  45

Pro Asn Asn Glu Lys Phe Asp Lys Leu Tyr Ile Trp Gly Val
        50                  55                  60
```